United States Patent
Han et al.

(10) Patent No.: US 11,999,954 B2
(45) Date of Patent: Jun. 4, 2024

(54) PROGRAMMABLE CONDITIONAL SIRNAS AND USES THEREOF

(71) Applicants: CITY OF HOPE, Duarte, CA (US); CALIFORNIA INSTITUTE OF TECHNOLOGY, Pasadena, CA (US)

(72) Inventors: Si-ping Han, Duarte, CA (US); William A. Goddard, III, Pasadena, CA (US); Marwa Ben Haj Salah, Duarte, CA (US); Lisa Scherer, Duarte, CA (US); John J. Rossi, Duarte, CA (US)

(73) Assignees: City of Hope, Duarte, CA (US); California Institute of Technology, Pasadena, CA (US)

( * ) Notice: Subject to any disclaimer, the term of this patent is extended or adjusted under 35 U.S.C. 154(b) by 133 days.

(21) Appl. No.: 17/172,461

(22) Filed: Feb. 10, 2021

(65) Prior Publication Data
US 2021/0230593 A1    Jul. 29, 2021

Related U.S. Application Data

(63) Continuation of application No. PCT/US2019/046075, filed on Aug. 10, 2019.
(Continued)

(51) Int. Cl.
*C12N 15/113* (2010.01)

(52) U.S. Cl.
CPC ...... *C12N 15/113* (2013.01); *C12N 2310/141* (2013.01)

(58) Field of Classification Search
CPC . C12N 15/111; C12N 15/113; C12N 2310/14; C12N 2310/315;
(Continued)

(56) References Cited

U.S. PATENT DOCUMENTS

| 6,506,559 B1 | 1/2003 | Fire et al. |
| 6,566,058 B1 | 5/2003 | Cardy |

(Continued)

FOREIGN PATENT DOCUMENTS

| EP | 2101275 A1 | 9/2009 |
| JP | 2018-007663 A | 1/2018 |

(Continued)

OTHER PUBLICATIONS

3DNA, Nucleic Acid Structures, https://x3dna.org/articles/seeing-is-understanding-as-well-as-believing, downloaded Jan. 31, 2022, 4 pages.
(Continued)

*Primary Examiner* — Terra C Gibbs
(74) *Attorney, Agent, or Firm* — Sheppard, Mullin, Richter & Hampton LLP

(57) ABSTRACT

Disclosed herein are programmable, conditionally activated small interfering RNA constructs (Cond-siRNAs) and methods of making and using the same as therapeutic agents. The Cond-siRNA comprises a sensor strand, a core strand, and a guide strand, which crossover to form a sensor duplex and a RNAi duplex attached to each other to form a single structure. Upon binding an input strand to the sensor strand, the Cond-siRNA is activated and releases RNAi targeting a desired gene.

11 Claims, 38 Drawing Sheets
(33 of 38 Drawing Sheet(s) Filed in Color)
Specification includes a Sequence Listing.

Related U.S. Application Data

(60) Provisional application No. 62/811,183, filed on Feb. 27, 2019, provisional application No. 62/717,686, filed on Aug. 10, 2018.

(58) Field of Classification Search
CPC ...... C12N 2310/3231; C12N 2310/346; C12N 2320/50
See application file for complete search history.

(56) References Cited

U.S. PATENT DOCUMENTS

| | | |
|---|---|---|
| 6,696,285 B1 | 2/2004 | Mills et al. |
| 8,318,921 B2 | 11/2012 | Pierce et al. |
| 9,029,524 B2 | 5/2015 | Han et al. |
| 9,115,355 B2 | 8/2015 | Han et al. |
| 9,725,715 B2 | 8/2017 | Han et al. |
| 2005/0079504 A1 | 4/2005 | Amitai et al. |
| 2009/0234109 A1 | 9/2009 | Han et al. |
| 2010/0063134 A1 | 3/2010 | Kaemmerer |
| 2010/0112556 A1 | 5/2010 | Sampson et al. |
| 2011/0195848 A1 | 8/2011 | Roopra et al. |
| 2011/0288826 A1 | 11/2011 | Breaker et al. |
| 2012/0088815 A1 | 4/2012 | Liang |
| 2012/0101147 A1 | 4/2012 | Tsai et al. |
| 2013/0244327 A1 | 9/2013 | Puri et al. |
| 2013/0330725 A1 | 12/2013 | Saito et al. |
| 2015/0004615 A1 | 1/2015 | Pierce et al. |
| 2015/0065555 A1 | 3/2015 | Brown et al. |
| 2015/0284717 A1 | 10/2015 | Templin et al. |
| 2015/0315581 A1 | 11/2015 | Han et al. |
| 2016/0046934 A1 | 2/2016 | Han et al. |
| 2016/0130581 A1 | 5/2016 | Han et al. |
| 2016/0153036 A1 | 6/2016 | Chen et al. |
| 2017/0183652 A1 | 6/2017 | Thum et al. |
| 2018/0223344 A1 | 8/2018 | Chandrasekaran et al. |
| 2019/0153437 A1 | 5/2019 | Emerick et al. |
| 2020/0291396 A1 | 9/2020 | Zamore et al. |
| 2021/0019973 A1 | 1/2021 | Yin et al. |
| 2021/0032707 A1 | 2/2021 | Talasaz |
| 2021/0095286 A1 | 4/2021 | Weiss et al. |
| 2021/0123060 A1 | 4/2021 | Marcucci et al. |

FOREIGN PATENT DOCUMENTS

| | | |
|---|---|---|
| WO | 2011/163526 A2 | 12/2011 |
| WO | WO2013/075132 | 5/2013 |
| WO | 2013/142735 A1 | 9/2013 |
| WO | WO2019/014656 | 1/2019 |
| WO | 2019/033079 A1 | 2/2019 |
| WO | WO2019/033083 | 2/2019 |
| WO | WO2023/283546 | 1/2023 |
| WO | WO2023/283548 | 1/2023 |
| WO | WO2023/283550 | 1/2023 |
| WO | WO2023/283551 | 1/2023 |
| WO | WO2023/283552 | 1/2023 |
| WO | WO2023/283553 | 1/2023 |
| WO | WO2023/070057 | 4/2023 |

OTHER PUBLICATIONS

Adams, D., et al., "Patisiran, an RNAi Therapeutic, for Hereditary Transthyretin Amyloidosis," New Engl. J. Med. 379(1):11-21 (2018).
Aduri, R., et al., "AMBER Force Field Parameters for the Naturally Occurring Modified Nucleosides in Rna," J. Chem. Theory Comput. 3:1464-1475 (2007).
Benenson, Y., "Biomolecular Computing Systems: Principles, Progress and Potential," Nat. Rev. Genet. 13:455-468 (2012).
Benenson, Y., et al., "An Autonomous Molecular Computer for Logical Control of Gene Expression," Nature 429:423-429 (2004).
Bindewald, E., et al., "Multistrand Structure Prediction of Nucleic Acid Assemblies and Design of RNA Switches," Nano Lett. 16(3):1726-1735 (2016).
Bobbin, M. L., et al., "RNA Interference (RNAi)-Based Therapeutics: Delivering on the Promise?" Annu. Rev. Pharmacol. Toxicol. 56:103-122 (2016).
Bramsen, J. B., et al., "A Large-Scale Chemical Modification Screen Identifies Design Rules to Generate siRNAs with High Activity, High Stability and Low Toxicity," Nucleic Acids Research 37(9):2867-2881 (2009).
Bujold, K. E., et al., "Optimized DNA "Nanosuitcases" for Encapsulation and Conditional Release of siRNA," J. Am. Chem. Soc. 138:14030-14038 (2016).
Camacho, C., et al., "BLAST+: Architecture and Applications," BMC Bioinformatics 10:421 (2009).
Chatterjee, G., et al., "Nucleic Acid Strand Displacement with Synthetic mRNA Inputs in Living Mammalian Cells," ACS Synth. Biol. 7(12):2737-2741 (2018).
Chen, Y.J., et al., "DNA Nanotechnology from the Test Tube to the Cell," Nat. Nanotechnol. 10:748-760 (2015).
Colasanti, A. V., et al., "Analyzing and Building Nucleic Acid Structures with 3DNA," J. Vis. Exp. 74:e4401 (2013).
Collingwood, M. A., et al., "Chemical Modification Patterns Compatible with High Potency Dicer-Substrate Small Interfering RNAs," Oligonucleotides 18:187-200 (2008).
Condon, D. E., et al., "Optimization of an AMBER Force Field for the Artificial Nucleic Acid, LNA, and Benchmarking with NMR of L(CAAU)," J. Phys. Chem. B 118:1216-1228 (2014).
Duan, Y., et al., "A Point-Charge Force Field for Molecular Mechanics Simulations of Proteins Based on Condensed-Phase Quantum Mechanical Calculations," J. Comput. Chem. 24:1999-2012 (2003).
Efthymiou, T. C., et al., "Evaluation of siRNAs that Contain Internal Variable-Length Spacer Linkages," Bioorg. Med. Chem. Lett. 22:5590-5594 (2012).
Engelen, W., et al., "DNA-Based Control of Protein Activity," Chem. Commun. 52(18):3598-3610 (2016).
Glaser, S. P., et al., "Anti-Apoptotic Mcl-1 is Essential for the Development and Sustained Growth of Acute Myeloid Leukemia," Genes Dev. 26:120-125 (2012).
Glen Research, Labels and Modifiers, https://www.glenresearch.com/browse/labels-and-modifiers, downloaded Jan. 31, 2022, 7 pages.
Glen Research, Locked Analog Phosphoramidites, https://www.glenresearch.com/products/labels-and-modifiers/backbone-modification/locked-analog-phosphoramidites.html, downloaded Jan. 31, 2022, 4 pages.
Glen Research, Nucleoside Analog Phosphoramidites, https://www.glenresearch.com/browse/nucleoside-analog-phosphoramidites, downloaded Jan. 31, 2022, 4 pages.
Green, A. A., et al., "Complex Cellular Logic Computation Using Ribocomputing Devices," Nature 548(7665):117-121 (2017).
Groves, B., et al., "Computing in Mammalian Cells with Nucleic Acid Strand Exchange," Nat. Nanotechnol. 11(3):287-294 (2016).
Guo, P., "The Emerging Field of RNA Nanotechnology," Nat. Nanotechnol. 5(12):833-842 (2010).
Ha, M., et al., "Regulation of MicroRNA Biogenesis," Nat. Rev. Mol. Cell. Biol. 15:509-524 (2014).
Han, S.P., et al., "Programmable siRNA Pro-Drugs that Activate RNAi Activity in Response to Specific Cellular RNA Biomarkers," Mol. Ther. Nucl. Acids 27:797-809 (2022).
Heissig, P., et al., "DNA as Tunable Adaptor for siRNA Polyplex Stabilization and Functionalization," Mol. Ther. Nucl. Acids 5:e288 (2016).
Hochrein, L. M., et al., "Conditional Dicer Substrate Formation via Shape and Sequence Transduction with Small Conditional RNAs," J. Am. Chem. Soc. 135:17322-17330 (2013).
Hochrein, L. M., et al., "Signal Transduction in Human Cell Lysate via Dynamic RNA Nanotechnology," ACS Synth. Biol. 7:2796-2802 (2018).
IDT DNA, Oligo Modifications, https://www.idtdna.com/pages/products/custom-dna-rna/oligo-modifications, downloaded Jan. 31, 2022, 2 pages.
Iwamoto, N., et al., "Control of Phosphorothioate Stereochemistry Substantially Increases the Efficacy of Antisense Oligonucleotides," Nat. Biotechnol. 35(9):845-851 (2017).

(56) References Cited

OTHER PUBLICATIONS

Khvorova, A., et al., "The Chemical Evolution of Oligonucleotide Therapies of Clinical Utility," Nat. Biotechnol. 35(3):238-248 (2017).
Kim, D.H., et al., "Synthetic dsRNA Dicer Substrates Enhance RNAi Potency and Efficacy," Nat. Biotechnol. 23(2):222-226 (2005).
Kundu, M., et al., "Function of the inv(16) Fusion Gene CBFB-MYH11," Hematol. 8:201-205 (2001).
Kumar, D., et al., "Combinatorially Inducible RNA Interference Triggered by Chemically Modified Oligonucleotides," J. Am. Chem. Soc. 133:2783-2788 (2011).
Lee, H. Y., et al., "Differential Roles of Human Dicer-Binding Proteins TRBP and PACT in Small RNA Processing," Nucleic Acids Research 41(13):6568-6576 (2013).
Lennox, K. A., et al., "Improved Performance of Anti-miRNA Oligonucleotides Using a Novel Non-Nucleotide Modifier," Mol. Ther. Nucl. Acids 2:e117 (2013).
Li, X., et al., "Antiparallel DNA Double Crossover Molecules as Components for Nanoconstruction," J. Am. Chem. Soc. 118:6131-6140 (1996).
Lind, K. E., et al., "Parameterization and Simulation of the Physical Properties of Phosphorothioate Nucleic Acids," Am. Chem. Soc. 3:41-54 (1998).
Look, A. T., "Oncogenic Transcription Factors in the Human Acute Leukemias," Science 278:1059-1064 (1997).
Macke, T. J., et al., "Modeling Unusual Nucleic Acid Structures," ACS Symposium Series, Am. Chem. Soc. 24:379-393 (1998).
Macrae, I. J., et al., "Structural Basis for Double-Stranded RNA Processing by Dicer," Science 311:195-198 (2006).
Mark, P., et al., "Structure and Dynamics of the TIP3P, SPC, and SPC/E Water Models at 298 K.," J. Phys. Chem. A 105:9954-9960 (2001).
Mathews, D. H., et al., "Expanded Sequence Dependence of Thermodynamic Parameters Improves Prediction of RNA Secondary Structure," J. Mol. Biol. 288:911-940 (1999).
Mathy, N., et al., "5'-to-3' Exoribonuclease Activity in Bacteria: Role of RNase J1 in rRNA Maturation and 5' Stability of mRNA," Cell 129:681-692 (2007).
Matsukura, M., et al., "Phosphorothioate Analogs of Oligodeoxynucleotides: Inhibitors of Replication and Cytopathic Effects of Human Immunodeficiency Virus," Proc. Natl. Acad. Sci. USA 84:7706-7710 (1987).
Meggers, E., et al., "Synthesis and Properties of the Simplified Nucleic Acid Glycol Nucleic Acid," Accounts of Chem. Res. 43(8):1092-1102 (2010).
Mukherjee, P., et al., "Design of a DNA-Programmed Plasminogen Activator," J. Am. Chem. Soc. 140(45):15516-15524 (2018).
Orban, T. I., et al., "Decay of mRNAs Targeted by RISC Requires XRN1, the Ski Complex, and the Exosome," RNA 11:459-469 (2005).
Pettersen, E. F., et al., "UCSF Chimera—A Visualization System for Exploratory Research and Analysis," J. Comput. Chem. 25:1605-1612 (2004).
Plimpton, S., "Fast Parallel Algorithms for Short-Range Molecular Dynamics," J. Comput. Phys. 117:1-19 (1995).
Scherer, L. J., et al., "Optimization and Characterization of tRNA-shRNA Expression Constructs," Nucleic Acids Research 35(8):2620-2628 (2007).
Schlegel, M. K., et al., "Chirality Dependent Potency Enhancement and Structural Impact of Glycol Nucleic Acid Modification on siRNA," J. Am. Chem. Soc. 139:8537-8546 (2017).
Seeman, N. C., "DNA in a Material World," Nature 421:427-431 (2003).
Setten, R. L., et al., "The Current State and Future Directions of RNAi-Based Therapeutics," Nat. Rev. Drug Discov. 18:421-446 (2019).
Shu, D., et al., "Thermodynamically Stable RNA Three-Way Junction for Constructing Multifunctional Nanoparticles for Delivery of Therapeutics," Nat. Nanotechnol. 6:658-667 (2011).
Silverman, S. K., "Control of Macromolecular Structure and Function Using Covalently Attached Double-Stranded DNA Constraints," Mol. BioSyst. 3:24-29 (2007).
Srinivas, N., et al., "On the Biophysics and Kinetics of Toehold-Mediated DNA Strand Displacement," Nucleic Acids Research 41(22):10641-10658 (2013).
Tolstrup, N., et al., "OligoDesign: Optimal Design of LNA (Locked Nucleic Acid) Oligonucleotide Capture Probes for Gene Expression Profiling," Nucleic Acids Research 31(13):3758-3762 (2003).
United States Patent and Trademark Office, International Search Report and Written Opinion dated Nov. 25, 2019 for PCT/US19/46075, 9 pages.
Wang, J., et al., "Development and Testing of a General Amber Force Field," J. Comput. Chem. 25:1157-1174 (2004).
Wikipedia, Locked Nucleic Acid, https://en.wikipedia.org/wiki/Locked_nucleic_acid, downloaded Jan. 31, 2022, 5 pages.
Yang, X.C., et al., "Studies of the 59 Exonuclease and Endonuclease Activities of CPSF-73 in Histone Pre-mRNA Processing," Mol. Cell. Biol. 29(1):31-42 (2009).
Yurke, B., et al., "A DNA-Fuelled Molecular Machine Made of DNA," Nature 406:605-608 (2000).
Zadeh, J. N., et al., "Software News and Updates: NUPACK: Analysis and Design of Nucleic Acid Systems," J. Comput. Chem. 32:170-173 (2011).
Zhou, J., et al., "Selection, Characterization and Application of New RNA HIV gp 120 Aptamers for Facile Delivery of Dicer Substrate siRNAs into HIV Infected Cells," Nucleic Acids Research 37(9):3094-3109 (2009).
European Patent Office, Extended European Search Report and Opinion dated Apr. 14, 2022 for European Patent Application No. 19846651.8, 10 pages.
U.S. Appl. No. 63/172,030, filed Apr. 7, 2021, Han et al.
U.S. Appl. No. 63/218,862, filed Jul. 6, 2021, Si-ping Han.
U.S. Appl. No. 63/218,833, filed Jul. 6, 2021, Han et al.
U.S. Appl. No. 63/218,850, filed Jul. 6, 2021, Han et al.
U.S. Appl. No. 63/218,865, filed Jul. 6, 2021, Si-ping Han.
Afonin et al., "Design and self-assembly of siRNA-functionalized RNA nanoparticles for use in automated nanomedicine," Nature Protocols 2011, 6, 2022-2034.
American Cancer Society, "Key Statistics for Acute Myeloid Leukemia (AML)," cancer.org 2023, in 10 pages. https://www.cancer.org/cancer/types/acute-myeloid-leukemia/about/key-statistics.html.
Avino et al., "Oligonucleotide-peptide conjugates: solid-phase synthesis under acidic conditions and use in ELISA assays," Molecules 2012, 17, 13825-13843.
Beta Lab, "RNAsoft—Software for RNA/DNA secondary structure prediction and design," University of British Columbia 2023, in 1 page. http://www.rnasoft.ca/.
Bhatia et al., "A synthetic icosahedral DNA-based host-cargo complex for functional in vivo imaging," Nature Communications 2011, 2, in 8 pages.
Boudreau et al., "Rational Design of Therapeutic siRNAs: Minimizing Off-targeting Potential to Improve the Safety of RNAi Therapy for Huntington's Disease," Molecular Therapy 2011, 19(12), 2169-2177.
Cao et al., "Histone deacetylase (HDAC) inhibitors attenuate cardiac hypertrophy by suppressing autophagy," Proceedings of the National Academy of Sciences 2011, 108, 4123-4128.
Chojnowski et al., "RNA Bricks—a database of Rna 3D motifs and their interactions," Nucleic Acids Research 2014, 42, D123-D121.
Dirks et al., "A partition function algorithm for nucleic acid secondary structure including pseudoknots," Journal of Computational Chemistry 2003, 24, 1664-1677.
Dirks et al., "An algorithm for computing nucleic acid base-pairing probabilities including pseudoknots," Journal of Computational Chemistry 2004, 25, 1295-1304.
Dirks et al., "Paradigms for computational nucleic acid design," Nucleic Acids Research 2004, 32, 1392-1403.
Dirks et al., "Thermodynamic analysis of interacting nucleic acid strands," SIAM Review 2007, 49, 65-88.
Dowdy, "Overcoming cellular barriers for RNA therapeutics," Nature Biotechnology 2017, 35(3), 222-229.

(56) References Cited

OTHER PUBLICATIONS

Dresselhaus & Meffert, "Cellular specificity of NF-κB function in the nervous system," Frontiers in Immunology 2019, 10, in 14 pages.
Duda et al., "Targeting GSK3 signaling as a potential therapy of neurodegenerative diseases and aging," Expert Opinion on Therapeutic Targets 2018, 22(10), 833-848.
Estey, "Acute Myeloid Leukemia: 2012 Update on Diagnosis, Risk Stratification, and Management," American Journal of Hematology 2012, 87(1), 89-99.
Exiqon, "LNA™ Oligo Tools and Design Guidelines," exiqon.com 2020, in 1 page. www.exiqon.com/oligo-tools.
Filipi et al., "Glial cells—The strategic targets in amyotrophic lateral sclerosis treatment," Journal of Clinical Medicine 2020, 9(1), in 47 pages.
First Office Action dated Feb. 27, 2023 in Chinese Patent Application No. 201880066486.5.
Fleige et al., "Stimuli-responsive polymeric nanocarriers for the controlled transport of active compounds: Concepts and applications," Advanced Drug Delivery Reviews 2012, 64(9), 866-884.
Gawande et al., "Selection of DNA aptamers with two modified bases," Proceedings of the National Academy of Sciences 2017, 114, 2898-2903.
Glen Research, "Locked Analog Phosphoramidites and Supports," Glenresearch.com 2023, in 4 pages. https://www.glenresearch.com/products/labels-and-modifiers/backbone-modification/locked-analog-phosphoramidites.html.
Glen Research, "Modification and Labeling," glenresearch.com 2023, in 6 pages. www.glenresearch.com/browse/labels-and-modifiers.
Graham et al., "Isolation, Culture, and Functional Characterization of Adult Mouse Cardiomyocytes," JoVE 2013, 79, in 13 pages.
Green et al., "To kill a microglia: a case for CSF1R inhibitors," Trends in Immunology 2020, 41(9), 771-784.
GSRS, "Casimersen," nih.gov 2023, in 1 page. https://gsrs.ncats.nih.gov/ginas/app/beta/substances/905e0f05-b9c5-412c-a0e1-5bb898111944.
GSRS, "Eteplirsen," nih.gov 2023, in 1 page. https://gsrs.ncats.nih.gov/ginas/app/beta/substances/4d0cddf7-f088-45af-af78-27659898e442.
GSRS, "Golodirsen," nih.gov 2023, in 1 page. https://gsrs.ncats.nih.gov/ginas/app/beta/substances/e54505d8-4af5-43f6-95b4-f70effe0b457.
Guttenplan et al., "Knockout of reactive astrocyte activating factors slows disease progression in an ALS mouse model," Nature Communications 2020, 11(1), in 9 pages.
Hammond et al., "Delivery of oligonucleotide-based therapeutics: challenges and opportunities," EMBO Molecular Medicine 2021, 13(4), e13243.
Hartmann et al., "Effects of phenylephrine on calcium current and contractility of feline ventricular myocytes," American Journal of Physiology-Heart and Circulatory Physiology 1988, 255, H1173-H1180.
Hill et al., "Sonic hedgehog signaling in astrocytes," Cellular and Molecular Life Sciences 2021, 78, 1393-1403.
Hope & Trono, "Structure, Expression, and Regulation of the HIV Genome," HIV In Site 2020, in 11 pages. http://hivinsite.ucsf.edu/InSite?page=kb-OO&doc=kb-02-1-02.
Horizon, "Dharmacon reagents," horizondiscovery.com 2023, in 8 pages. http://dharmacon.horizondiscovery.com/design-center/.
Hu et al., "Therapeutic siRNA: state of the art," Signal Transduction and Targeted Therapy 2020, 5(1), in 25 pages.
Huang et al., "Activation of Wnt/β-catenin signalling via GSK3 inhibitors direct differentiation of human adipose stem cells into functional hepatocytes," Scientific Reports 2017, 7(1), in 12 pages.
International Search Report and Written Opinion dated Jan. 4, 2019 in PCT Patent Application No. PCT/US2018/046383.
International Search Report and Written Opinion dated Jan. 25, 2023 in PCT Patent Application No. PCT/US2022/078466.
International Search Report and Written Opinion dated Nov. 26, 2018 in PCT Patent Application No. PCT/US2018/046379.
International Search Report and Written Opinion dated Oct. 4, 2022 in PCT Patent Application No. PCT/US2022/073426.
International Search Report and Written Opinion dated Oct. 27, 2022 in PCT Patent Application No. PCT/US2022/073432.
International Search Report and Written Opinion dated Sep. 14, 2022 in PCT Patent Application No. PCT/US2022/073430.
International Search Report and Written Opinion dated Sep. 23, 2022 in PCT Patent Application No. PCT/US2022/073428.
International Search Report and Written Opinion dated Sep. 28, 2022 in PCT Patent Application No. PCT/US2022/073431.
International Search Report and Written Opinion dated Sep. 20, 2018 in PCT Patent Application No. PCT/US2018/042195.
International Search Report and Written Opinion dated Sep. 28, 2022 in PCT Patent Application No. PCT/US2022/073433.
Jafar-Nejad et al., "The atlas of RNase H antisense oligonucleotide distribution and activity in the CNS of rodents and non-human primates following central administration," Nucleic Acids Research 2021, 49(2), 657-673.
Japanese Office Action dated Jul. 4, 2023 in Japanese Patent Application No. 2021531622.
Japanese Search Report dated Jun. 23, 2023 in Japanese Patent Application No. 2021531622.
Jaramillo-Botero et al., "First-principles-based multiscale, multiparadigm molecular mechanics and dynamics methods for describing complex chemical processes," Multiscale Molecular Methods in Applied Chemistry 2012, 1-42.
Jessup & Brozena, "Heart Failure," New England Journal of Medicine 2003, 348, 2007-2018.
Joe et al., "Astrocytes, microglia, and Parkinson's disease," Experimental Neurobiology 2018, 27(2), 77-87.
Kadkol et al., "Comprehensive Analysis of CBFbeta-MYH11 Fusion Transcripts in Acute Myeloid Leukemia by RT-PCR Analysis," The Journal of Molecular Diagnostics 2004, 6(1), 22-27.
Katanosaka et al., "Calcineurin Inhibits Na+/Ca2+ Exchange in Phenylephrine-treated Hypertrophic Cardiomyocytes," Journal of Biological Chemistry 2005, 280, 5764-5772.
Keum et al., "Design, assembly, and activity of antisense DNA nanostructures," Small 2011, 7(24), 3529-3535.
Knerr et al. "Glucagon like peptide 1 receptor agonists for targeted delivery of antisense oligonucleotides to pancreatic beta cell," Journal of the American Chemical Society 2021, 143(9), 3416-3429.
Konstam et al., "Left ventricular remodeling in heart failure: current concepts in clinical significance and assessment," JACC Cardiovasc Imaging 2011, 4(1), 98-108.
Landry et al., "Progress in RNAi-Mediated Molecular Therapy of Acute and Chronic Myeloid Leukemia," Molecular Therapy—Nucleic Acids 2015, 4, in 23 pages.
Lee et al., "Molecularly self-assembled nucleic acid nanoparticles for targeted in vivo siRNA delivery," Nature Nanotechnology 2012, 7, 389-393.
Liu et al., "miR-222 Is Necessary for Exercise-Induced Cardiac Growth and Protects against Pathological Cardiac Remodeling," Cell Metabolism 2015, 21, 584-595.
Loakes, "Survey and summary: The applications of universal DNA base analogues," Nucleic Acids Research 2001, 29(12), 2437-2447.
Lu et al., "Linkers having a crucial role in antibody-drug conjugates," International Journal of Molecular Sciences 2016, 17, 561.
Lutgen et al., "β-Catenin signaling positively regulates glutamate uptake and metabolism in astrocytes," Journal of Neuroinflammation 2016, 13, 1-13.
Marks et al., "Histone deacetylases and cancer: causes and therapies," Nature Reviews Cancer 2001, 1(3), 194.
Mathews Lab, "Rna structure, Version 6.4," rochester.edu 2023, in 1 page. http://rna.urmc.rochester.edu/RNAstructure.html.
Millipore Sigma, "Locked Nucleic Acid," sigmaaldrich.com 2023, in 5 pages. www.sigmaaldrich.com/technical-documents/articles/biology/locked-nucleic-acids-faq.html.
Mirbase, "Stem-loop sequence hsa-mir-23a," mirbase.org 2023, in 3 pages. https://www.mirbase.org/cgi-bin/mirna_entry.pl?acc=MI0000079.
Molkentin et al., "Calcineurin-Dependent Transcriptional Pathway for Cardiac Hypertrophy," Cell 1998, 93, 215-228.

(56) References Cited

OTHER PUBLICATIONS

Morel et al., "Neuronal exosomal miRNA-dependent translational regulation of astroglial glutamate transporter GLT1," Journal of Biological Chemistry 2013, 288(10), 7105-7116.
Naito & Kumiko, "Designing functional siRNA with reduced off-target effects," siRNA Design: Methods and Protocols 2013, 57-68.
Nearest Neighbor Database, "Introduction and Definitions," rochester.edu 2023, in 4 pages. https://rna.urmc.rochester.edu/NNDB/help.html.
Nearest Neighbor Database, "Version 1.02, Released Apr. 4, 2011," rochester.edu 2023, in 3 pages. https://rna.urmc.rochester.edu/NNDB/index.html.
Nolan et al., "Quantification of mRNA using real-time RT-PCR," Nature Protocols 2006, 1(3), 1559-1582.
Non-Final Office Action dated Dec. 24, 2021 in U.S. Appl. No. 16/786,793.
Non-Final Office Action dated Jun. 23, 2022 in U.S. Appl. No. 16/786,793.
Notice of Allowance dated Jan. 12, 2023 in U.S. Appl. No. 16/786,793.
Opferman et al., "Obligate Role of Anti-Apoptotic MCL-1 in the Survival of Hematopoietic Stem Cells," Science 2005, 307(5712), 1101-1104.
Owczarzy et al., "IDT SciTools: a suite for analysis and design of nucleic acid oligomers," Nucleic Acids Research 2008, 36(suppl_2), W163-W169.
Pajarillo et al., "Astrocyte-specific deletion of the transcription factor Yin Yang 1 in murine substantia nigra mitigates manganese-induced dopaminergic neurotoxicity," Journal of Biological Chemistry 2020, 295(46), 15662-15676.
Paradis et al., "Newborn Hypoxia/Anoxia Inhibits Cardiomyocyte Proliferation and Decreases Cardiomyocyte Endowment in the Developing Heart: Role of Endothelin-1," PLOS One 2015, 10, in 21 pages.
Pi et al., "RNA nanoparticles harboring annexin A2 aptamer can target ovarian cancer for tumor-specific doxorubicin delivery," Nanomedicine 2017, 13(3), 1183-1193.
Picco & Garnett, "A Road Map for Precision Cancer Medicine Using Personalized Models," Cancer Discovery 2017, 7(5), 456-458.
Qi et al., "HDAC8 Inhibition Specifically Targets Inv(16) Acute Myeloid Leukemic Stem Cells by Restoring p53 Acetylation," Cell Stem Cell 2015, 17(5), 597-610.
Qiagen, "LNA Oligo Optimizer," qiagen.com 2020, in 1 page. https://www.qiagen.com/us/service-and-support/learning-hub/technologies-and-research-topics/lna/custom-lna-design-and-applications/lna-design-tools-calculators/lna-oligo-optimizer/.
Qiagen, "Tm Predication," qiagen.com 2020, in 1 page. https://www.qiagen.com/us/service-and-support/learning-hub/technologies-and-research-topics/lna/custom-lna-design-and-applications/lna-design-tools-calculators/lna-oligo-tm-prediction/.
Red Server, "RESP ESP charge Derive server," q4md-forcefieldtools.org 2023, in 2 pages. q4md-forcefieldtools.org/REDServer/.
Restriction Requirement dated Apr. 30, 2021 in U.S. Appl. No. 16/786,793.
Restriction Requirement dated Aug. 3, 2023 in U.S. Appl. No. 16/631,134.
Restriction Requirement dated May 23, 2023 in U.S. Appl. No. 16/638,107.
Rij, "Virus meets RNAi. Symposium on Antiviral Applications of RNA Interference," EMBO Reports 2008, 9(8), 725-729.
Robinson et al., "Integrative clinical genomics of metastatic cancer," Nature 2017, 548(7667), 297-303.
Rojo et al., "GSK-3β down-regulates the transcription factor Nrf2 after oxidant damage: relevance to exposure of neuronal cells to oxidative stress," Journal of Neurochemistry 2008, 105(1), 192-202.
Rothemund, "Folding DNA to create nanoscale shapes and patterns," Nature 2006, 440 (7082), 297-302.
Sabir et al., "Branchpoint expansion in a fully complementary three-way DNA junction," Journal of the American Chemical Society 2012, 134(14), 6280-6285.
Sano et al., "Effect of asymmetric terminal structures of short RNA duplexes on the RNA interference activity and strand selection," Nucleic Acids Research 2008, 36, 5812-5821.
Second Office Action dated Sep. 20, 2023 in Chinese Patent Application No. 201880066486.5.
Shu et al., "Programmable folding of fusion RNA in vivo and in vitro driven by pRNA 3WJ motif of phi29 DNA packaging motor," Nucleic Acids Research 2014, 42(2), in 9 pages.
Shukla et al., "Exploring Chemical Modifications for siRNA Therapeutics: A Structural and Functional Outlook," ChemMedChem 2010, 5, 328-349.
Srinivasan et al., "Alzheimer's patient microglia exhibit enhanced aging and unique transcriptional activation," Cell Reports 2020, 31(13), in 20 pages.
Supplementary European Search Report and European Search Opinion dated Apr. 8, 2021 in European Patent Application No. 18844244.6.
Sussman et al., "Prevention of Cardiac Hypertrophy in Mice by Calcineurin Inhibition," Science 1998, 281, 1690-1693.
Tham et al., "Pathophysiology of cardiac hypertrophy and heart failure: signaling pathways and novel therapeutic targets," Archives of Toxicology 2015, 89, 1401-1438.
The Nupack Team, "Nupack Cloud Alpha," nupack.org 2023, in 1 page. http://nupack.org.
Theoretical Biochemistry Group, "The ViennaRNA Package," Universitat Wien 2023, in 7 pages. https://www.tbi.univie.ac.at/RNA/.
Trivedi et al., "Hdac2 regulates the cardiac hypertrophic response by modulating Gsk3J3 activity," Nature Medicine 2007, 13, 324-331.
Turner & Mathews, "NNDB: the nearest neighbor parameter database for predicting stability of nucleic acid secondary structure," Nucleic Acids Research 2010, 38(suppl_1), D280-D282.
VARGAS & JOHNSON, "The Nrf2-ARE cytoprotective pathway in astrocytes," Expert Reviews in Molecular Medicine 2009, 11, in 20 pages.
Verma & Eckstein, "Modified oligonucleotides: synthesis and strategy for users," Annual Review of Biochemistry 1998, 67(1), 99-134.
Walsh et al., "DNA cage delivery to mammalian cells," ACS Nano 2011, 5(7), 5427-5432.
Wolfe et al., "Constrained multistate sequence design for nucleic acid reaction pathway engineering," Journal of the American Chemical Society 2017, 139, 3134-3144.
Wolfe et al., "Sequence design for a test tube of interacting nucleic acid strands," ACS Synthetic Biology 2015, 4, 1086-1100.
Xiao et al., "miR-31a-5p promotes postnatal cardiomyocyte proliferation by targeting RhoBTB1," Experimental & Molecular Medicine 2017, 49, in 10 pages.
Zadeh et al., "Nucleic acid sequence design via efficient ensemble defect optimization," Journal of Computational Chemistry 2011, 32, 439-452.
Zhang et al., "Mcl-1 is Critical for Survival in a Subgroup of Non-Small-Cell Lung Cancer Cell Lines," Oncogene 2011, 30, 1963-1968.
Zhang et al., "Structural DNA nanotechnology: state of the art and future perspective," Journal of the American Chemical Society 2014, 136(32), 11198-111211.

Figure 1B
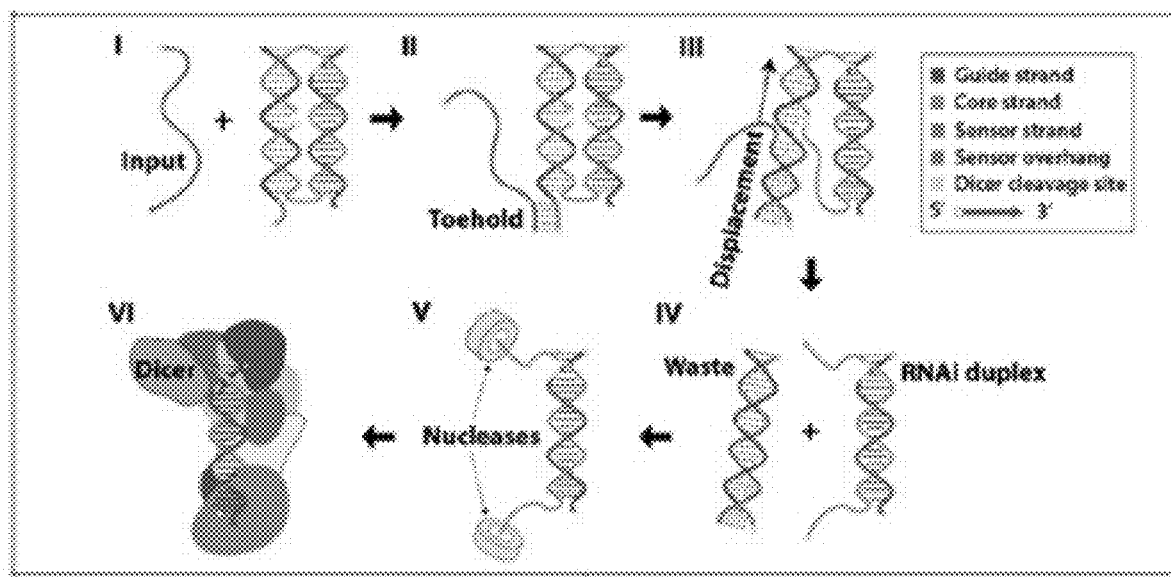
Figure 1C
Figure 1D
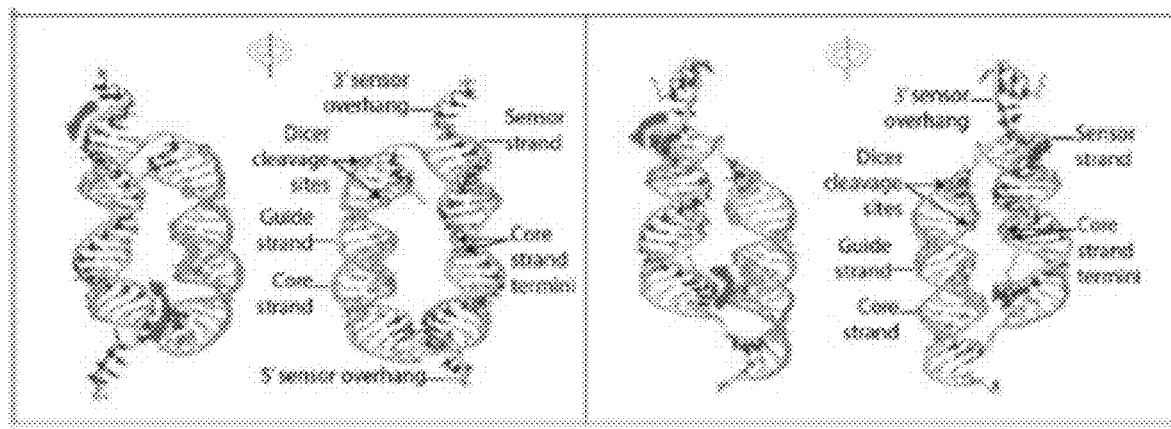

Construct III.1

Input: *CBFB-MYH11*
Target: *HIV 5' utr*

Regions for screening of chemical modifications

- A — Nick in sensor duplex
- B
- C
- D

+A, +T, +C, +G = LNA; mA, mU, mC, mG = 2'-OMe; rA, rU, rC, rG = RNA; NH2 = primary amine linker
* = phosphorothioate; . = phosphodiester; C3 = C3 spacer; Sp9 = triethylene glycol; ǂ = Dicer cleavage site

Construct IV.1

Input: *CBFB-MYH11*
Target: *MCL-1*

Sensor strand

Core strand

Guide strand

Construct IV.2

Sensor strand with 2'-OMe and LNA but no P5 in duplex region

Core strand termini protected by alternating 2'-OMe

LNA mod added

Sensor strand

Core strand

Guide strand

Figure 5H
Figure 5G
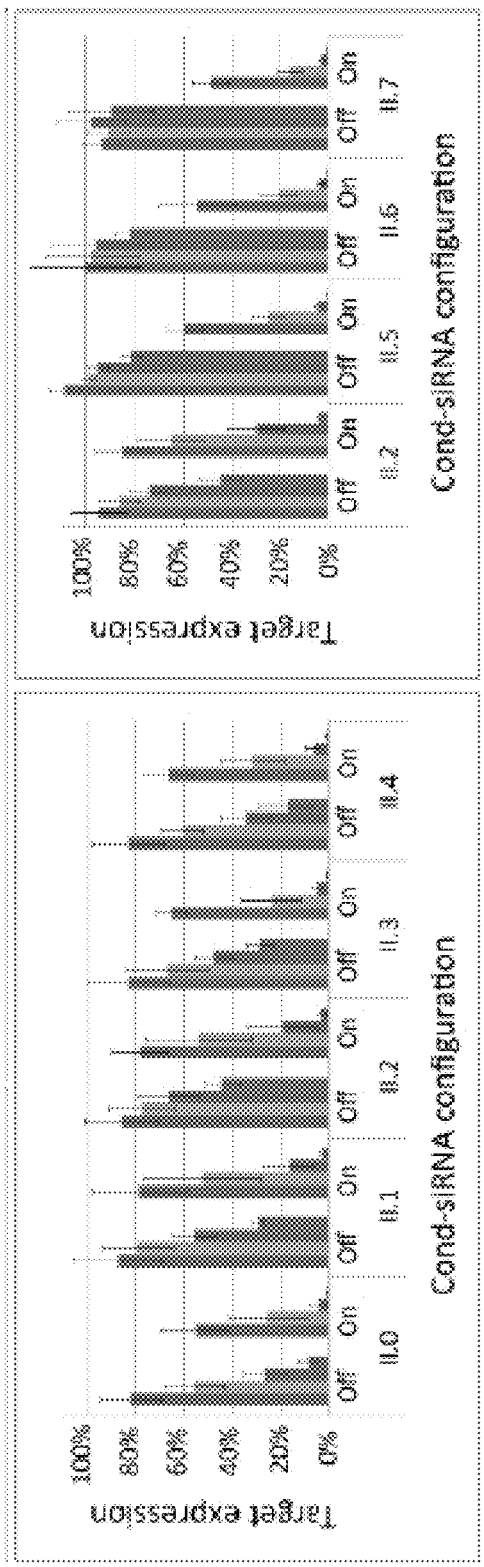
Figure 5J
Figure 5I
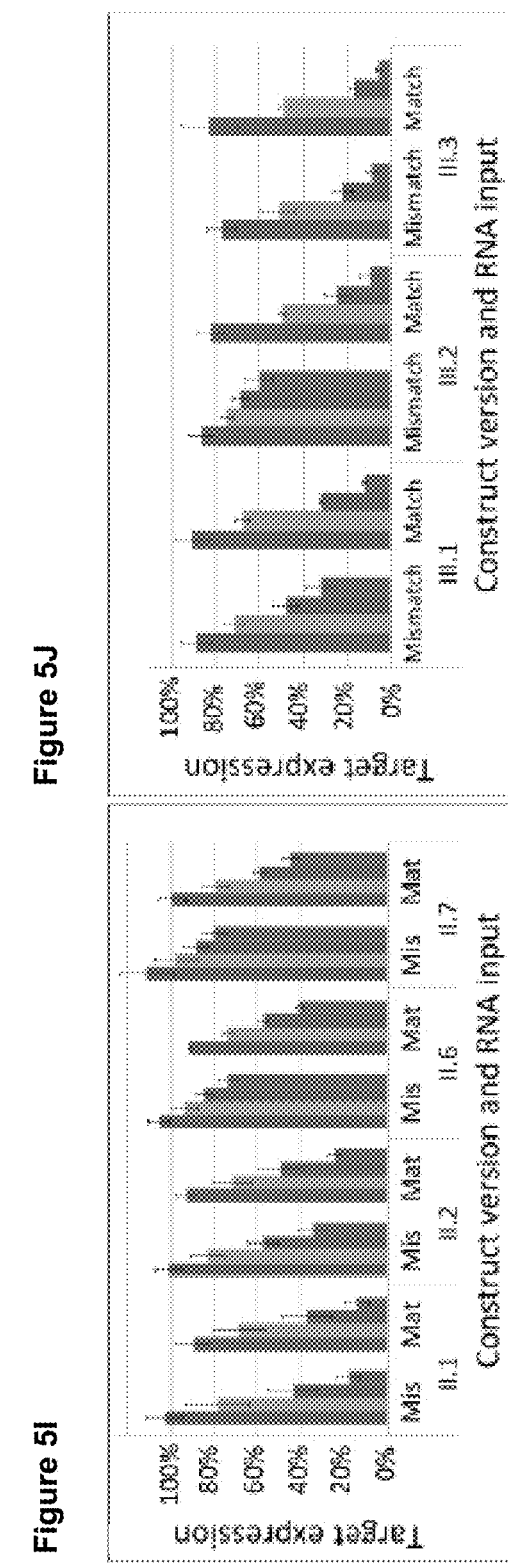

Figure 10a
Figure 10b
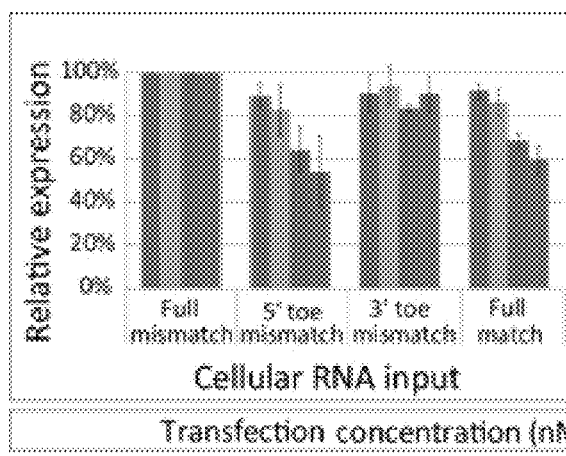
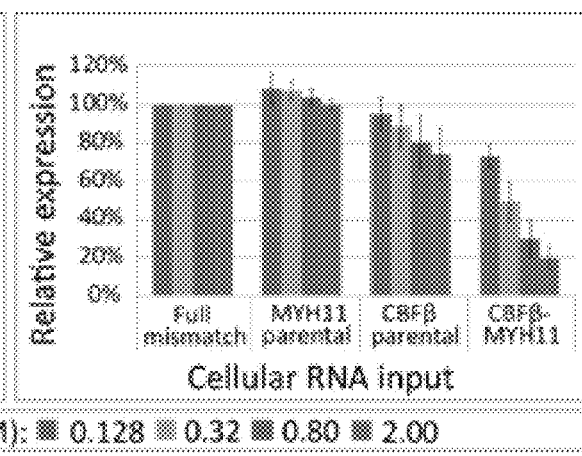

SEQUENCE LISTING

<160> NUMBER OF SEQ ID NOS: 113

<210> SEQ ID NO 1
<211> LENGTH: 33
<212> TYPE: DNA
<213> ORGANISM: Artificial Sequence
<220> FEATURE:
<223> OTHER INFORMATION: Synthetic

<400> SEQUENCE: 1
ctcuucgtcg ctguctccgc utcuuccugc cat                          33

<210> SEQ ID NO 2
<211> LENGTH: 46
<212> TYPE: RNA
<213> ORGANISM: Artificial Sequence
<220> FEATURE:
<223> OTHER INFORMATION: Synthetic

<400> SEQUENCE: 2
gagacagcga cggguaacua gagaucccuc agacgaggaa gaagcg            46

<210> SEQ ID NO 3
<211> LENGTH: 25
<212> TYPE: RNA
<213> ORGANISM: Artificial Sequence
<220> FEATURE:
<223> OTHER INFORMATION: Synthetic

<400> SEQUENCE: 3
cgucugaggg aucucuaguu accuu                                   25

<210> SEQ ID NO 4
<211> LENGTH: 31
<212> TYPE: DNA
<213> ORGANISM: Artificial Sequence
<220> FEATURE:
<223> OTHER INFORMATION: Synthetic

<400> SEQUENCE: 4
ctcuucgtcg ctguctccgc utcuuccugc c                            31

<210> SEQ ID NO 5
<211> LENGTH: 46
<212> TYPE: RNA
<213> ORGANISM: Artificial Sequence
<220> FEATURE:
<223> OTHER INFORMATION: Synthetic

<400> SEQUENCE: 5
gcggagacag cggguaacua gagaucccuc agacgggcag gaagaa            46

<210> SEQ ID NO 6
<211> LENGTH: 25
<212> TYPE: RNA
<213> ORGANISM: Artificial Sequence
<220> FEATURE:
<223> OTHER INFORMATION: Synthetic

<400> SEQUENCE: 6
cgucugaggg aucucuaguu accuu                                   25

<210> SEQ ID NO 7
<211> LENGTH: 31
<212> TYPE: DNA
<213> ORGANISM: Artificial Sequence
<220> FEATURE:
<223> OTHER INFORMATION: Synthetic

<400> SEQUENCE: 7
gacutctcca gcucauggac ctccauuucc t        31

<210> SEQ ID NO 8
<211> LENGTH: 46
<212> TYPE: RNA
<213> ORGANISM: Artificial Sequence
<220> FEATURE:
<223> OTHER INFORMATION: Synthetic

<400> SEQUENCE: 8
gcuggugaag ucgguaacua gagaucccuc agacggaggu ccauga        46

<210> SEQ ID NO 9
<211> LENGTH: 25
<212> TYPE: RNA
<213> ORGANISM: Artificial Sequence
<220> FEATURE:
<223> OTHER INFORMATION: Synthetic

<400> SEQUENCE: 9
cgucugaggg aucucuaguu accuu        25

<210> SEQ ID NO 10
<211> LENGTH: 31
<212> TYPE: DNA
<213> ORGANISM: Artificial Sequence
<220> FEATURE:
<223> OTHER INFORMATION: Synthetic

<400> SEQUENCE: 10
gacutctcca gcucauggac ctccauuucc t        31

<210> SEQ ID NO 11
<211> LENGTH: 46
<212> TYPE: RNA
<213> ORGANISM: Artificial Sequence
<220> FEATURE:
<223> OTHER INFORMATION: Synthetic

<400> SEQUENCE: 11
gcuggugaag ucgguaacua gagaucccuc agacggaggu ccauga        46

<210> SEQ ID NO 12
<211> LENGTH: 25
<212> TYPE: RNA
<213> ORGANISM: Artificial Sequence
<220> FEATURE:
<223> OTHER INFORMATION: Synthetic

<400> SEQUENCE: 12
cgucugaggg aucucuaguu accuu        25

<210> SEQ ID NO 13
<211> LENGTH: 31
<212> TYPE: DNA
<213> ORGANISM: Artificial Sequence
<220> FEATURE:
<223> OTHER INFORMATION: Synthetic

<400> SEQUENCE: 13
ctcuucgtcg ctguctccgc utcuuccugc c        31

<210> SEQ ID NO 14
<211> LENGTH: 46
<212> TYPE: RNA
<213> ORGANISM: Artificial Sequence
<220> FEATURE:
<223> OTHER INFORMATION: Synthetic

<400> SEQUENCE: 14
gcggagacag cggguaacua gagaucccuc agacgggcag gaagaa          46

<210> SEQ ID NO 15
<211> LENGTH: 25
<212> TYPE: RNA
<213> ORGANISM: Artificial Sequence
<220> FEATURE:
<223> OTHER INFORMATION: Synthetic

<400> SEQUENCE: 15
cgucugaggg aucucuaguu accuu          25

<210> SEQ ID NO 16
<211> LENGTH: 31
<212> TYPE: DNA
<213> ORGANISM: Artificial Sequence
<220> FEATURE:
<223> OTHER INFORMATION: Synthetic

<400> SEQUENCE: 16
ctcuucgtcg ctguctccgc utcuuccugc c          31

<210> SEQ ID NO 17
<211> LENGTH: 46
<212> TYPE: RNA
<213> ORGANISM: Artificial Sequence
<220> FEATURE:
<223> OTHER INFORMATION: Synthetic

<400> SEQUENCE: 17
gcggagacag cggguaacua gagaucccuc agacgggcag gaagaa          46

<210> SEQ ID NO 18
<211> LENGTH: 25
<212> TYPE: RNA
<213> ORGANISM: Artificial Sequence
<220> FEATURE:
<223> OTHER INFORMATION: Synthetic

<400> SEQUENCE: 18
cgucugaggg aucucuaguu accuu          25

<210> SEQ ID NO 19
<211> LENGTH: 31
<212> TYPE: DNA
<213> ORGANISM: Artificial Sequence
<220> FEATURE:
<223> OTHER INFORMATION: Synthetic

<400> SEQUENCE: 19
ctcuucgtcg ctguctccgc utcuuccugc c          31

<210> SEQ ID NO 20
<211> LENGTH: 46
<212> TYPE: RNA
<213> ORGANISM: Artificial Sequence
<220> FEATURE:
<223> OTHER INFORMATION: Synthetic

<400> SEQUENCE: 20
gcggagacag cggguaacua gagaucccuc agacgggcag gaagaa                    46

<210> SEQ ID NO 21
<211> LENGTH: 25
<212> TYPE: RNA
<213> ORGANISM: Artificial Sequence
<220> FEATURE:
<223> OTHER INFORMATION: Synthetic

<400> SEQUENCE: 21
cgucugaggg aucucuaguu accuu                                           25

<210> SEQ ID NO 22
<211> LENGTH: 31
<212> TYPE: DNA
<213> ORGANISM: Artificial Sequence
<220> FEATURE:
<223> OTHER INFORMATION: Synthetic

<400> SEQUENCE: 22
ctcuucgtcg ctguctccgc utcuuccugc c                                    31

<210> SEQ ID NO 23
<211> LENGTH: 46
<212> TYPE: RNA
<213> ORGANISM: Artificial Sequence
<220> FEATURE:
<223> OTHER INFORMATION: Synthetic

<400> SEQUENCE: 23
gcggagacag cggguaacua gagaucccuc agacgggcag gaagaa                    46

<210> SEQ ID NO 24
<211> LENGTH: 25
<212> TYPE: RNA
<213> ORGANISM: Artificial Sequence
<220> FEATURE:
<223> OTHER INFORMATION: Synthetic

<400> SEQUENCE: 24
cgucugaggg aucucuaguu accuu                                           25

<210> SEQ ID NO 25
<211> LENGTH: 31
<212> TYPE: DNA
<213> ORGANISM: Artificial Sequence
<220> FEATURE:
<223> OTHER INFORMATION: Synthetic

<400> SEQUENCE: 25
ctcuucgtcg ctguctccgc utcuuccugc c                                    31

<210> SEQ ID NO 26
<211> LENGTH: 46
<212> TYPE: RNA
<213> ORGANISM: Artificial Sequence
<220> FEATURE:
<223> OTHER INFORMATION: Synthetic

<400> SEQUENCE: 26
gcggagacag cggguaacua gagaucccuc agacgggcag gaagaa                    46

<210> SEQ ID NO 27

<211> LENGTH: 25
<212> TYPE: RNA
<213> ORGANISM: Artificial Sequence
<220> FEATURE:
<223> OTHER INFORMATION: Synthetic

<400> SEQUENCE: 27
cgucugaggg aucucuaguu accuu                                             25

<210> SEQ ID NO 28
<211> LENGTH: 31
<212> TYPE: DNA
<213> ORGANISM: Artificial Sequence
<220> FEATURE:
<223> OTHER INFORMATION: Synthetic

<400> SEQUENCE: 28
ctcuucgtcg ctguctccgc utcuuccugc c                                      31

<210> SEQ ID NO 29
<211> LENGTH: 46
<212> TYPE: RNA
<213> ORGANISM: Artificial Sequence
<220> FEATURE:
<223> OTHER INFORMATION: Synthetic

<400> SEQUENCE: 29
gcggagacag cggguaacua gagaucccuc agacgggcag gaagaa                      46

<210> SEQ ID NO 30
<211> LENGTH: 25
<212> TYPE: RNA
<213> ORGANISM: Artificial Sequence
<220> FEATURE:
<223> OTHER INFORMATION: Synthetic

<400> SEQUENCE: 30
cgucugaggg aucucuaguu accuu                                             25

<210> SEQ ID NO 31
<211> LENGTH: 31
<212> TYPE: DNA
<213> ORGANISM: Artificial Sequence
<220> FEATURE:
<223> OTHER INFORMATION: Synthetic

<400> SEQUENCE: 31
ctcuucgtcg ctguctccgc utcuuccugc c                                      31

<210> SEQ ID NO 32
<211> LENGTH: 46
<212> TYPE: RNA
<213> ORGANISM: Artificial Sequence
<220> FEATURE:
<223> OTHER INFORMATION: Synthetic

<400> SEQUENCE: 32
gcggagacag cggguaacua gagaucccuc agacgggcag gaagaa                      46

<210> SEQ ID NO 33
<211> LENGTH: 25
<212> TYPE: RNA
<213> ORGANISM: Artificial Sequence
<220> FEATURE:
<223> OTHER INFORMATION: Synthetic

<400> SEQUENCE: 33

```
cgucugaggg aucucuaguu accuu                                         25
```

<210> SEQ ID NO 34
<211> LENGTH: 31
<212> TYPE: DNA
<213> ORGANISM: Artificial Sequence
<220> FEATURE:
<223> OTHER INFORMATION: Synthetic

<400> SEQUENCE: 34

```
ctcuucgtcg ctguctccgc utcuuccugc c                                  31
```

<210> SEQ ID NO 35
<211> LENGTH: 46
<212> TYPE: RNA
<213> ORGANISM: Artificial Sequence
<220> FEATURE:
<223> OTHER INFORMATION: Synthetic

<400> SEQUENCE: 35

```
gcggagacag cggguaacua gagaucccuc agacgggcag gaagaa                  46
```

<210> SEQ ID NO 36
<211> LENGTH: 25
<212> TYPE: RNA
<213> ORGANISM: Artificial Sequence
<220> FEATURE:
<223> OTHER INFORMATION: Synthetic

<400> SEQUENCE: 36

```
cgucugaggg aucucuaguu accuu                                         25
```

<210> SEQ ID NO 37
<211> LENGTH: 31
<212> TYPE: DNA
<213> ORGANISM: Artificial Sequence
<220> FEATURE:
<223> OTHER INFORMATION: Synthetic

<400> SEQUENCE: 37

```
gacutctcca gcucauggac ctccauuucc t                                  31
```

<210> SEQ ID NO 38
<211> LENGTH: 46
<212> TYPE: RNA
<213> ORGANISM: Artificial Sequence
<220> FEATURE:
<223> OTHER INFORMATION: Synthetic

<400> SEQUENCE: 38

```
gcuggugaag ucgguaacua gagaucccuc agacggaggu ccauga                  46
```

<210> SEQ ID NO 39
<211> LENGTH: 25
<212> TYPE: RNA
<213> ORGANISM: Artificial Sequence
<220> FEATURE:
<223> OTHER INFORMATION: Synthetic

<400> SEQUENCE: 39

```
cgucugaggg aucucuaguu accuu                                         25
```

<210> SEQ ID NO 40
<211> LENGTH: 31
<212> TYPE: DNA

```
<213> ORGANISM: Artificial Sequence
<220> FEATURE:
<223> OTHER INFORMATION: Synthetic

<400> SEQUENCE: 40
gacutctcca gcucauggac ctccauuucc t                          31

<210> SEQ ID NO 41
<211> LENGTH: 46
<212> TYPE: RNA
<213> ORGANISM: Artificial Sequence
<220> FEATURE:
<223> OTHER INFORMATION: Synthetic

<400> SEQUENCE: 41
gcuggugaag ucgguaacua gagaucccuc agacggaggu ccauga          46

<210> SEQ ID NO 42
<211> LENGTH: 25
<212> TYPE: RNA
<213> ORGANISM: Artificial Sequence
<220> FEATURE:
<223> OTHER INFORMATION: Synthetic

<400> SEQUENCE: 42
cgucugaggg aucucuaguu accuu                                 25

<210> SEQ ID NO 43
<211> LENGTH: 31
<212> TYPE: DNA
<213> ORGANISM: Artificial Sequence
<220> FEATURE:
<223> OTHER INFORMATION: Synthetic

<400> SEQUENCE: 43
gacutctcca gcucauggac ctccauuucc t                          31

<210> SEQ ID NO 44
<211> LENGTH: 46
<212> TYPE: RNA
<213> ORGANISM: Artificial Sequence
<220> FEATURE:
<223> OTHER INFORMATION: Synthetic

<400> SEQUENCE: 44
gcuggugaag ucgguaacua gagaucccuc agacggaggu ccauga          46

<210> SEQ ID NO 45
<211> LENGTH: 25
<212> TYPE: RNA
<213> ORGANISM: Artificial Sequence
<220> FEATURE:
<223> OTHER INFORMATION: Synthetic

<400> SEQUENCE: 45
cgucugaggg aucucuaguu accuu                                 25

<210> SEQ ID NO 46
<211> LENGTH: 31
<212> TYPE: DNA
<213> ORGANISM: Artificial Sequence
<220> FEATURE:
<223> OTHER INFORMATION: Synthetic

<400> SEQUENCE: 46
gacutctcca gcucauggac ctccauuucc t                          31
```

<210> SEQ ID NO 47
<211> LENGTH: 46
<212> TYPE: RNA
<213> ORGANISM: Artificial Sequence
<220> FEATURE:
<223> OTHER INFORMATION: Synthetic

<400> SEQUENCE: 47
gcuggugaag ucgguaacua gagaucccuc agacggaggu ccauga         46

<210> SEQ ID NO 48
<211> LENGTH: 25
<212> TYPE: RNA
<213> ORGANISM: Artificial Sequence
<220> FEATURE:
<223> OTHER INFORMATION: Synthetic

<400> SEQUENCE: 48
cgucugaggg aucucuaguu accuu         25

<210> SEQ ID NO 49
<211> LENGTH: 31
<212> TYPE: DNA
<213> ORGANISM: Artificial Sequence
<220> FEATURE:
<223> OTHER INFORMATION: Synthetic

<400> SEQUENCE: 49
gacutctcca gcucauggac ctccauuucc t         31

<210> SEQ ID NO 50
<211> LENGTH: 46
<212> TYPE: RNA
<213> ORGANISM: Artificial Sequence
<220> FEATURE:
<223> OTHER INFORMATION: Synthetic

<400> SEQUENCE: 50
gcuggugaag ucgguaacua gagaucccuc agacggaggu ccauga         46

<210> SEQ ID NO 51
<211> LENGTH: 25
<212> TYPE: RNA
<213> ORGANISM: Artificial Sequence
<220> FEATURE:
<223> OTHER INFORMATION: Synthetic

<400> SEQUENCE: 51
cgucugaggg aucucuaguu accuu         25

<210> SEQ ID NO 52
<211> LENGTH: 31
<212> TYPE: DNA
<213> ORGANISM: Artificial Sequence
<220> FEATURE:
<223> OTHER INFORMATION: Synthetic

<400> SEQUENCE: 52
gacutctcca gcucauggac ctccauuucc t         31

<210> SEQ ID NO 53
<211> LENGTH: 46
<212> TYPE: RNA
<213> ORGANISM: Artificial Sequence
<220> FEATURE:

<223> OTHER INFORMATION: Synthetic

<400> SEQUENCE: 53
gcuggugaag ucgguaacua gagaucccuc agacggaggu ccauga                         46

<210> SEQ ID NO 54
<211> LENGTH: 25
<212> TYPE: RNA
<213> ORGANISM: Artificial Sequence
<220> FEATURE:
<223> OTHER INFORMATION: Synthetic

<400> SEQUENCE: 54
cgucugaggg aucucuaguu accuu                                                25

<210> SEQ ID NO 55
<211> LENGTH: 31
<212> TYPE: DNA
<213> ORGANISM: Artificial Sequence
<220> FEATURE:
<223> OTHER INFORMATION: Synthetic

<400> SEQUENCE: 55
gacutctcca gcucauggac ctccauuucc t                                         31

<210> SEQ ID NO 56
<211> LENGTH: 46
<212> TYPE: RNA
<213> ORGANISM: Artificial Sequence
<220> FEATURE:
<223> OTHER INFORMATION: Synthetic

<400> SEQUENCE: 56
gcuggugaag ucgguaacua gagaucccuc agacggaggu ccauga                         46

<210> SEQ ID NO 57
<211> LENGTH: 25
<212> TYPE: RNA
<213> ORGANISM: Artificial Sequence
<220> FEATURE:
<223> OTHER INFORMATION: Synthetic

<400> SEQUENCE: 57
cgucugaggg aucucuaguu accuu                                                25

<210> SEQ ID NO 58
<211> LENGTH: 31
<212> TYPE: DNA
<213> ORGANISM: Artificial Sequence
<220> FEATURE:
<223> OTHER INFORMATION: Synthetic

<400> SEQUENCE: 58
gacutctcca gcucauggac ctccauuucc t                                         31

<210> SEQ ID NO 59
<211> LENGTH: 46
<212> TYPE: RNA
<213> ORGANISM: Artificial Sequence
<220> FEATURE:
<223> OTHER INFORMATION: Synthetic

<400> SEQUENCE: 59
gcuggugaag ucgguaacua gagaucccuc agacggaggu ccauga                         46

```
<210> SEQ ID NO 60
<211> LENGTH: 25
<212> TYPE: RNA
<213> ORGANISM: Artificial Sequence
<220> FEATURE:
<223> OTHER INFORMATION: Synthetic

<400> SEQUENCE: 60
cgucugaggg aucucuaguu accuu                                              25

<210> SEQ ID NO 61
<211> LENGTH: 31
<212> TYPE: DNA
<213> ORGANISM: Artificial Sequence
<220> FEATURE:
<223> OTHER INFORMATION: Synthetic

<400> SEQUENCE: 61
gacutctcca gcucauggac ctccauuucc t                                       31

<210> SEQ ID NO 62
<211> LENGTH: 46
<212> TYPE: RNA
<213> ORGANISM: Artificial Sequence
<220> FEATURE:
<223> OTHER INFORMATION: Synthetic

<400> SEQUENCE: 62
gcuggugaag ucgcaucgaa ccauuagcag aagacgaggu ccauga                       46

<210> SEQ ID NO 63
<211> LENGTH: 25
<212> TYPE: DNA
<213> ORGANISM: Artificial Sequence
<220> FEATURE:
<223> OTHER INFORMATION: Synthetic

<400> SEQUENCE: 63
gtcuucugcu aaugguucga ugcuu                                              25

<210> SEQ ID NO 64
<211> LENGTH: 31
<212> TYPE: DNA
<213> ORGANISM: Artificial Sequence
<220> FEATURE:
<223> OTHER INFORMATION: Synthetic

<400> SEQUENCE: 64
gacutctcca gcucauggac ctccauuucc t                                       31

<210> SEQ ID NO 65
<211> LENGTH: 46
<212> TYPE: RNA
<213> ORGANISM: Artificial Sequence
<220> FEATURE:
<223> OTHER INFORMATION: Synthetic

<400> SEQUENCE: 65
gcuggugaag ucgcaucgaa ccauuagcag aagacgaggu ccauga                       46

<210> SEQ ID NO 66
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 66
gtcuucugcu aaugguucga ugcuu                                          25

<210> SEQ ID NO 67
<211> LENGTH: 31
<212> TYPE: DNA
<213> ORGANISM: Artificial Sequence
<220> FEATURE:
<223> OTHER INFORMATION: Synthetic

<400> SEQUENCE: 67
gacutctcca gcucauggac ctccauuucc t                                   31

<210> SEQ ID NO 68
<211> LENGTH: 46
<212> TYPE: RNA
<213> ORGANISM: Artificial Sequence
<220> FEATURE:
<223> OTHER INFORMATION: Synthetic

<400> SEQUENCE: 68
gcuggugaag ucgcaucgaa ccauuagcag aagacgaggu ccauga                   46

<210> SEQ ID NO 69
<211> LENGTH: 25
<212> TYPE: DNA
<213> ORGANISM: Artificial Sequence
<220> FEATURE:
<223> OTHER INFORMATION: Synthetic

<400> SEQUENCE: 69
gtcuucugcu aaugguucga ugcuu                                          25

<210> SEQ ID NO 70
<211> LENGTH: 31
<212> TYPE: DNA
<213> ORGANISM: Artificial Sequence
<220> FEATURE:
<223> OTHER INFORMATION: Synthetic

<400> SEQUENCE: 70
gacutctcca gcucauggac ctccauuucc t                                   31

<210> SEQ ID NO 71
<211> LENGTH: 46
<212> TYPE: RNA
<213> ORGANISM: Artificial Sequence
<220> FEATURE:
<223> OTHER INFORMATION: Synthetic

<400> SEQUENCE: 71
gcuggugaag ucgcaucgaa ccauuagcag aagacgaggu ccauga                   46

<210> SEQ ID NO 72
<211> LENGTH: 25
<212> TYPE: DNA
<213> ORGANISM: Artificial Sequence
<220> FEATURE:
<223> OTHER INFORMATION: Synthetic

<400> SEQUENCE: 72
gtcuucugcu aaugguucga ugcuu                                          25

<210> SEQ ID NO 73
<211> LENGTH: 31
```

<212> TYPE: DNA
<213> ORGANISM: Artificial Sequence
<220> FEATURE:
<223> OTHER INFORMATION: Synthetic

<400> SEQUENCE: 73
gacutctcca gcucauggac ctccauuucc t                          31

<210> SEQ ID NO 74
<211> LENGTH: 46
<212> TYPE: RNA
<213> ORGANISM: Artificial Sequence
<220> FEATURE:
<223> OTHER INFORMATION: Synthetic

<400> SEQUENCE: 74
gcuggugaag ucgcaucgaa ccauuagcag aagacgaggu ccauga          46

<210> SEQ ID NO 75
<211> LENGTH: 25
<212> TYPE: DNA
<213> ORGANISM: Artificial Sequence
<220> FEATURE:
<223> OTHER INFORMATION: Synthetic

<400> SEQUENCE: 75
gtcuucugcu aaugguucga ugcuu                                 25

<210> SEQ ID NO 76
<211> LENGTH: 27
<212> TYPE: RNA
<213> ORGANISM: Artificial Sequence
<220> FEATURE:
<223> OTHER INFORMATION: Synthetic

<400> SEQUENCE: 76
cgcgucugag ggaucucuag uuaccuu                               27

<210> SEQ ID NO 77
<211> LENGTH: 27
<212> TYPE: DNA
<213> ORGANISM: Artificial Sequence
<220> FEATURE:
<223> OTHER INFORMATION: Synthetic

<400> SEQUENCE: 77
cgcgucugag ggaucucuag utaccuu                               27

<210> SEQ ID NO 78
<211> LENGTH: 12
<212> TYPE: RNA
<213> ORGANISM: Artificial Sequence
<220> FEATURE:
<223> OTHER INFORMATION: Synthetic

<400> SEQUENCE: 78
cccucagacg cg                                               12

<210> SEQ ID NO 79
<211> LENGTH: 13
<212> TYPE: RNA
<213> ORGANISM: Artificial Sequence
<220> FEATURE:
<223> OTHER INFORMATION: Synthetic

<400> SEQUENCE: 79
gguaacuaga gau                                                           13

<210> SEQ ID NO 80
<211> LENGTH: 27
<212> TYPE: RNA
<213> ORGANISM: Artificial Sequence
<220> FEATURE:
<223> OTHER INFORMATION: Synthetic

<400> SEQUENCE: 80
cgacgagcuc aucagguaac uagagau                                            27

<210> SEQ ID NO 81
<211> LENGTH: 27
<212> TYPE: RNA
<213> ORGANISM: Artificial Sequence
<220> FEATURE:
<223> OTHER INFORMATION: Synthetic

<400> SEQUENCE: 81
cgacgaagcu caucgguaac uagagau                                            27

<210> SEQ ID NO 82
<211> LENGTH: 27
<212> TYPE: RNA
<213> ORGANISM: Artificial Sequence
<220> FEATURE:
<223> OTHER INFORMATION: Synthetic

<400> SEQUENCE: 82
cgacgaagcu caucgguaac uagagau                                            27

<210> SEQ ID NO 83
<211> LENGTH: 26
<212> TYPE: RNA
<213> ORGANISM: Artificial Sequence
<220> FEATURE:
<223> OTHER INFORMATION: Synthetic

<400> SEQUENCE: 83
cgacgagcuc aucgguaacu agagau                                             26

<210> SEQ ID NO 84
<211> LENGTH: 13
<212> TYPE: DNA
<213> ORGANISM: Artificial Sequence
<220> FEATURE:
<223> OTHER INFORMATION: Synthetic

<400> SEQUENCE: 84
atctctagtt acc                                                           13

<210> SEQ ID NO 85
<211> LENGTH: 67
<212> TYPE: RNA
<213> ORGANISM: Artificial Sequence
<220> FEATURE:
<223> OTHER INFORMATION: Synthetic

<400> SEQUENCE: 85
gcuauggcag gaagaagcgg agacagcgac gaagagcuca ucagaacagu cggcgcaagc        60
cuuuuuu                                                                  67

<210> SEQ ID NO 86
<211> LENGTH: 67

```
<212> TYPE: RNA
<213> ORGANISM: Artificial Sequence
<220> FEATURE:
<223> OTHER INFORMATION: Synthetic

<400> SEQUENCE: 86
gcgaacggca uuagcggcac aagagacgac ggaagaguca ucagaacagu cggcgcaagc    60
cuuuuuu                                                              67

<210> SEQ ID NO 87
<211> LENGTH: 67
<212> TYPE: RNA
<213> ORGANISM: Artificial Sequence
<220> FEATURE:
<223> OTHER INFORMATION: Synthetic

<400> SEQUENCE: 87
gcuauggcag gaagaagcgg agacagcgca auccuuauca ucagaacagu cggcgcaagc    60
cuuuuuu                                                              67

<210> SEQ ID NO 88
<211> LENGTH: 67
<212> TYPE: RNA
<213> ORGANISM: Artificial Sequence
<220> FEATURE:
<223> OTHER INFORMATION: Synthetic

<400> SEQUENCE: 88
gcucacugag gaagaagcgg agacagcgac gaagagcuca ucagaacagu cggcgcaagc    60
cuuuuuu                                                              67

<210> SEQ ID NO 89
<211> LENGTH: 69
<212> TYPE: RNA
<213> ORGANISM: Artificial Sequence
<220> FEATURE:
<223> OTHER INFORMATION: Synthetic

<400> SEQUENCE: 89
gacaggucuc aucgggagga aauggagguc caugagcugg agaaguccaa gcgggcgcaa    60
gccuuuuuu                                                            69

<210> SEQ ID NO 90
<211> LENGTH: 67
<212> TYPE: RNA
<213> ORGANISM: Artificial Sequence
<220> FEATURE:
<223> OTHER INFORMATION: Synthetic

<400> SEQUENCE: 90
gcuauggcag gaagaagcgg agacagcgac gaagagcuca ucagaacagu cggcgcaagc    60
cuuuuuu                                                              67

<210> SEQ ID NO 91
<211> LENGTH: 71
<212> TYPE: RNA
<213> ORGANISM: Artificial Sequence
<220> FEATURE:
<223> OTHER INFORMATION: Synthetic

<400> SEQUENCE: 91
ucagcuccaa ggaugacgug ggcaagaacg uccaugagcu ggagaagucc aagcgggcgc    60
```
aagccuuuuu u                                                            71

<210> SEQ ID NO 92
<211> LENGTH: 70
<212> TYPE: RNA
<213> ORGANISM: Artificial Sequence
<220> FEATURE:
<223> OTHER INFORMATION: Synthetic

<400> SEQUENCE: 92
gacaggucuc aucgggagga aauggaggca agaagacaac aagacccuag uccugggcgc        60
aagccuuuuu                                                              70

<210> SEQ ID NO 93
<211> LENGTH: 29
<212> TYPE: RNA
<213> ORGANISM: Artificial Sequence
<220> FEATURE:
<223> OTHER INFORMATION: Synthetic

<400> SEQUENCE: 93
cuugcgucug agggaucucu aguuaccuu                                         29

<210> SEQ ID NO 94
<211> LENGTH: 23
<212> TYPE: DNA
<213> ORGANISM: Artificial Sequence
<220> FEATURE:
<223> OTHER INFORMATION: Synthetic

<400> SEQUENCE: 94
aaggtaacta gagatccctc aga                                               23

<210> SEQ ID NO 95
<211> LENGTH: 38
<212> TYPE: RNA
<213> ORGANISM: Artificial Sequence
<220> FEATURE:
<223> OTHER INFORMATION: Synthetic

<400> SEQUENCE: 95
ccucagacgc aagcugauga gcucuucguc gcugucuc                               38

<210> SEQ ID NO 96
<211> LENGTH: 13
<212> TYPE: RNA
<213> ORGANISM: Artificial Sequence
<220> FEATURE:
<223> OTHER INFORMATION: Synthetic

<400> SEQUENCE: 96
ccucagacgc aag                                                          13

<210> SEQ ID NO 97
<211> LENGTH: 30
<212> TYPE: RNA
<213> ORGANISM: Artificial Sequence
<220> FEATURE:
<223> OTHER INFORMATION: Synthetic

<400> SEQUENCE: 97
cgacgaagag cucaucggua acuagagauc                                        30

<210> SEQ ID NO 98
<211> LENGTH: 44

```
<212> TYPE: DNA
<213> ORGANISM: Artificial Sequence
<220> FEATURE:
<223> OTHER INFORMATION: Synthetic

<400> SEQUENCE: 98
aagguccctg atcgacgaag agcucaucag gguaacuaga gauc          44

<210> SEQ ID NO 99
<211> LENGTH: 14
<212> TYPE: RNA
<213> ORGANISM: Artificial Sequence
<220> FEATURE:
<223> OTHER INFORMATION: Synthetic

<400> SEQUENCE: 99
gguaacuaga gauc                                            14

<210> SEQ ID NO 100
<211> LENGTH: 14
<212> TYPE: RNA
<213> ORGANISM: Artificial Sequence
<220> FEATURE:
<223> OTHER INFORMATION: Synthetic

<400> SEQUENCE: 100
gguaacuaga gauc                                            14

<210> SEQ ID NO 101
<211> LENGTH: 40
<212> TYPE: DNA
<213> ORGANISM: Artificial Sequence
<220> FEATURE:
<223> OTHER INFORMATION: Synthetic

<400> SEQUENCE: 101
aaaaaagcgg agacagcgac gaagagctca tcagaaaaaa                40

<210> SEQ ID NO 102
<211> LENGTH: 27
<212> TYPE: RNA
<213> ORGANISM: Artificial Sequence
<220> FEATURE:
<223> OTHER INFORMATION: Synthetic

<400> SEQUENCE: 102
ccucagacgc aaggguaacu agagauc                              27

<210> SEQ ID NO 103
<211> LENGTH: 32
<212> TYPE: DNA
<213> ORGANISM: Artificial Sequence
<220> FEATURE:
<223> OTHER INFORMATION: Synthetic

<400> SEQUENCE: 103
tcgagtctgg taactagaga tccctcagac cc                        32

<210> SEQ ID NO 104
<211> LENGTH: 32
<212> TYPE: DNA
<213> ORGANISM: Artificial Sequence
<220> FEATURE:
<223> OTHER INFORMATION: Synthetic

<400> SEQUENCE: 104
```

```
ggccgggtct gagggatctc tagttaccag ac                                    32
```

<210> SEQ ID NO 105
<211> LENGTH: 28
<212> TYPE: DNA
<213> ORGANISM: Artificial Sequence
<220> FEATURE:
<223> OTHER INFORMATION: Synthetic

<400> SEQUENCE: 105

```
tcgagctgca tcgaaccatt agcagaaa                                         28
```

<210> SEQ ID NO 106
<211> LENGTH: 28
<212> TYPE: DNA
<213> ORGANISM: Artificial Sequence
<220> FEATURE:
<223> OTHER INFORMATION: Synthetic

<400> SEQUENCE: 106

```
ggcctttctg ctaatggttc gatgcagc                                         28
```

<210> SEQ ID NO 107
<211> LENGTH: 10
<212> TYPE: DNA
<213> ORGANISM: Artificial Sequence
<220> FEATURE:
<223> OTHER INFORMATION: Synthetic

<400> SEQUENCE: 107

```
ggcgcaagcc                                                             10
```

<210> SEQ ID NO 108
<211> LENGTH: 76
<212> TYPE: RNA
<213> ORGANISM: Artificial Sequence
<220> FEATURE:
<223> OTHER INFORMATION: Synthetic

<400> SEQUENCE: 108

```
gcccggauag cucggucggu ggagcaucag acuuuuaauc ugagggucca ggguucgagu      60
cccuguucgu gcacca                                                      76
```

<210> SEQ ID NO 109
<211> LENGTH: 22
<212> TYPE: DNA
<213> ORGANISM: Artificial Sequence
<220> FEATURE:
<223> OTHER INFORMATION: Synthetic

<400> SEQUENCE: 109

```
ctggaccctc agattaaaag tc                                               22
```

<210> SEQ ID NO 110
<211> LENGTH: 27
<212> TYPE: DNA
<213> ORGANISM: Artificial Sequence
<220> FEATURE:
<223> OTHER INFORMATION: Synthetic

<400> SEQUENCE: 110

```
ctccatttcc tcccgatgag acctgtc                                          27
```

<210> SEQ ID NO 111
<211> LENGTH: 26

```
<212> TYPE: DNA
<213> ORGANISM: Artificial Sequence
<220> FEATURE:
<223> OTHER INFORMATION: Synthetic

<400> SEQUENCE: 111
cgcttggact tctccagctc atggac                                          26

<210> SEQ ID NO 112
<211> LENGTH: 24
<212> TYPE: DNA
<213> ORGANISM: Artificial Sequence
<220> FEATURE:
<223> OTHER INFORMATION: Synthetic

<400> SEQUENCE: 112
aaaggtaact agagatccct caga                                            24

<210> SEQ ID NO 113
<211> LENGTH: 40
<212> TYPE: RNA
<213> ORGANISM: Artificial Sequence
<220> FEATURE:
<223> OTHER INFORMATION: Synthetic

<400> SEQUENCE: 113
cgacgaagcu caucagguaa cuagagaucc cucagacgcg                           40
```

PROGRAMMABLE CONDITIONAL SIRNAS AND USES THEREOF

PRIORITY CLAIM

This application is a continuation of International Patent Application No. PCT/US2019/046075, filed Aug. 10, 2019, which claims priority to U.S. Provisional Application No. 62/717,686, filed on Aug. 10, 2018, and 62/811,183, filed on Feb. 27, 2019, the contents of which are incorporated by reference herein in their entireties, including drawings.

STATEMENT OF GOVERNMENT INTEREST

This invention was made with government support under grant number AI029329, awarded by the National Institutes of Heath and grant numbers 1332411 and 1120890, awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Feb. 10, 2021, is named SequenceListing.txt and is 22 kilobytes in size.

BACKGROUND

A longstanding goal for nucleic acid nanotechnology[1-3] and biomolecular computing[4] is the development of conditionally activated oligonucleotide therapeutics that can detect and respond to cellular expression of specific genes[3,4]. Nucleic acid switches based on toehold mediated strand displacement[5,6] have executed logic operations and detected RNA transcripts in both bacteria[7] and mammalian cells[3,8], but the conditional activation of oligonucleotide drugs by RNA transcripts in mammalian cells has not been convincingly demonstrated. Significant challenges include poorly suppressed background drug activity, weak ON state drug potency, input and output sequence overlap, high design complexity, short device lifetimes (<24 hours) and high required device concentrations (>10 nM).

Over the past decade, synthetic RNAi triggers such as small interfering RNAs (siRNAs)[10] have become ubiquitous tools in biological research, and extensive basic and clinical development efforts have recently culminated in the FDA approval of ONPATTRO, the first RNAi drug[11]. Despite a burgeoning drug development pipeline and an extensive compendium of excipients targeting ligands and delivery techniques[9], the difficulty of delivering RNAi agents to specific populations of disease related cells continues to limit the potential of RNAi therapy. Repeated attempts over the past fifteen years to develop programmable, conditionally activated RNAi agents based on strand displacement switches[12-15] have not convincingly demonstrated the intended effects, despite notable progress[3,8,16-19]. Thus, a new conditionally activated siRNA (Cond-siRNA) is provided herein to overcome the problems in the art.

SUMMARY

In one aspect, this disclosure relates to a programmable, conditionally activated small interfering RNA construct (Cond-siRNA) in an OFF state, the construct comprising a sensor strand, a core strand, and a guide strand, wherein the sensor strand and the core strand bind complementarily to form a sensor duplex, the guide strand and the core strand bind complementarily to form a RNAi duplex, and the sensor duplex and the RNAi duplex are attached to each other to form a single structure. In some embodiments, the sensor duplex and the RNAi duplex are attached to each other via the core strand. In some embodiments, the sensor strand complementarily binds to a fragment on the 5' and a fragment on the 3' of the core strand to form the sensor duplex, and the guide strand complementarily binds to a fragment in the middle of the core strand to form the RNAi duplex and the fragment in the middle does not comprise any 5' or 3' sequence of the core strand such that the sensor duplex and RNAi duplex are attached to each other via two different fragments of the core strand. In some embodiments, the sensor domain of the Cond-siRNA construct comprises a sensor duplex formed by complimentary binding of the sensor strand and 3' and 5' fragments of the core strand, and a sensor overhang that does not pair up with the core strand. The sensor overhang is either at the 3' end or at the 5' end of the sensor strand. In some embodiments, the sensor strand, core strand, and guide strand form the single construct via self-assembling upon contact of each other. In some embodiments, the sensor duplex comprises 15, 16, 17, 18, 19, 20, 21, 22, 23, 24, 25, 26, 27, 28, 29, or 30 base pairs. In some embodiments, the RNAi duplex comprises 15, 16, 17, 18, 19, 20, 21, 22, 23, 24, 25, 26, 27, 28, 29, or 30 base pairs.

In some embodiments, the Cond-siRNA is chemically modified to further improve the OFF-state stability and/or dissociation efficiency when turned on upon contact with an input strand. For example, the bases of the sensor strand in the duplex region is modified by LNA modification, 2'-O-methyl modification, or both but not by phosphorothioate (PS) modification; either or both termini of the core strand are modified with PS modification, 2'-O-methyl modification, or both; or the single strand overhang of the sensor strand is modified by LNA modification, 2'-O-methyl modification, PS modification, or any combination thereof. In some embodiments, the sensor domain and the RNAi domain are modified by different chemical modifications.

The OFF-state Cond-siRNA described above is activated or turned on by contacting the OFF-state Cond-siRNA with an input strand, wherein one end of the input strand forms a toehold with the sensor strand overhang to induce displacement of the sensor strand from the core strand via complementary binding of the input strand and the sensor strand to form a waste duplex, whereby the RNAi duplex is completely disassociated from the construct.

BRIEF DESCRIPTION OF THE DRAWINGS

This application contains at least one drawing executed in color. Copies of this application with color drawing(s) will be provided by the Office upon request and payment of the necessary fees.

FIGS. 1a-d show conceptual design, operation, and molecular dynamics simulation of Cond-siRNAs. FIG. 1a shows the conceptual secondary and tertiary structure of the Cond-siRNA. Docking of the RNAi duplex to an x-ray crystal structure of Giardia Dicer shows massive steric clashes between the sensor duplex and Dicer. FIG. 1b shows RNAi activation via strand displacement. When a complementary input RNA meets the Cond-siRNA (I), the input forms a toehold with a 3' or 5' single stranded overhang on the sensor strand (II), leading to strand displacement (III). Displacement results in separation of the sensor strand from the RNAi duplex (IV). Cellular nucleases remove the core strand overhangs on the RNAi duplex (V), leaving an active RNAi trigger for Dicer processing (VI). FIGS. 1c and 1d show the Molecular Dynamics (MD) optimized models of constructs I.1 and III.1. Green block arrows denote direction of strand displacement from the 3' and 5' ends of the sensor strand.

FIGS. 3a-3f show sequence diagrams and map of optimization regions of prototype constructs (FIG. 3a)(SEQ ID NOS: 1-12), construct II variants (FIGS. 3b, 3c)(SEQ ID NOS: 13-36), construct III variants (FIGS. 3d, 3e)(SEQ ID NOS: 37-60), and construct IV variants (FIG. 3f)(SEQ ID NOS: 61-69).

FIG. 4a shows tat/rev RNA transcripts probed with mutant tRNALys3 matching their common leader sequence. Lanes: (L) Ambion decade marker; (0) negative control with RNA from mock transfection; (1) fully matching input RNA; (2) 5' mismatched input; (3) fully mismatched input; (4) duplex fusion mismatched activator (not used); (5) 3' mismatched activator. Expected size of the input RNA was 145-150 nt. FIG. 4b shows CBFB-MYH11 RNA transcripts. Lanes: (0) mock transfection; (1) tat/rev full match input (for comparison); (2) CBFB-MYH11 fusion; (3) MYH11 parental; (4) MYH11 parental. Successive panels show the same samples probed with mutant tRNALys3 probe, MYH11 probe, and CBFB probe. Expression levels of the input RNA were comparable across all cohorts.

FIGS. 5a-5k show assembly, strand displacement, RNAi activity and RNAi activation of construct I, II, and III variants. FIGS. 5a, 5d show non-denaturing PAGE of construct I and II assembly and isothermal strand displacement in 1×PBS buffer at 37° C. Constructs I and II are disassembled by their respective inputs and unaffected by mismatched inputs. Control lanes are: I=input, C=construct, P=RNAi duplex, W=waste duplex. FIGS. 5b, 5e show RNAi activities of constructs in the presence of mismatched inputs or null inputs and ON state constructs in the presence of mismatched inputs. FIGS. 5c, 5f show RNAi activity of OFF state constructs in cells expressing indicated inputs. g and h, OFF and ON state RNAi activity of construct II variants in cells expressing mismatched inputs. FIGS. 5i, 5j show RNAi activity of OFF state construct II and III variants with different core strand modifications in cells expressing either mismatched or matching inputs. FIG. 5k shows RNAi activity of construct III variants with different sensor strand modifications in cells with matching or mismatched inputs.

FIG. 9a shows RNAi activity of construct IV variants in cells expressing irrelevant, fusion activator, MYH11, or CBFB transcripts. FIG. 9b shows sensor strand binding position on each transcript. FIG. 9c shows sequence map of IV.3. Yellow highlights show areas (regions A, B, C and D) with optimized chemical modification motifs.

FIGS. 10a-10b show the relative RNAi activity for different RNA inputs for constructs I.1 (FIG. 10a) and III.1 (FIG. 10b). The target expression data from FIGS. 5c and 5f were renormalized against expression levels for cells transfected with Cond-siRNA but expressing fully mismatched input. Results show that target expression levels in cells expressing matching inputs were lower than those in cells expressing mismatched inputs. FIG. 10a: For construct I.1, cells expressing 5' mismatched and fully matched inputs had decreased target expression. FIG. 10b: For III.1, cells expressing the fusion input had decreased target expression.

FIG. 12A illustrates the structure of the construct, where the sensor domain and the siRNA domain are shaded in gray and the sensor duplex is shown in the box. FIG. 12B illustrates the cores strand regions I, II, and III, as well as the exonuclease blocking regions I and II in the core strand. FIG. 12C illustrates the sensor strand regions I, II, and III.

DETAILED DESCRIPTION

Figure 1A:
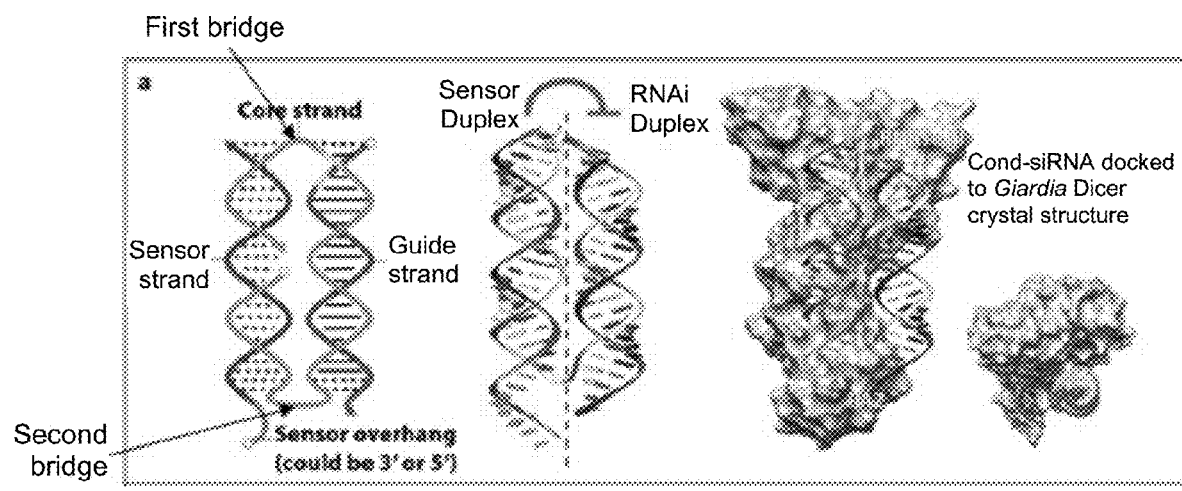

Disclosed herein are approaches for developing programmable, conditionally activated small interfering RNAs (Cond-siRNAs). These simple riboswitches can maintain their integrity over days in the mammalian cytosol and detect cellular RNA transcripts from specific input genes via toehold mediated strand displacement. Upon input detection, the Cond-siRNAs can release potent RNAi triggers[9] silencing specified target genes with completely independent sequences from the input. As demonstrated in the working examples, the switching activity of dozens of Cond-siRNA variants were tested in human adherent cells to identify necessary and sufficient chemical modification motifs that allow good device performance over diverse input:output combinations. Some optimized Cond-siRNAs achieved more than 90% silencing of target genes (protein expression versus baseline) in cells expressing sequence-matched RNA transcripts, and strongly suppressed background RNAi activity (<25% knockdown) in cells expressing mismatched inputs. Thus, provided herein is a method of substantively improving the performance of strand displacement switches in live mammalian cells. The Cond-siRNA technology provides a practical and versatile platform for gene expression activated RNAi smart drugs.

The Cond-siRNA constructs disclosed herein comprises two domains, the sensor domain and the RNAi domain, linked to each other by two fragments of the core strand. This structure is obtained by complementary binding of the sensor strand and the 3' fragment and the 5' fragment of the core strand to form a sensor duplex, and the complementary binding of the guide strand and a middle fragment of the core strand to form a RNAi duplex. As illustrated in FIG. 1, not the entire sequence of the core strand complementarily binds to the sensor strand or the guide strand. Rather, a first fragment in the core strand between the 3' fragment binding to the sensor strand and the middle fragment binding to the guide strand remains single-stranded to form a first "bridge" connecting a first end of the sensor domain to a first end of the RNAi domain. Likewise, a second fragment in the core strand between the 5' fragment binding to the sensor strand and the middle fragment binding to the guide strand remains single-stranded to form a second "bridge" connecting a second end of the sensor domain to a second end of the RNAi domain.

As used herein, the phrase "complementary binding" or "bind complementarily" means that two single strands are base paired to each other to form a double-stranded duplex. However, a certain percentage of mismatches between the two single strands are allowed as long as a stable double stranded duplex can be formed. For example, in some embodiments, the sensor duplex or the RNAi duplex has about 1%, about 2%, about 3%, about 4%, about 5%, about 6%, about 7%, about 8%, about 9%, about 10%, about 15%, about 20%, about 25%, about 30%, about 35%, about 40%, about 45%, or about 50% mismatches.

A. Input Strand

Input strands for Cond-siRNAs are "triggers" that switch on the Cond-siRNAs and are usually cellular RNA transcripts that are present at relatively high expression levels in a set of targeted cells (e.g. cancer cells) and at a relatively low level of expression in a set of non-targeted cells (e.g. normal cells). Based on the design of the disclosed Cond-siRNA constructs, only in the targeted cells, the RNAi is turned on; while in the non-targeted cells, the RNAi remains in OFF state. In the targeted cells, the input strand is expressed at a level at least 2-fold, at least 5-fold, at least 10-fold, at least 20-fold, at least 30-fold, at least 40-fold, at least 50-fold, at least 60-fold, at least 70-fold, at least 80-fold, at least 90-fold, or at least 100-fold higher than in the non-targeted cells. Alternatively, in the targeted cells, the input strand is expressed at a level of at least 50, at least 100, at least 200, at least 300, at least 400, at least 500, at least 600, at least 700, at least 800, at least 900, at least 1000 transcripts; and in the non-targeted cells, the input strand is expressed at a level of less than 50, less than 40, less than 30, less than 20, or less than 10 transcripts. Preferably, the non-targeted cells have no detectable expression of the input strand.

The input strand includes an mRNA, an miRNA, or a non-coding RNA such as a long non-coding RNA, an RNA fragment, or an RNA transcript of a virus. For therapeutic uses, the input RNA is usually an RNA transcript that is expressed in a set of cells that are causing the progression of a disease and are therefore targeted for RNAi therapy. The non-targeted cells are usually a set of cells where silencing of the RNAi target can cause side effects that are not beneficial for therapy. For treating a disease or a condition where the input RNA is overexpressed in targeted cells, the Cond-RNAi is designed such that the sensor strand has a sequence complementary to the input RNA sequence. Upon administration of the Cond-RNAi, the binding of sensor strand to the input RNA induces the dissociation of the RNAi duplex from the sensor duplex in targeted cells thereby to activate the RNAi targeting the disease or condition. In non-targeted cells the Cond-RNAi remains inactive.

B. Construct Design

As disclosed herein, Cond-siRNA constructs are designed for specific pairing of inputs and targets using an iterative protocol, exemplified below:

1. Obtain a guide strand sequence for the RNAi domain from previously validated siRNAs, literature sources, or siRNA design tools. In some embodiments, the guide strand has a size of 21 nt.
2. Create a Dicer substrate from the chosen guide strand by adding four G/C rich bases to the 5' of the guide strand. In some embodiments, the Dicer substrate has a size of 23 bp. Use Nupack (RNA strand, Mathews et al 1999 parameters, some dangle treatment) to check that the RNAi duplex forms with >95% probability at 1 nM concentration of guide (antisense) and sense strands.
3. From the sequence of the input biomarker, generate a list of all possible sensor segments which are antisense to the input strand. In some embodiments, the sensor segments are 31-33 nt in size. For the CBFP-MYH11 fusion sequence, only sensor segments that approximately meet parameters illustrated in FIG. 3b were considered.
4. Rank sensor sequences for uniqueness in the transcriptome of the target animal using NCBI BLAST. For human cancer cell lines, sequences were checked against human transcript and genomic collection using the BLASTn algorithm. Where possible, eliminate sensor segments that have more than 17 bases of sequence complementarity AND complete overhang complementarity to known or predicted RNA transcripts.
5. Starting with the most unique sensor segments, construct core strand sequences in accordance with desired structural parameters for the Cond-siRNA. Core strands have sequences of the form 5'-B-$C_3$-P-$C_3$-A-3' where A and B are complementary to the 5' and 3' ends of the sensor strand's putative duplex domain, P is complementary to the putative guide strand, and $C_3$ are $C_3$ linkers.
6. Use Nupack to rank the thermodynamic stability of the duplexes formed between sensor strand segments and their corresponding 5' and 3' core strand overhangs.

Use RNA strand, Mathews et al 1999 parameters, with some dangle treatment. Ideally, >95% of strands should be base-paired at 1 nM strand concentration. Also verify that the core strand does not have heavy internal secondary structure.

7. Choose the best constructs (guide, core, and sensor sequences) generated in steps 1-6.
8. Add chemical modifications disclosed herein.
9. Use oligonucleotide design tools such as "LNA Oligo Tm Prediction" (qiagen.com/us/service-and-support/learning-hub/technologies-and-research-topics/lna/custom-lna-design-and-applications/lna-design-tools-calculators/lna-oligo-tm-prediction/) or "LNA Oligo Optimizer" (qiagen.com/us/service-and-support/learning-hub/technologies-and-research-topics/lna/custom-lna-design-and-applications/lna-design-tools-calculators/lna-oligo-optimizer/) to optimize the placement of LNA modifications. LNA modifications are added to the sensor strand approximately 1 LNA per every 3 to 4 bases. Use the "LNA Oligo Optimizer" tool to check that the LNA pattern used does not lead to secondary structure or self-pairing interactions with scores higher than 60. Minimize self-complementarity and self-pairing scores to the extent possible. Use the "LNA Tm Prediction" tool to check the Tm of the LNA modified oligo when paired with RNA. Choose a placement that maximizes Tm while avoiding self-pairing interactions and secondary structure scores higher than 60 using the "LNA Oligo Optimizer" tool.

C. Design Features of Core Strand

Figure 12A:
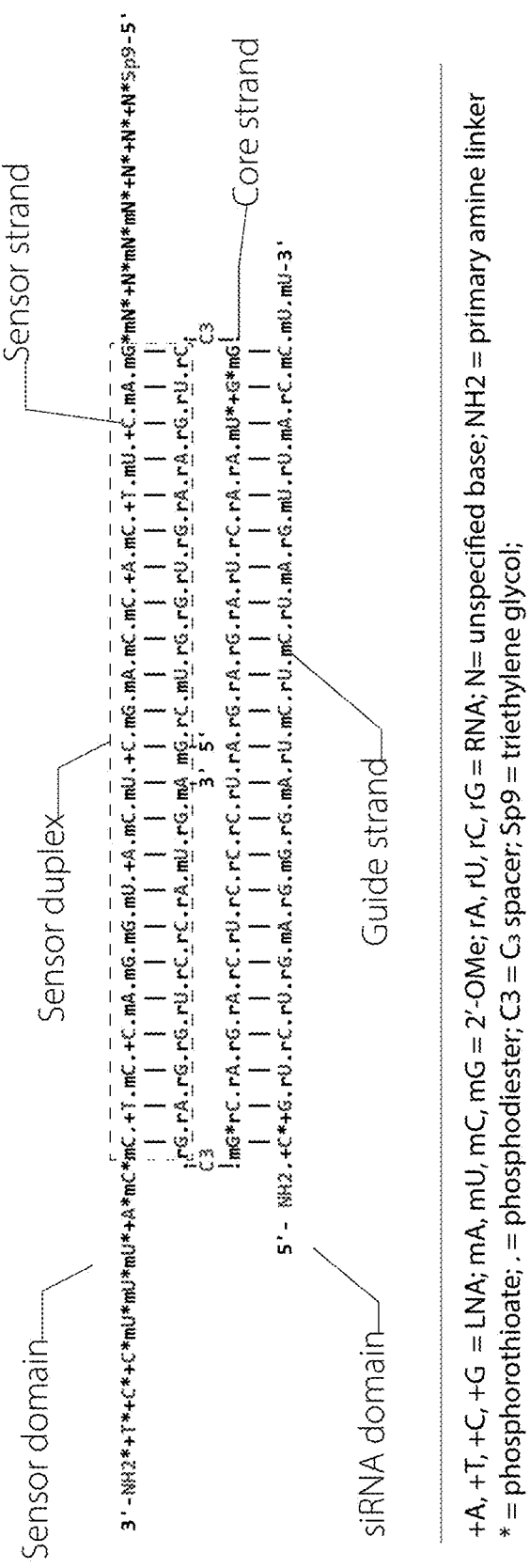
FIGS. 12A-12C (SEQ ID NOS: 73-75) illustrate an example of the Cond-siRNA disclosed herein.
Figure 12B:
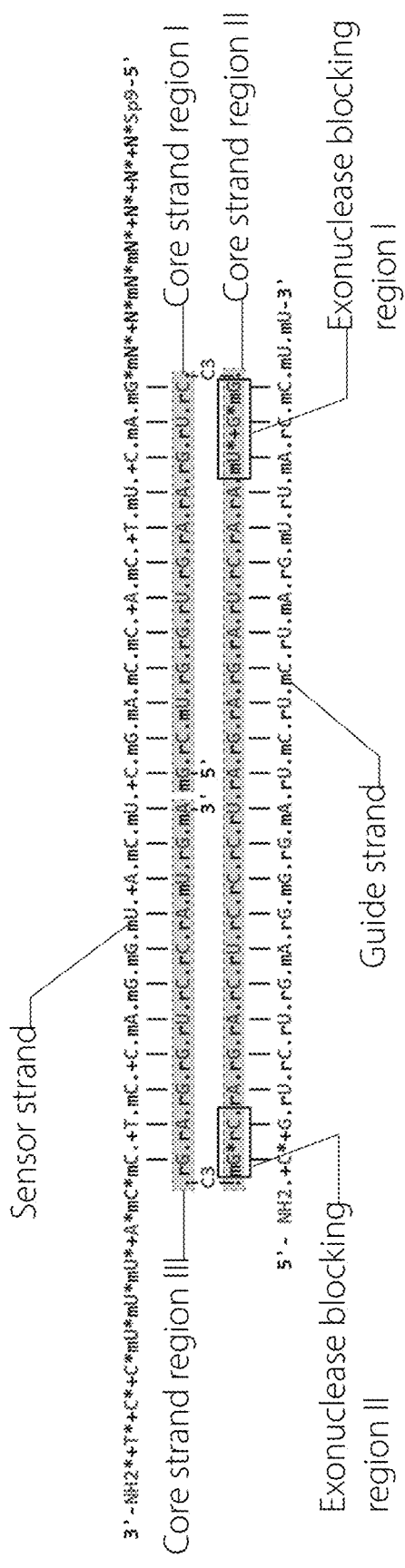
Figure 12C:
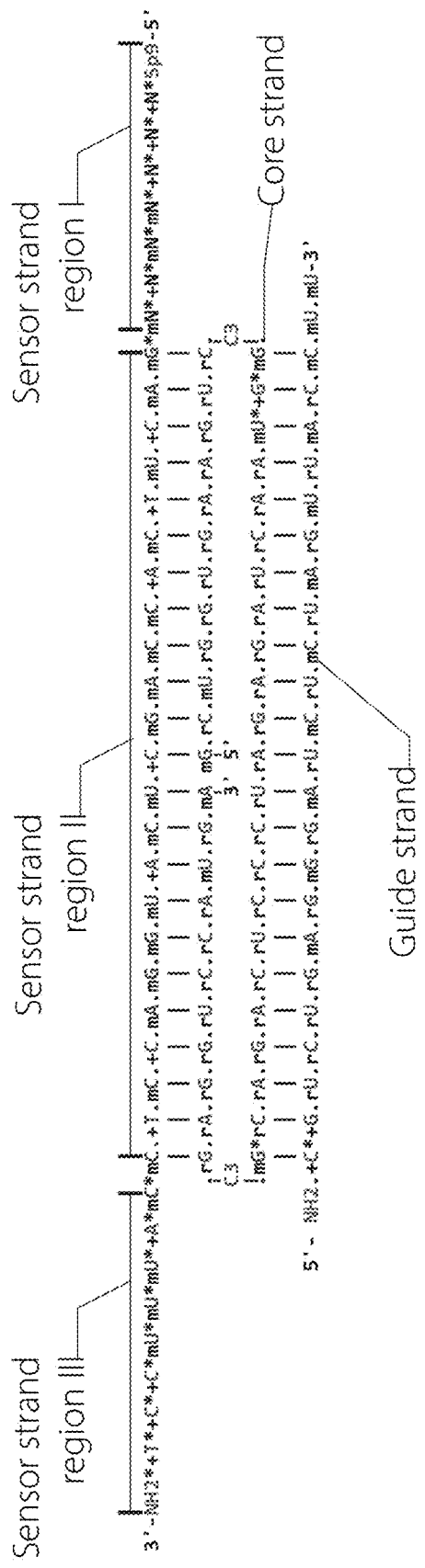

As illustrated in FIG. 12, in some embodiments, the core strand has one or more of the following features.

The 5' and 3' termini of the core strand have one or more of the following features:
a. The terminal base on the 5' is a 2'-F, 2'-O-methyl, or other modified base that resists nuclease cleavage.
b. The terminal base on the 3' is a 2'-F, 2'-O-methyl, or other modified base that resists nuclease cleavage.
c. The three terminal bases on the 5' have the pattern MRM, where M is a modified base (2'-O-methyl, 2'-F), and R is an RNA base.
d. The three terminal bases on the 3' have the pattern MRM, where M is a modified base (2'-O-methyl, 2'-F), and R is an RNA base.
e. The three terminal bases on the 3' and 5' do not have consecutive PS backbone modifications.
f. The portions of the core strand that are base-paired with the sensor strand have an alternating chemical modification pattern (MR)n.
g. In the above where M is a chemically modified base that does not decrease Tm of the duplex when compared to the equivalent RNA base.
h. Any combination of above where both the 5' and the 3' ends of the core strand have at least one of the features from a-g.
i. The 3' and 5' regions I and III of the core strand that are base-paired with the sensor strand are:
   (a) Entirely made out of the pattern (M)n, where M is a 2'-O-methyl or 2'-F modified base, or
   (b) at least 50% of the bases in this area are 2'-O-methyl or 2' F and, up to 30%, 50%, 80% or 100% of the backbone connections are not phosphorothioate.

The exonuclease blocking region I attached to the 5' terminus of the core strand (where the three bases base-paired with 5' terminus of the guide strand) has one or more of the following features:

a. an M*+*M pattern, where M is a 2' modified base (e.g. 2'-O-methyl or 2'-F), * is a PS backbone connection, and + is an LNA base or other 2'-4' bridged base,
b. an M*+*+ pattern, as defined above,
c. a +*+*+ pattern,
d. an R*+*M pattern, where R is an RNA base,
e. an R*+*+ pattern,
f. a +*M*M pattern, and
g. the patterns in a-f, where * can be either a PS backbone connection or an unmodified (phosphodiester) backbone connection.

The exonuclease blocking region II of the core strand has one or more of the following features:
a. an M*R pattern, where M is a 2' modified base (e.g. 2'-O-methyl or 2'-F), * is a PS backbone connection, and R is an LNA base or other 2'-4' bridged base,
b. an M*M pattern, as defined above,
c. a +*M pattern,
d. a +*R pattern, where R is an RNA base,
e. a +*+ pattern,
f. an M*+ pattern, and
g. the patterns in a-f, where * can be either a PS backbone connection or an unmodified (phosphodiester) backbone connection.

As used herein, "LNA" means locked nucleic acid, which is widely used in the field. See, for example, glenresearch.com/products/dna-rna-nucleosides-analogs-and-supports/backbone-modification/locked-analog-phosphoramidites.html, and en.wikipedia.org/wiki/Locked_nucleic_acid. Other techniques of base modifications, in addition to LNA modification, 2'-O-methyl modification, and 2'-F modification, are known in the art. See, for example, glenresearch.com/browse/nucleoside-analog-phosphoramidites. In some embodiments, glycol nucleic acids can be used.[61,62]

D. Design Features of Sensor Strand

As illustrated in FIG. 12, in some embodiments, the sensor strand has one or more of the following features. The sensor strand has a 5' overhang, a 3' overhang, or both.

Bases of the sensor strand have one or more of the following features: (1) at least 25% of the bases are not RNA or DNA, (2) at least 50% of the bases are not RNA or DNA, (3) at least 75% of the bases are not RNA or DNA, (4) 100% of the bases are not RNA or DNA, (5) at least one of the bases is an LNA or LNA analogue, (6) at least one of the 3 terminal bases are LNA or LNA analogue, (7) 10% to 50% of the bases are LNAs or LNA analogues, (8) 25% to 100% of the bases are LNAs or LNA analogues, (9) bases that are not LNAs are one or more of the following: (a) 2'-o-methyl, (b) 2'-fluoro, (c) 2'-MOE, (d) glycol nucleic acids,[61,62] and (e) other variants shown in glenresearch.com/browse/nucleoside-analog-phosphoramidites.

Phosphorothioate backbone connections can be present at various locations such as between the terminal base and the second to the last base, between the last 3 bases from the 5' or the 3' terminus, between the last 5 bases from the 5' or the 3' terminus, between the last 8 bases from the 5' or the 3' terminus, on 50% of the backbone connections, between all of the bases, and/or at the connection between regions I and II and between regions II and Ill.

Terminal modifications at the 5' end, the 3' end, or both include one or more of the following: (1) a tri or hexa ethylene glycol spacer, (2) a C3 spacer, (3) an inverted dT, (4) an amine linker, (5) other linkers or terminal modifications known in the art such as those listed at eu.idtdna.com/pages/products/custom-dna-rna/oligo-modifications, and www.glenresearch.com/browse/labels-and-modifiers, and (6) modifications may be used to attach the 3' and 5' end to other chemical moieties such as antibodies, gold or other metallic nanoparticles, polymeric nanoparticles, dendrimer nanoparticles, small molecules, single chain or branched fatty acids, peptides, proteins, aptamers, and other nucleic acid strands and nucleic acid nanostructures.

As illustrated in FIG. 3, region C of the sensor strand has one or more of the following features: (1) 50% or less of the backbone positions are phosphorothioate (PS) connections, (2) 50% or more of the bases are chemically modified to resist nuclease degradation or increase the melting temperature of the duplex (Tm), (3) 100% of the bases are chemically modified to resist nuclease degradation and increase Tm, (4) about 10%-50% of the bases are LNAs or other chemically modified base with 2'-4' bridging modifications that substantively increase the Tm. See, for example, glenresearch.com/products/dna-rna-nucleosides-analogs-and-supports/backbone-modification/locked-analog-phosphoramidites.html, and en.wikipedia.org/wiki/Locked_nucleic_acid.

In some embodiments, non-LNA modifications include 2'-o-methyl and 2'-F, as well as other modifications disclosed in glenresearch.com/browse/nucleoside-analog-phosphoramidites. In some embodiments, glycol nucleic acids can be used.[61,62]

In one aspect, the programmable conditionally activated RNAi (such as Cond-siRNAs) disclosed herein has a transfection concentration at lower than 0.1 nM in mammalian cells, compared to greater than 10 nM of other RNAi molecules known in the art. The Cond-siRNAs are active for an extended period of time such as at least 12 hours, at least 24 hours, at least 36 hours, at least 48 hours, at least 60 hours, at least 72 hours, at least 84 hours, or at least 96 hours. In some embodiments, the Cond-siRNAs are active for up to 30 days, up to 60 days, or up to 90 days.

As used herein, the term "programmable" means that the Cond-RNAi constructs disclosed herein are designed to allow the change of the sequences of input strand without substantial change of the secondary and tertiary structure of the constructs. Additional design principles are disclosed in U.S. Pat. No. 9,115,355, the contents of which are incorporated herein by reference.

Figure 2:
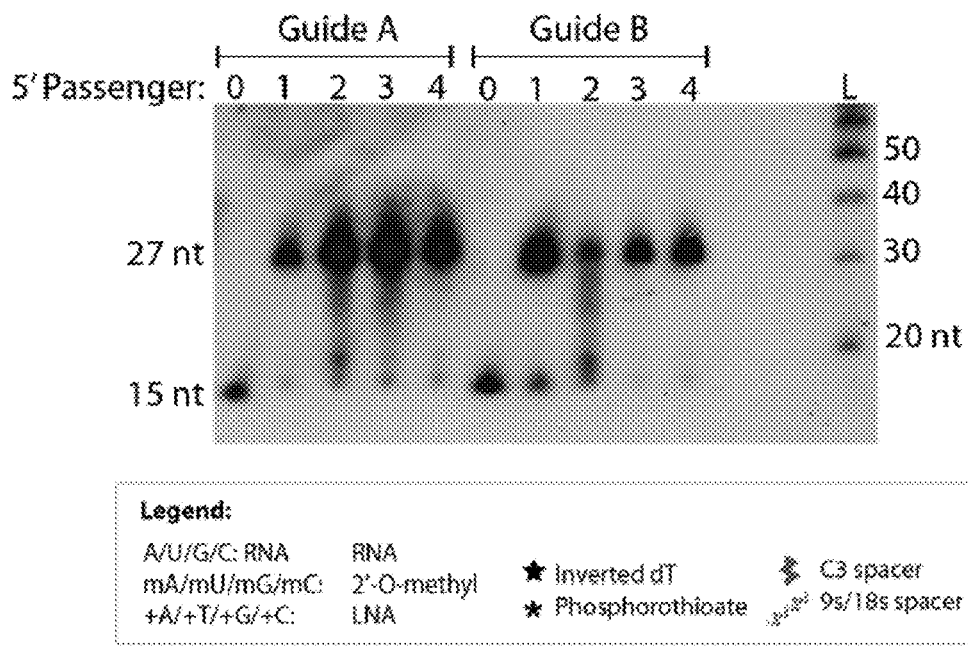
FIG. 2 (SEQ ID NOS: 77 and 113) shows intracellular degradation of chemically modified single stranded overhangs. Northern blot shows stepwise degradation of phosphorothioate (PS) protected 5' overhangs on test constructs. Test constructs (Dicer substrates with segmented passenger strand and various 5' overhangs) were transfected into HCT116 cells for 24 hours. The total RNA was extracted and analyzed via Northern blot. Two sets of similar samples were assayed, showing similar results at differing loading concentrations.
Figure 2:
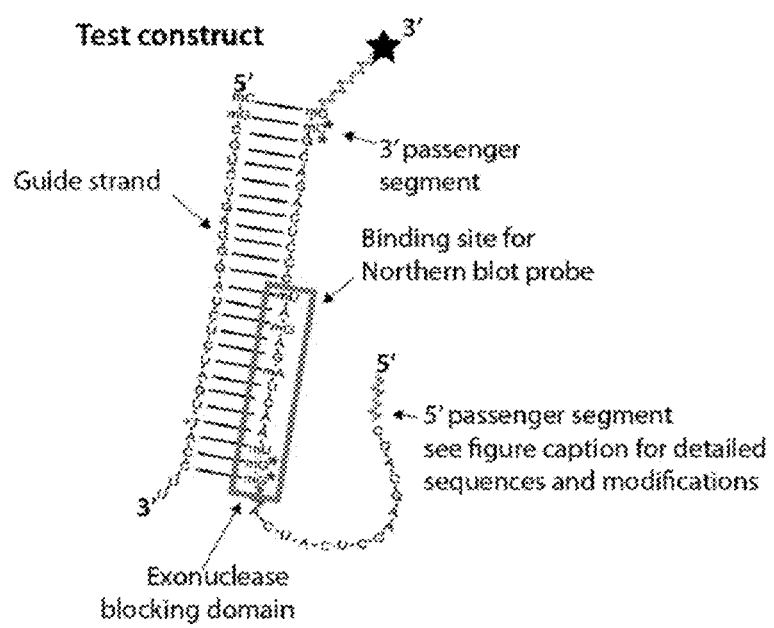

In some embodiments, dissociation of the RNAi duplex from the input-sensor duplex is increased by mismatches or wobble pairs between the core strand and the sensor strand. The RNAi trigger needs to completely dissociate from the waste duplex formed by the input RNA and the sensor strand to have potent RNAi activity. Prior schemes for conditional RNAi often featured activated RNAi triggers that remain attached to the input signal (e.g. an mRNA) via Watson-Crick base pairing[14,15,17,18,37] During development of a conditional RNAi trigger, it was found that the connection of Dicer substrates to adjacent chemically protected duplex RNA domains significantly reduced RNAi activity (FIG. 2). A possible cause for this could be binding of a Dicer inhibiting protein such as PACT38 to the extended duplex. In any case, dissociation of the RNAi duplex from the input-sensor duplex was critical in allowing simultaneous optimization of OFF state RNAi suppression and ON state RNAi potency.

In some embodiments, the Cond-siRNA disclosed herein has a single-construct design comprising a sensor duplex attached to a RNAi duplex. The existing designs for conditional RNAi triggers and other DNA circuits have featured either single-construct[14,15,39] or multi-construct[17] schemes for translating an input sequence into an independent output sequence. Single-construct translators should theoretically be intrinsically more efficient in signal detecting and transduction. However, the disadvantage is that the RNAi trigger must be concealed within the construct, creating an opportunity for spurious RNAi activation due to construct degradation.

In some embodiments, the Cond-siRNAs disclosed herein are chemically modified. For strand displacement sensors, the duplex domain of the sensor strand has LNA modification, 2'-O-methyl modification, or both. In some embodiments, the duplex domain of the sensor strand does not have phosphorothioate (PS) modifications. In some embodiments, either or both termini of the core strand or the protecting strand are modified with either PS or 2'-O-methyl. In some embodiments, thermodynamically stabilizing modifications generally improve suppression of background activation, while thermodynamically destabilizing modifications such as PS backbones can increase spurious activity when used extensively in duplex regions. In some embodiments, the chemical modifications are in the toehold domain, including LNA modification, 2'-O-methyl modification, PS modification, or a combination thereof. These modifications in the toehold domain improve the base-pairing affinity and nuclease resistance of the single stranded overhang.

As used herein, the binding partner to the sensor strand can also be called the "protecting strand". The protecting strand is the strand that is homologous to the input strand. The protecting strand can be the core strand. The sensor strand is the strand that is complementary to the input strand. Input binding to the sensor strand displaces the protecting strand.

In some embodiments, the chemical modifications include: (i) a sensor strand is modified with LNA and 2'-O-methyl, where the single stranded toehold region has PS backbone modifications but the base-paired duplex region does not have PS backbone modifications, (ii) either or both termini of a protecting strand have 2'-O-methyl modifications, or both (i) and (ii).

In some embodiments, the 3' and 5' terminal regions of the core strand are PS modified or 2'-O Me modified such that the Cond-siRNA construct is highly stable when base-paired with the sensor strand but vulnerable to degradation when unpaired. The degradation of single stranded overhangs can be stopped at the ends of duplexes by exonuclease blocking domains.

Complementing targeted drug delivery with self-regulating "smart drugs" that can activate or deactivate RNAi activity in response to cell-specific biochemical signals provide the means to overcome current limitations. For example, an RNAi smart drug that is able to detect and respond to viral RNA transcripts could potentially ablate persistent viral infections by killing virus-infected cells via viral-RNA-activated silencing of survival-essential host genes. This pharmacodynamics centered approach is well suited to the application of nucleic acid switches based on toehold mediated strand displacement, as these switches can sense and respond to specific base sequences in DNA or RNA inputs[3].

In one aspect, the Cond-siRNA disclosed herein is a self-assembled molecular mechanical transducer composed of a sensor strand, a guide strand, and a core strand, as shown in FIGS. 1a, 1c, and 1d. These three strands base-pair together to form a double crossover construct[20] consisting of a 23-base pair (bp) sensor duplex coupled to a 23-bp RNAi duplex. In the assembled configuration, the sensor inhibits enzymatic processing of the RNAi duplex, thereby keeping RNAi activity switched OFF in the mammalian cytosol (FIG. 1a).

In some embodiments, the Cond-siRNA constructs are further modified by chemical modifications such that their switching performance is improved. Specifically, the Cond-siRNAs disclosed herein have a reduced unwanted RNAi activity when the constructs are in their OFF state and improved switching from OFF to ON state in the presence of cellular RNA transcripts with the correct sequence.

The inhibition of enzymatic processing of the RNAi duplex occurs in multiple ways, which are synergistic in combination. For example, the position of the sensor duplex has large overlaps with the space required by Dicer's dsRBD and endonuclease domains during binding to the RNAi duplex (FIG. 1a, right)[21]. In another example, Dicer's PAZ domain has stabilizing interactions with the 5' terminal phosphate and 3' two-base overhang on the ends of canonical dsRNA triggers[22]. The assembled Cond-siRNA prevents these interactions because the core strand's 5' and 3' termini extend past the ends of the RNAi duplex into the middle of the sensor duplex (FIGS. 1c, 1d). The RNAi duplex is 23-bp long. This makes it too long to bypass Dicer cleavage for RNAi loading via alternative pathways[23]. In addition, interactions with RNAi pathway proteins required by alternative loading pathways (TRBP and Argonaute (1-4)[21]) are also likely hindered by the construct's unusual tertiary structure. Additionally, to prevent premature degradation of the sensor duplex or unintended separation of the sensor from the RNAi duplex, the entire sensor strand and other key sites on the construct are stabilized thermodynamically and protected from nuclease activity by extensive chemical modifications[24] (FIGS. 1c, 1d).

To release and activate the RNAi duplex, a cellular RNA transcript induces separation of the sensor strand from the core strand via toehold mediated strand displacement (FIG. 1b). In some embodiments, the cellular RNA transcript is from an internal source of the subject, such as a metabolism product. Displacement can start from a toehold formed at the 3' or 5' terminus of the sensor strand. The sequence specificity of input detection is enforced in the toehold region by the strong dependence of strand displacement kinetics on toehold stability[25], and in the duplex region by the need to displace the fully complementary core strand.

Figure 3A:
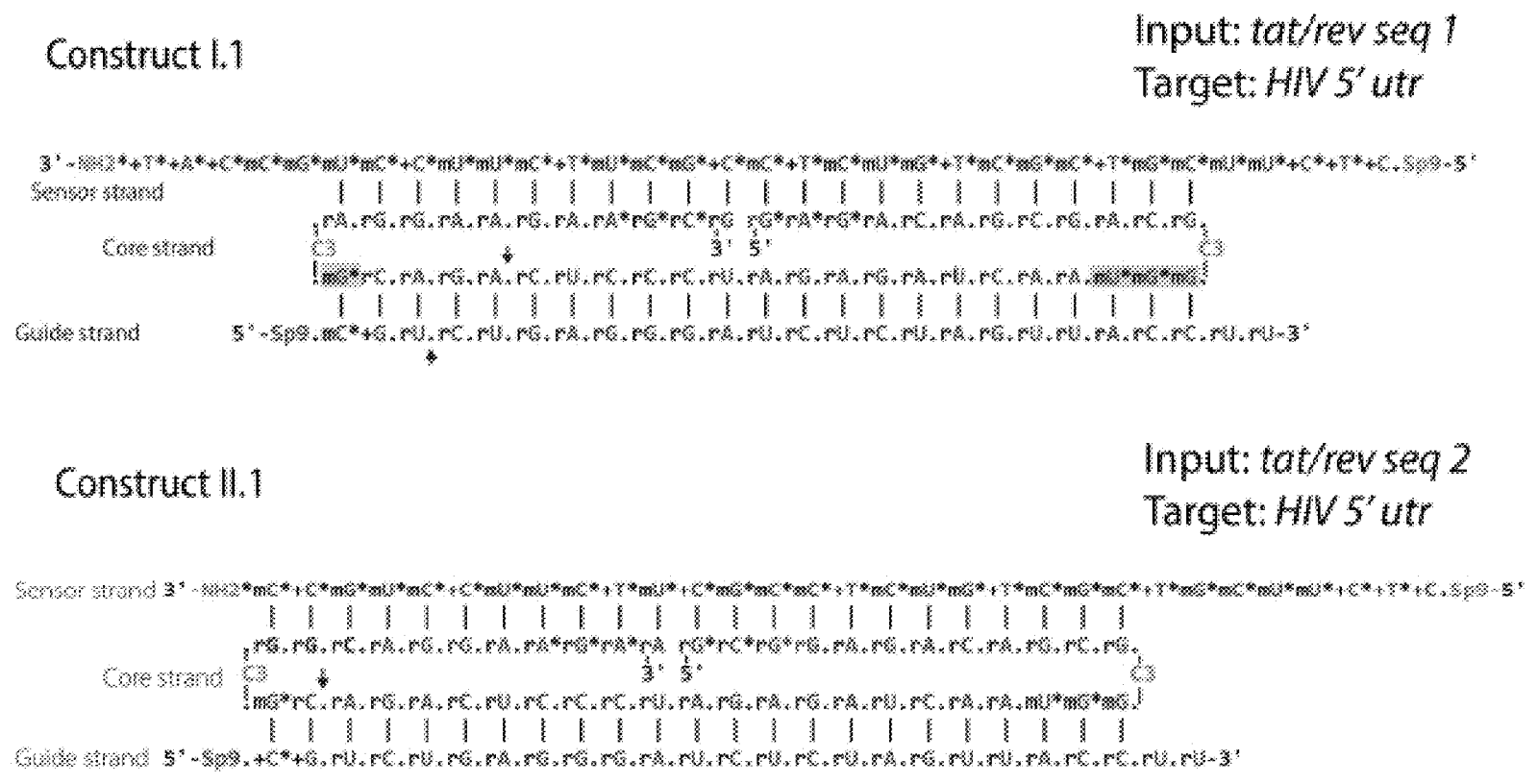

After separation from the sensor strand, the displaced regions of the core strand become 3' and 5' overhangs extending from the RNAi duplex. The overhangs are degraded by cytosolic nucleases[26] (FIG. 1b V and FIG. 2), which are stopped at the ends of the RNAi duplex by chemically modified nuclease blocking domains (FIG. 3a, yellow highlights in construct I.1). This leaves an active RNAi trigger for Dicer processing and RISC loading (FIG. 1b, VI, siRNA).

Strand compositions used in the intracellular degradation of chemically modified single stranded overhangs were as follows:
Sequences (5'->3')

```
        Guide A:
                                        (SEQ ID NO: 76)
        mCmG C GUCUGAGGGAUCUCUAGU UACCUU Guide B:
                                        (SEQ ID NO: 77)
        mCmG+CGUCUGAGGGAUCUCUAGU+TACCUU 3' passenger segment:
                                        (SEQ ID NO: 78)
        cccucagacg mc*mg*9s idT
```

```
        -continued
        5' Passenger segments
        0 (control):
                                        (SEQ ID NO: 79)
        c3 mG*mG*mU AACUmAGAmGAm U 1:
                                        (SEQ ID NO: 80)
        C G A C G A G C U C A U C A c3mG*mG*mU AACUmAGAmGAm U 2:
                                        (SEQ ID NO: 81)
        18s *C*G*A*C*G*A*A*G*C*U*C*A*U*C* c3mG*mG*mU AACUmAGAmGAm U

3:
                                        (SEQ ID NO: 82)
        18s *C*G*A*C*G*A*A*G*C*U*C*A U C c3mG*mG*mU AACUmAGAmGAm U

4:
                                        (SEQ ID NO: 83)
        18s *C*G*A*C G A G C U C A U C c3mG*mG*mU AACUmAGAmGAm U

Northern probe:
                                        (SEQ ID NO: 84)
        ATCTCTAGTTACC
        L: Ambion decade marker
        Abbreviations:
        9s: triethylene glycol spacer
        18s: hexaethylene glycol spacer
        C3: C3 spacer
        idT: inverted dT
        *phosphorothioate backbone connection.
```

As shown in FIG. 2, samples with guide strand A had sufficient loading and exposure to visualize all bands. Lane 0 shows position of control strand with no overhang (15 nucleotides). Passenger 1 has a reduced amount of full length passenger strand with a single detectable band at ~15 nt, indicating rapid processive degradation of the overhang. Passengers 2 and 3 had multiple bands and streaks throughout the size range between 15 and 27 nt, indicating a slow, non-processive loss of nucleotides, consistent with presence of PS backbone connections throughout the overhang. Passenger 4 showed higher amounts of full length product versus 0, with two bands visible near 15 nt, indicating a slower initial degradation rate due to end protection, before rapid processive loss of the overhang once 5' terminal protection is lost.

Several Cond-siRNAs were designed with chemical modification motifs similar to those used to protect antisense oligonucleotides (ASO) and other oligonucleotide therapeutics[24]. Construct I.1 (FIG. 3a) was programmed to detect a conserved HIV (tat/rev) mRNA gene sequence[27]. The activator sequences for constructs I and II are shown in Table 1 below. Regions meant to align with sensor strand are bold and italicized; regions meant to align with toehold are underlined; segments complementary to the sensor strand are in upper case; and segments mismatched with sensor strand are in lower case.

TABLE 1

Activator Sequences for Constructs I and II

| | |
|---|---|
| Fully matched | Gcu*AUGGCAGGAAGAAGCGGAGACAGCGACGAAGAG*cuca ucagaacagucggcgcaagccuuuuuu (SEQ ID NO: 85) |
| Full mismatch | Gcgaacggcauuagcggcacaagagacgacggaagaguca ucagaacagucggcgcaagccuuuuuu (SEQ ID NO: 86) |
| 5' mismatch | Gcu*AUGGCAGGAAGAAGCGGAGACAGCG*caauccuuauca ucagaacagucggcgcaagccuuuuuu (SEQ ID NO: 87) |
| 3' mismatch | Gcu*cacugAGGAAGAAGCGGAGACAGCGACGAAGAG*cuca ucagaacagucggcgcaagccuuuuuu (SEQ ID NO: 88) |

Construct III.1 (FIG. 3a) was programmed to detect an acute myeloid leukemia (AML) associated fusion oncogene sequence (CBFB-MYH11)[28,29]. The activator sequences for constructs III and IV are shown in Table 2 below. Regions meant to align with sensor strand are bold and italicized; regions meant to align with toehold are underlined; segments complementary to the sensor strand are in upper case; and segments mismatched with sensor strand are in lower case.

TABLE 2

Activator Sequences for Constructs III and IV

| | |
|---|---|
| Fully matched | Gacaggucucaucggg*AGGAAAUGGAGGUCCAUGAGCUG GAGAAGUC*CAgcgggcgcaagccuuuuuu (SEQ ID NO: 89) |
| Full mismatch | gcuauggcaggaagaagcggagacagcgacgaagagcuc aucagaacagucggcgcaagccuuuuuu (SEQ ID NO: 90) |

TABLE 2-continued

Activator Sequences for Constructs III and IV

| | |
|---|---|
| MYH11 parental | ucagcuccaaggaugacg*ugggcaagaacGUCCAUGAGC UGGAGAAGUC*caagcgggcgcaagccuuuuuu (SEQ ID NO: 91) |
| CBFβ parental | gacaggucucaucggg*AGGAAAUGGAGGcaagaagacaa caagacc*cuaguccugggcgcaagccuuuuu (SEQ ID NO: 92) |

To allow direct readout of RNAi activity, both constructs I.1 and III.1 targeted a *Renilla* luciferase mRNA bearing a biologically irrelevant target sequence in its 3' UTR (from the U5 region of HIV).

Figure 4A:
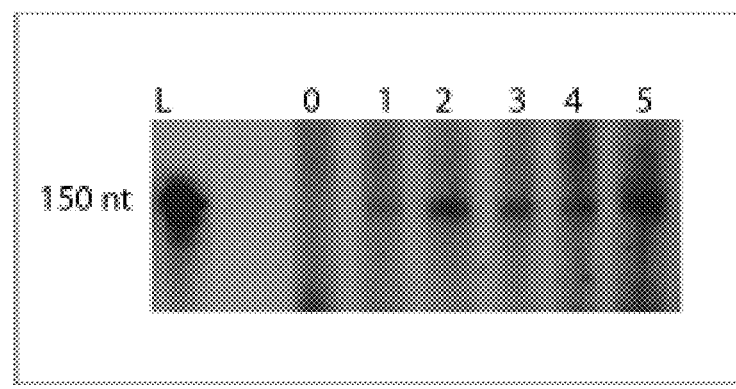
FIGS. 4a-4b show Northern blot of RNA inputs in HCT 116 cells. Northern blot assay probing tat/rev and AML input RNA recovered from HCT 116 cells after 48 hours.
Figure 4B:
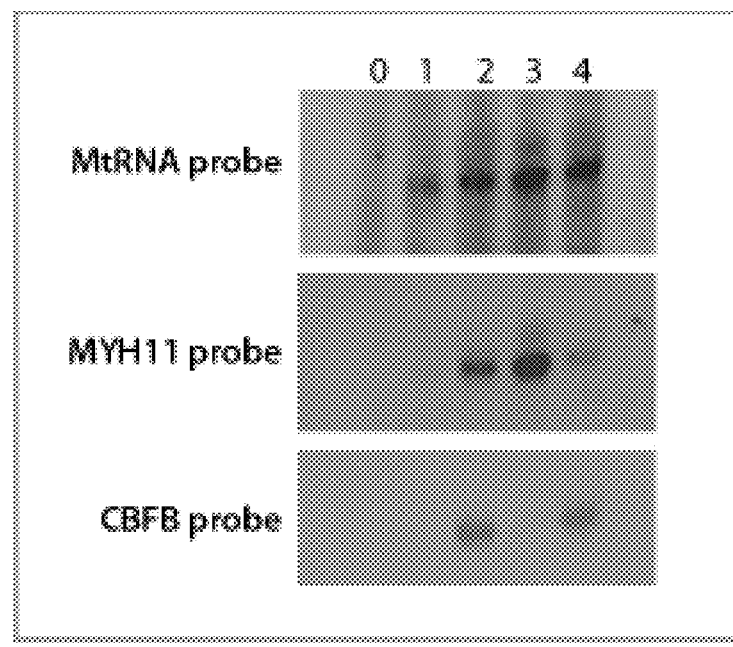

To predict realistic molecular conformations, atomistic molecular dynamics (MD) simulations[30] of I.1 and III.1 were conducted in explicit solvent using a hybrid Amber force field that uses a combination of previously published parameters[31-33] for describing the chemical modifications used in our design. MD optimized models for both constructs (FIGS. 1c, 1d) show that there are structural distortions in the sensor and RNAi duplexes compared with ideal A-form RNA helical parameters (FIG. 4). The distortions are attributable to (1) extensive incorporation of chemical modifications and (2) structural strain intrinsic in the double crossover motif (FIGS. 1c, 1d, 4, and Tables 3a and 3b). Tables 3a and 3b below show average base-pair parameters of sensor and siRNA duplexes over 5 nanoseconds of Molecular Dynamics trajectories. The mean and standard deviation values for each base-pair parameter for each denoted duplex was calculated from the data shown in FIG. 4. For comparison, mean and standard deviations were also calculated for unconnected RNA duplexes with the same sequence composition as the siRNA and sensor duplexes in the HIV and AML constructs (both constructs had the same sequence in the siRNA duplex).

TABLE 3a

| | | | Degrees Buckle | Å Rise | Degrees Twist | Degrees Opening | Degrees Propeller | Degrees Roll |
|---|---|---|---|---|---|---|---|---|
| RNA duplexes with no modified nucleotides | siRNA duplex | Mean | 0.87 | 2.74 | 31.59 | 0.78 | -12.57 | 7.71 |
| | | STD | 12.00 | 0.52 | 4.14 | 4.88 | 8.46 | 6.17 |
| | I.1 sensor duplex | Mean | -3.49 | 2.66 | 32.32 | 0.50 | -12.56 | 7.91 |
| | | STD | 10.99 | 0.56 | 4.58 | 4.64 | 8.35 | 6.50 |
| | II.1 sensor duplex | Mean | -4.36 | 2.61 | 31.57 | 0.01 | -12.40 | 8.44 |
| | | STD | 11.12 | 0.89 | 7.28 | 4.59 | 8.83 | 6.42 |
| I.1 construct | siRNA | Mean | 0.00 | 2.68 | 31.55 | 0.38 | -12.31 | 7.98 |
| | | STD | 12.47 | 0.63 | 5.02 | 4.96 | 8.71 | 7.14 |
| | Sensor | Mean | 1.54 | 2.95 | 29.54 | -0.42 | -8.47 | 4.09 |
| | | STD | 11.85 | 0.57 | 4.66 | 4.75 | 8.63 | 6.71 |
| II.1 construct | siRNA | Mean | 0.09 | 2.75 | 31.55 | 0.25 | -12.08 | 7.29 |
| | | STD | 9.62 | 0.69 | 5.36 | 4.07 | 9.16 | 6.12 |
| | Sensor | Mean | 1.49 | 2.73 | 29.87 | -0.11 | -10.36 | 5.89 |
| | | STD | 10.14 | 0.70 | 5.67 | 4.35 | 8.44 | 6.22 |

TABLE 3b

| | | | Degrees Shear | Å Shift | Degrees Slide | Degrees Stagger | Degrees Stretch | Degrees Tilt |
|---|---|---|---|---|---|---|---|---|
| RNA duplexes with no modified nucleotides | siRNA duplex | Mean | 0.00 | 0.02 | -1.68 | -0.06 | -0.09 | -0.04 |
| | | STD | 0.33 | 0.67 | 0.49 | 0.42 | 0.14 | 4.66 |
| | I.1 sensor duplex | Mean | -0.02 | 0.01 | -1.63 | -0.09 | -0.10 | 0.34 |
| | | STD | 0.31 | 0.66 | 0.51 | 0.42 | 0.13 | 4.86 |
| | II.1 sensor duplex | Mean | -0.04 | 0.10 | -1.68 | -0.08 | -0.05 | 0.17 |
| | | STD | 0.32 | 0.80 | 0.51 | 0.43 | 0.13 | 4.63 |

TABLE 3b-continued

|  |  |  | Degrees Shear | Å Shift | Degrees Slide | Degrees Stagger | Degrees Stretch | Degrees Tilt |
|---|---|---|---|---|---|---|---|---|
| I.1 construct | siRNA | Mean | 0.00 | 0.04 | −1.82 | −0.08 | −0.03 | 0.12 |
|  |  | STD | 0.32 | 0.71 | 0.57 | 0.43 | 0.14 | 4.80 |
|  | Sensor | Mean | 0.00 | −0.25 | −2.18 | 0.04 | −0.06 | −0.82 |
|  |  | STD | 0.33 | 0.69 | 0.52 | 0.43 | 0.14 | 4.87 |
| II.1 construct | siRNA | Mean | 0.00 | 0.05 | −1.82 | −0.05 | −0.04 | 0.06 |
|  |  | STD | 0.32 | 0.71 | 0.56 | 0.40 | 0.12 | 4.72 |
|  | Sensor | Mean | −0.01 | −0.24 | −2.16 | 0.03 | −0.05 | −0.80 |
|  |  | STD | 0.33 | 0.71 | 0.53 | 0.41 | 0.13 | 4.69 |

Despite distortions, all intended base pairs were maintained throughout simulation, and the relative dispositions of the sensor and RNAi duplexes in both models were consistent with steric protection from Dicer cleavage.

Figure 5C:
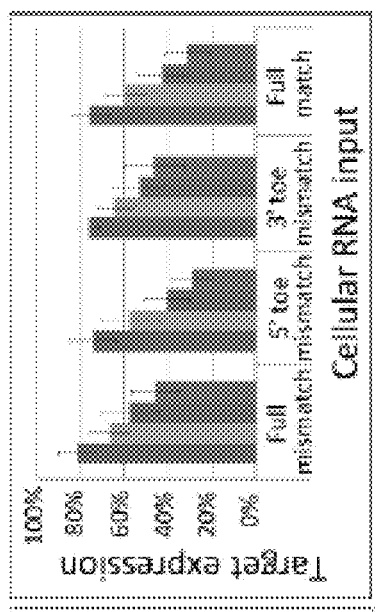

For empirical testing of the constructs, the component strands were purchased from commercial sources and Cond-siRNAs were assembled using thermal annealing in 1×PBS. Non-denaturing polyacrylamide gel (PAGE) analysis showed that both constructs assembled with high purity, were capable of sequence specific detection of input RNA, and could release RNAi duplexes via isothermal strand displacement at 37° C. in 1×PBS buffer (FIGS. 5a, 5d).

The RNAi activities of OFF (guide, core, and sensor strands) and ON (guide and core strands only) state Cond-siRNAs were measured using dual luciferase assays. Varying amounts of constructs were co-transfected into HCT116 cells with fixed amounts of DNA vectors encoding (a) the dual luciferase reporter and (b) short RNA inputs complementary (matched) or noncomplementary (mismatched) sequences to the sensor strand (Tables 1 and 2).

Figure 5B:
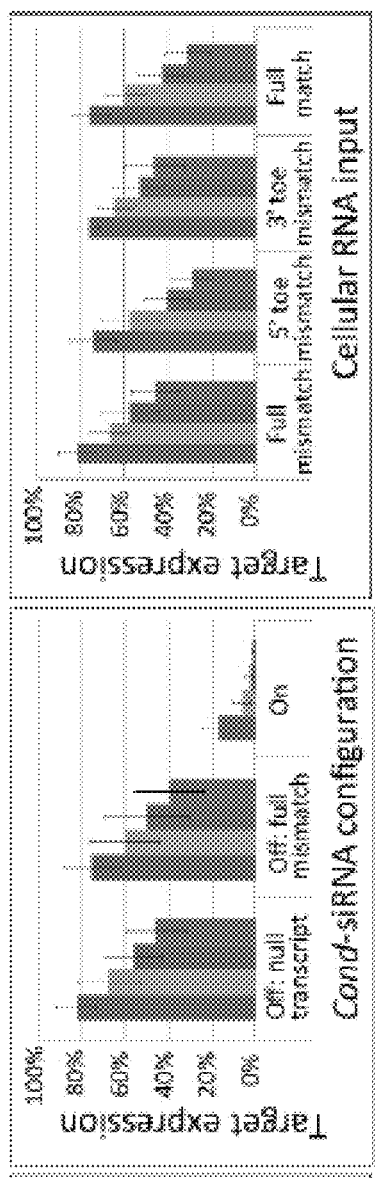
Figure 5A:
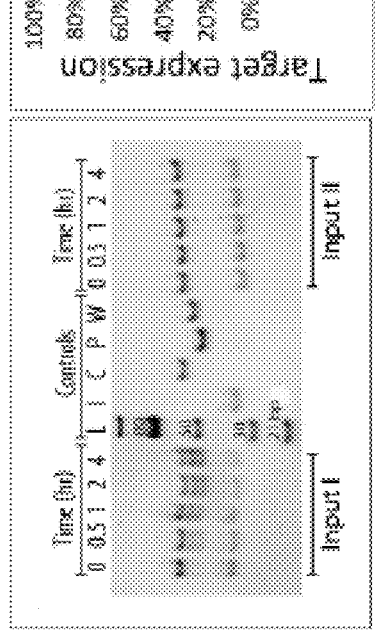
Figure 5F:
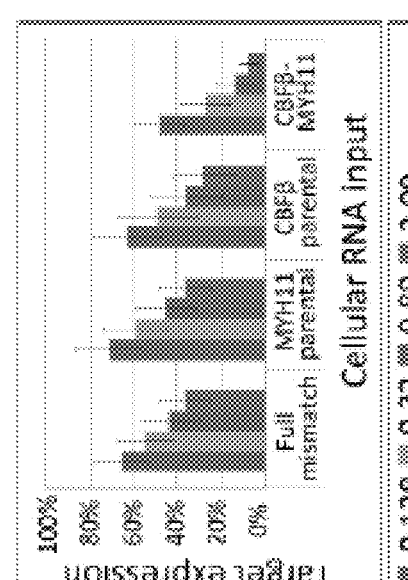
Figure 5E:
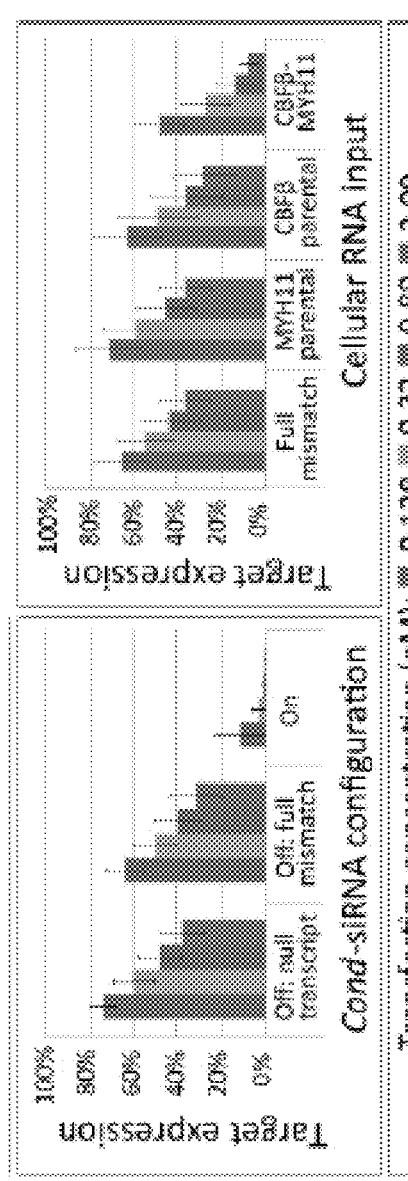
Figure 5D:
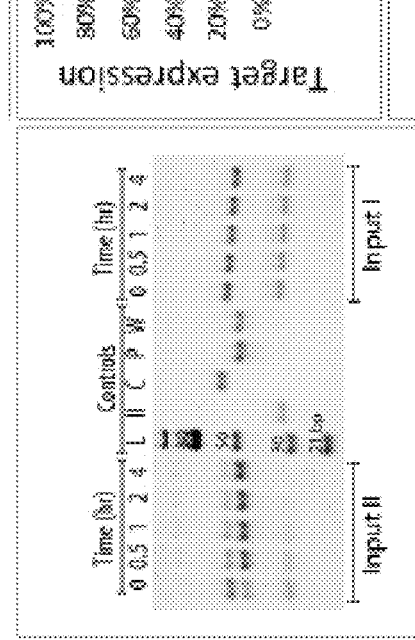
Figure 6:
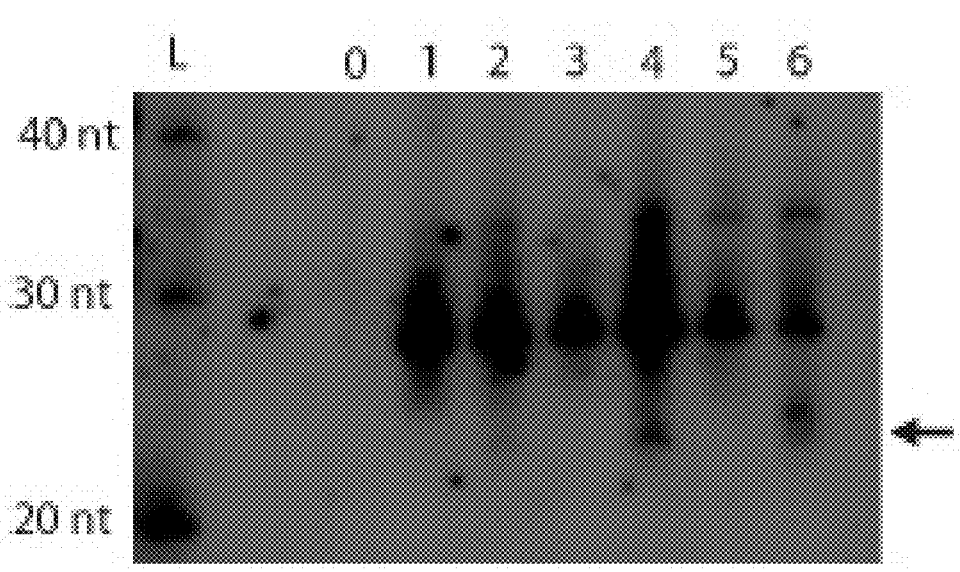
FIG. 6 shows Dicer processing of pre-activated Cond-siRNA constructs. Northern blot assay probing Cond-siRNA guide strands recovered from HCT 116 cells after 48 hours. Lanes are as follows: (L) Ambion decade marker; (0) RNA from cells with mock transfection; (1) and (2) guide strands from a third prototype Cond-siRNA not reported in this paper; (3) and (4) OFF and ON states of prototype the HIV construct; (5) and (6) OFF and ON states of the AML construct. Arrow marks position of Dicer cleaved guide strand. Dicer cleavage products (~21 nt guide strand fragment) were detected in RNA material extracted from cells transfected with ON state Cond-siRNAs, but not from cells transfected with OFF state Cond-siRNAs.

In cells expressing null or fully mismatched inputs, OFF state Cond-siRNAs had significantly reduced RNAi activity while ON state constructs proved to be potent RNAi triggers (FIGS. 5b, 5e corroborated by Northern blot assay results FIG. 6). For RNAi activation, OFF state constructs were transfected into cells expressing matched or mismatched inputs (FIGS. 5c, 5f). Expression levels of input RNA were assessed using Northern blot (FIG. 4). Although fluctuations in the background (OFF state) RNAi activity level reduced the apparent statistical significance when the data was normalized to target expression in cells with no transfect siRNA (FIGS. 5c and 5f), an alternative analysis directly comparing matching and mismatched inputs suggested that there was a significant RNAi activity increase with matching inputs (FIG. 10).

The different sensor designs of I.1 and III.1 appeared to result in some functional differences in RNAi activation. Construct I.1 had five nucleotide 5' and 3' sensor strand overhangs. RNAi activation was unaffected by input mismatches to the 5' overhang but completely eliminated by mismatches to the 3' overhang (FIGS. 5c, 5f, and 10). Thus, only the 3' sensor overhang was functional as a toehold for strand displacement. In the MD simulations, strand displacement from construct I.1's 5' toehold would initially proceed towards the interior of the construct while displacement from the 3' toehold would proceed towards the exterior (FIGS. 1c, 1d). Thus, steric hindrance may play a role in preventing strand displacement from a 5' toehold. Other factors such as binding site accessibility on the RNA input or differences in base-pairing stability between the 5' and 3' toeholds may also contribute to preventing strand displacement from a 5' toehold.

Construct III.1 showed greater RNAi activation (FIG. 5f) than construct I.1 (Figure Sc) despite having a similarly potent ON state RNAi trigger (FIGS. 5b, 5e). A plausible explanation is that the greater thermodynamic stability of III.1's eight base 3' toehold results in faster strand displacement kinetics.

Figure 3B:
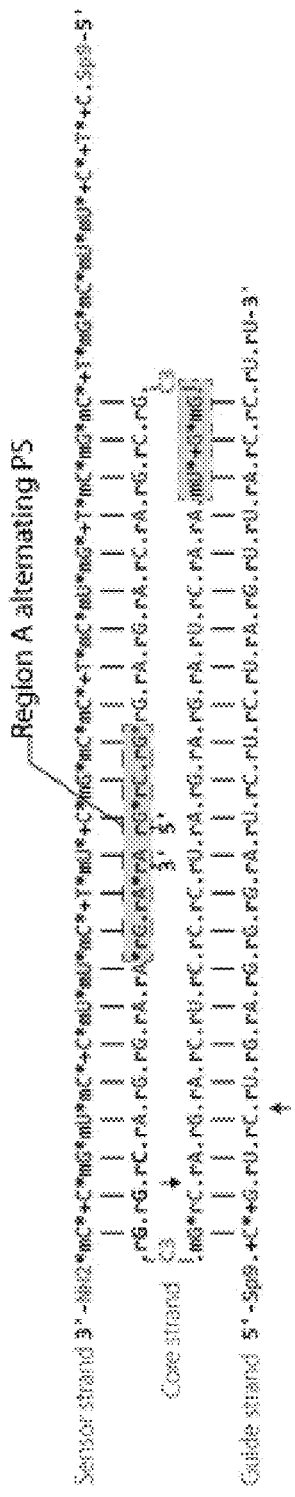
Figure 3B:
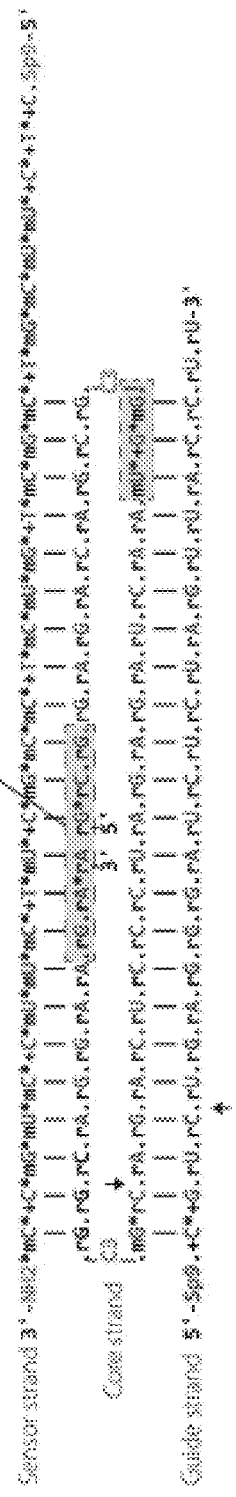
Figure 3C:
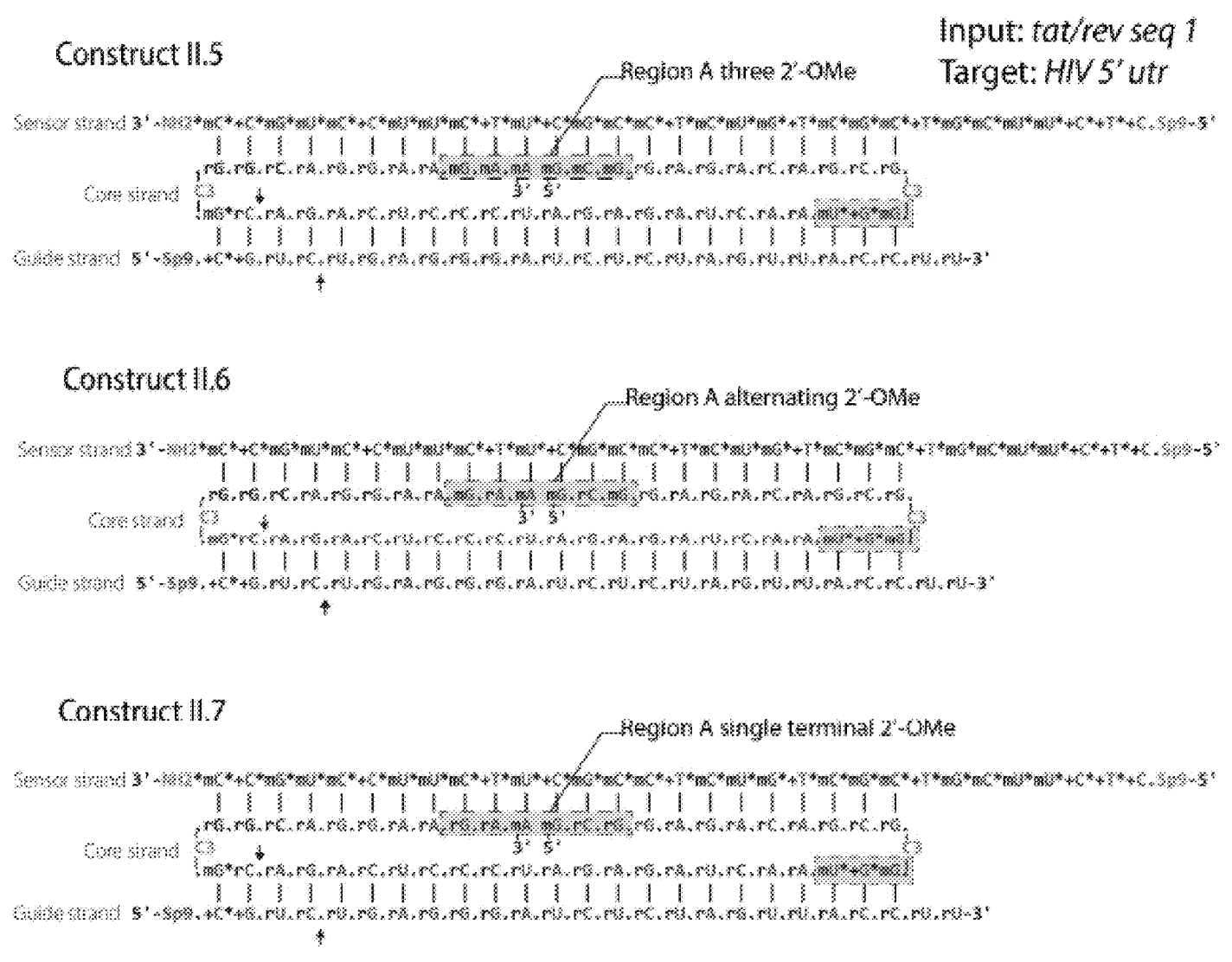
Figure 3D:
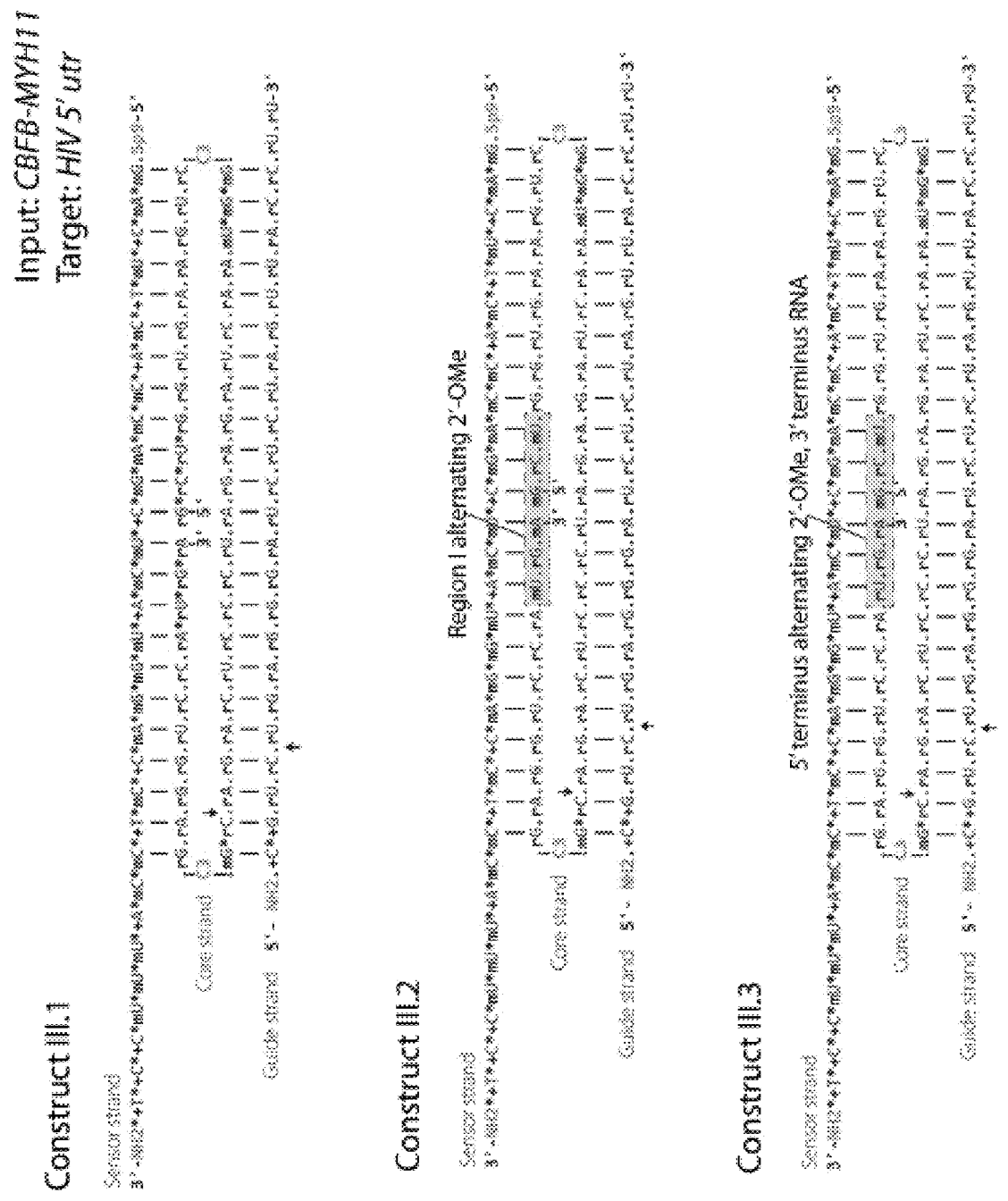
Figure 3E:
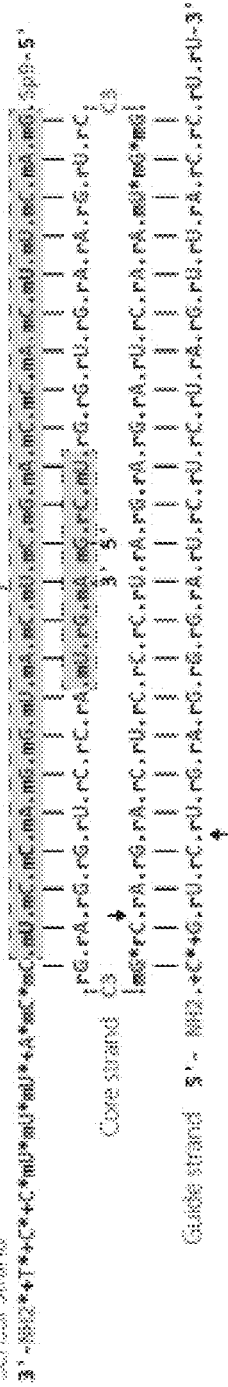
Figure 3F:
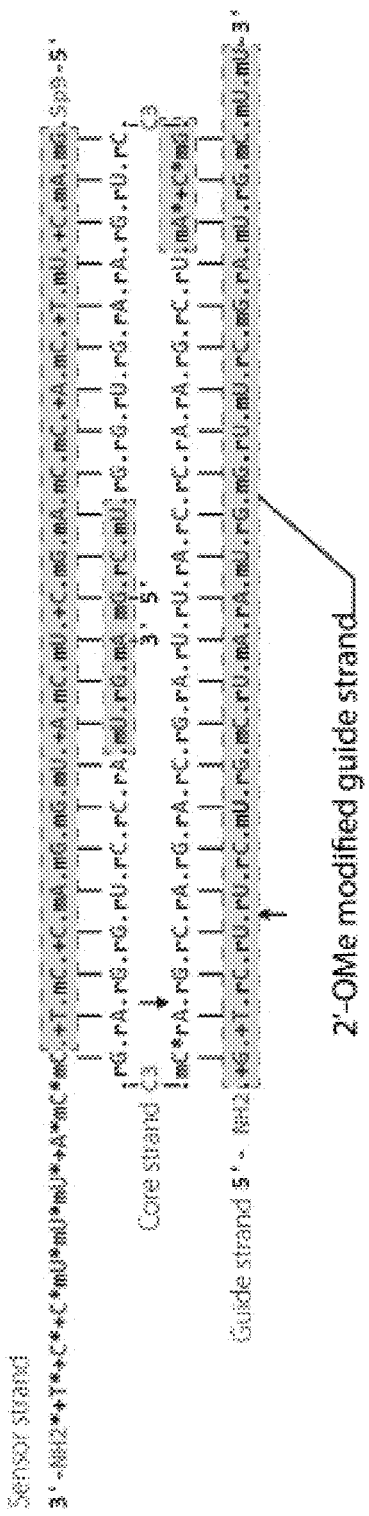
Figure 7:
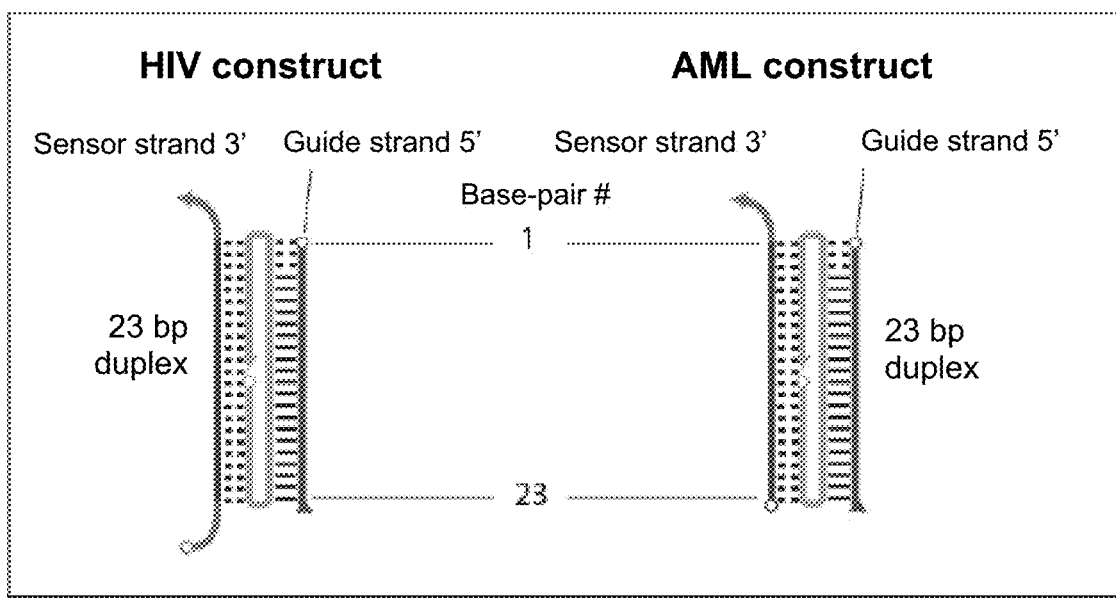
FIG. 7 shows that the base-pair parameters of 23 base-pairs in each helix was measured every 5 ps using x3DNA[43] and plotted as heat maps. Base-pairs were numbered from top (1) to bottom (23) in the orientation shown below. Base-pair parameter definitions are illustrated in the website x3dna.org/articles/seeing-is-understanding-as-well-as-believing.

Further optimization of chemical modifications in key areas of the construct were performed (FIG. 3a, highlighted areas). The OFF and ON state RNAi activities of construct II variants were measured (FIGS. 7, 8, construct II.1-5) with differing patterns of chemical modifications at the 3' and 5' termini of the core strand (FIG. 3b, region A, flanking the central nick in the sensor duplex) and in the exonuclease-blocking domain of the RNAi duplex (FIG. 3a, region B).

For region B, the results showed that that thermodynamic stability at the ends of the RNAi duplex may be important for suppression of OFF state RNAi activity. The replacement of a 2'-OMe modification in the center of the nuclease-blocking module with a locked nucleic acid (LNA) modification (FIG. 9c region C) reduced background RNAi activity without compromising RNAi potency (FIG. 5g, II.1 vs II.2).

For region A, to shut down OFF-state RNAi activity, the 3' and 5' termini of the core strand need to be protected by chemical modifications to shut down OFF-state RNAi activity. Background RNAi activity increased significantly when PS backbone linkages were replaced by phosphodiester linkages (FIG. 5g, II.2 had 3 consecutive terminal PS, II.3 had 2 alternating PS, II.4 had single terminal PS), and the ability to control RNAi activity was entirely lost with unmodified termini (II.0).

Figure 8A:
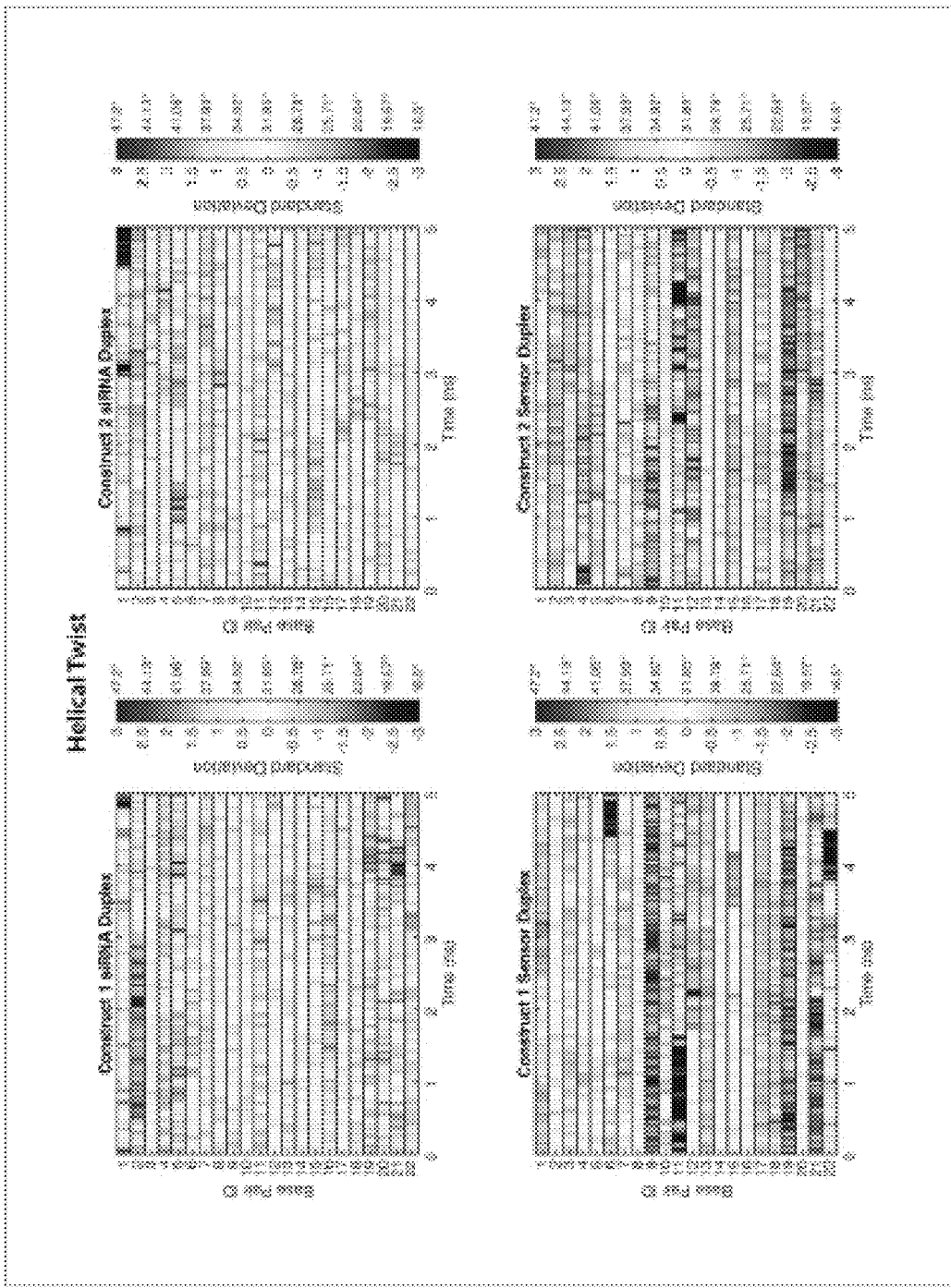
FIGS. 8a-8l show base-pair parameters from Molecular Dynamics simulations of sensor and siRNA duplexes over 5 nanoseconds. Shear (8g), buckle (8k), stretch (8i), propeller (8f), stagger (8h) and opening (8l) parameters are defined for base-pair 1-23. Shift (8e), tilt (8j), slide (8d), roll (8c), rise (8b), and twist (8a) parameters are measured for base-pairs 1-22 versus the succeeding base-pair. The heat scale for each measurement is centered on the average values measured over 5 ns control MD trajectories for four normal unmodified RNA duplexes with identical base sequences as the siRNA and sensor duplexes of the HIV and AML constructs. The heat scales span three standard deviations as measured from the same control trajectories. We observed significant deviations from normal RNA values for twist, rise, roll, slide, shift, and propeller measures (8a-8f). In these plots, construct 1 is the HIV construct, construct 2 is the AML construct.
Figure 8B:
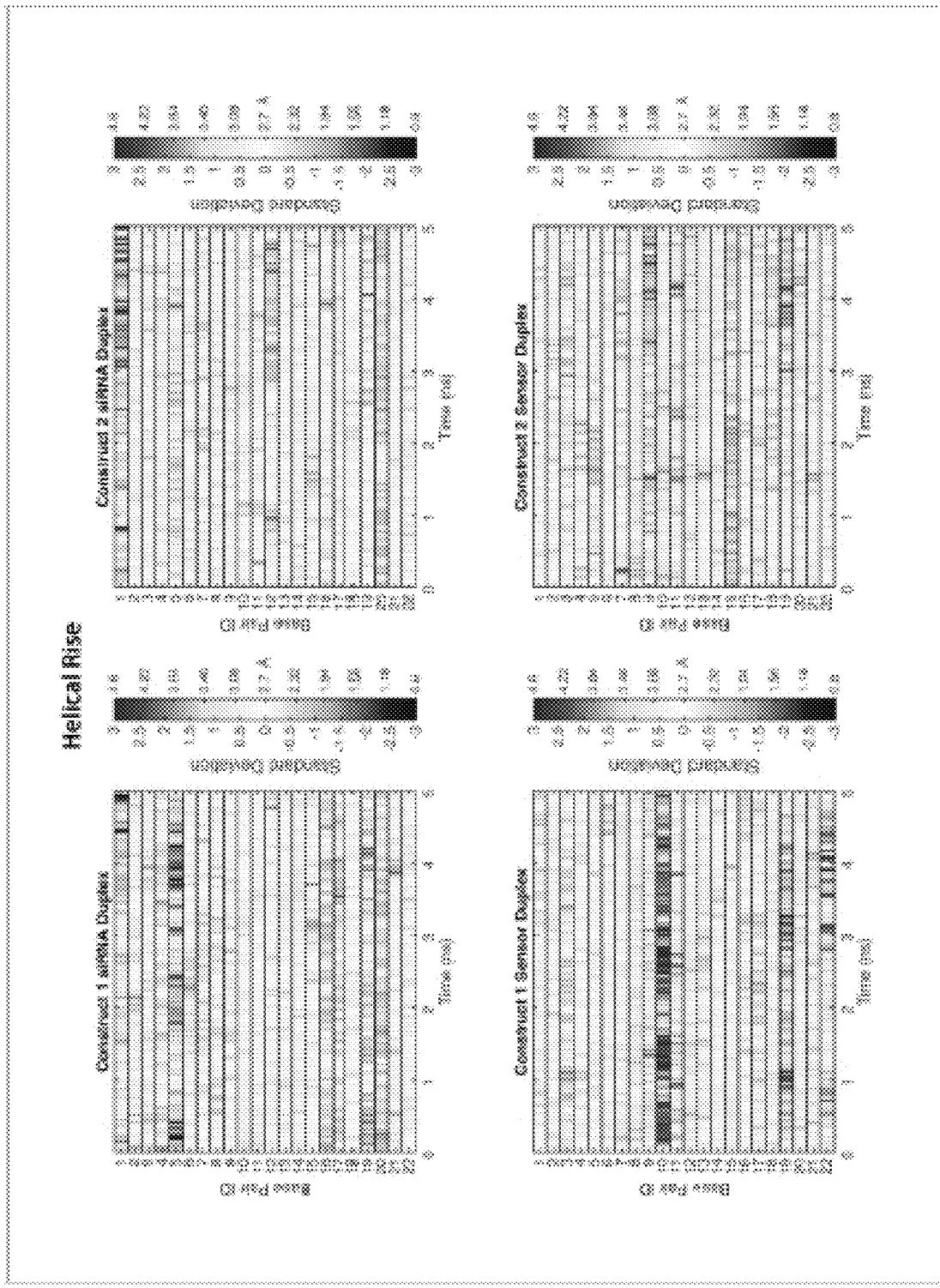
Figure 8C:
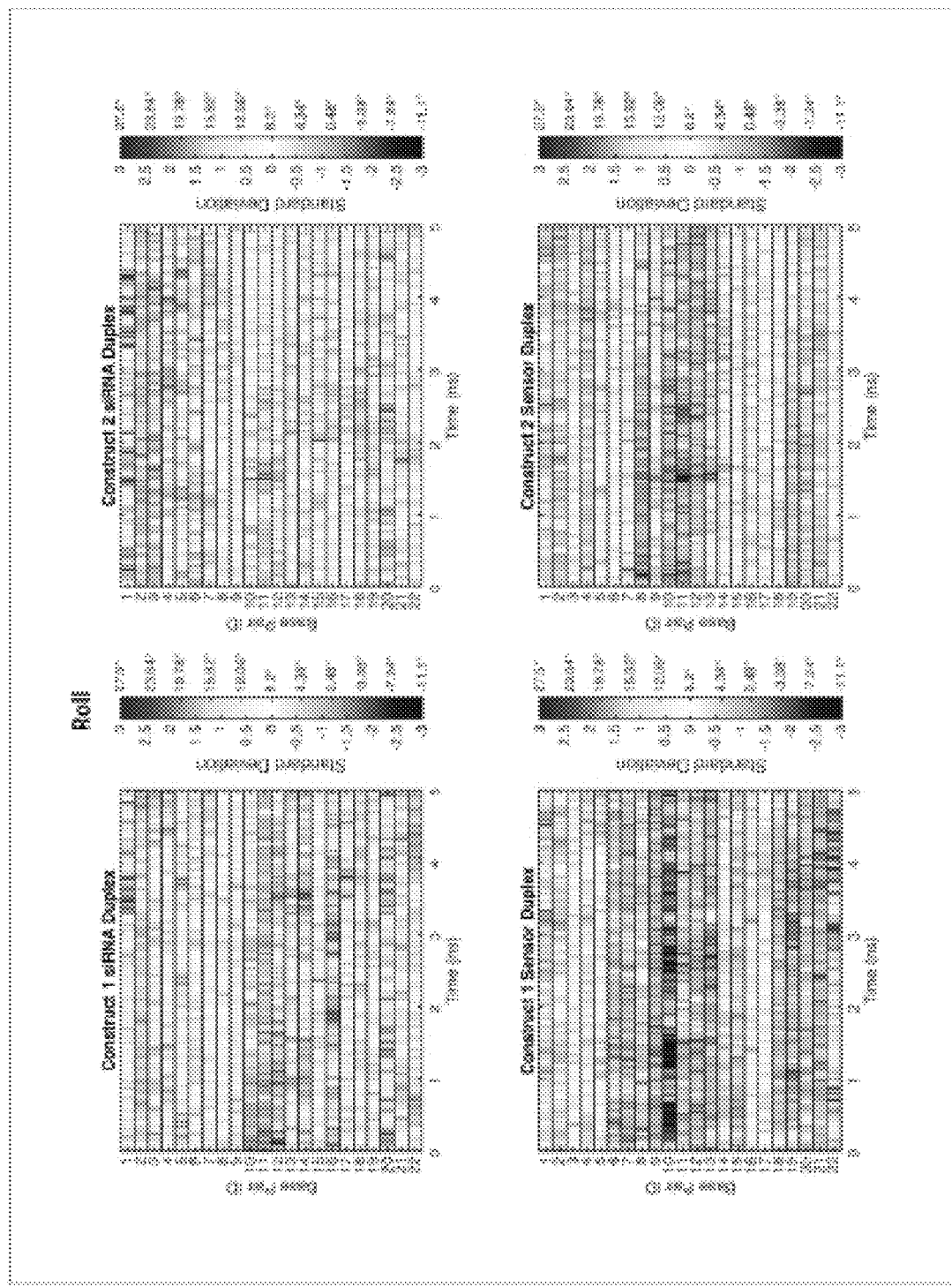
Figure 8D:
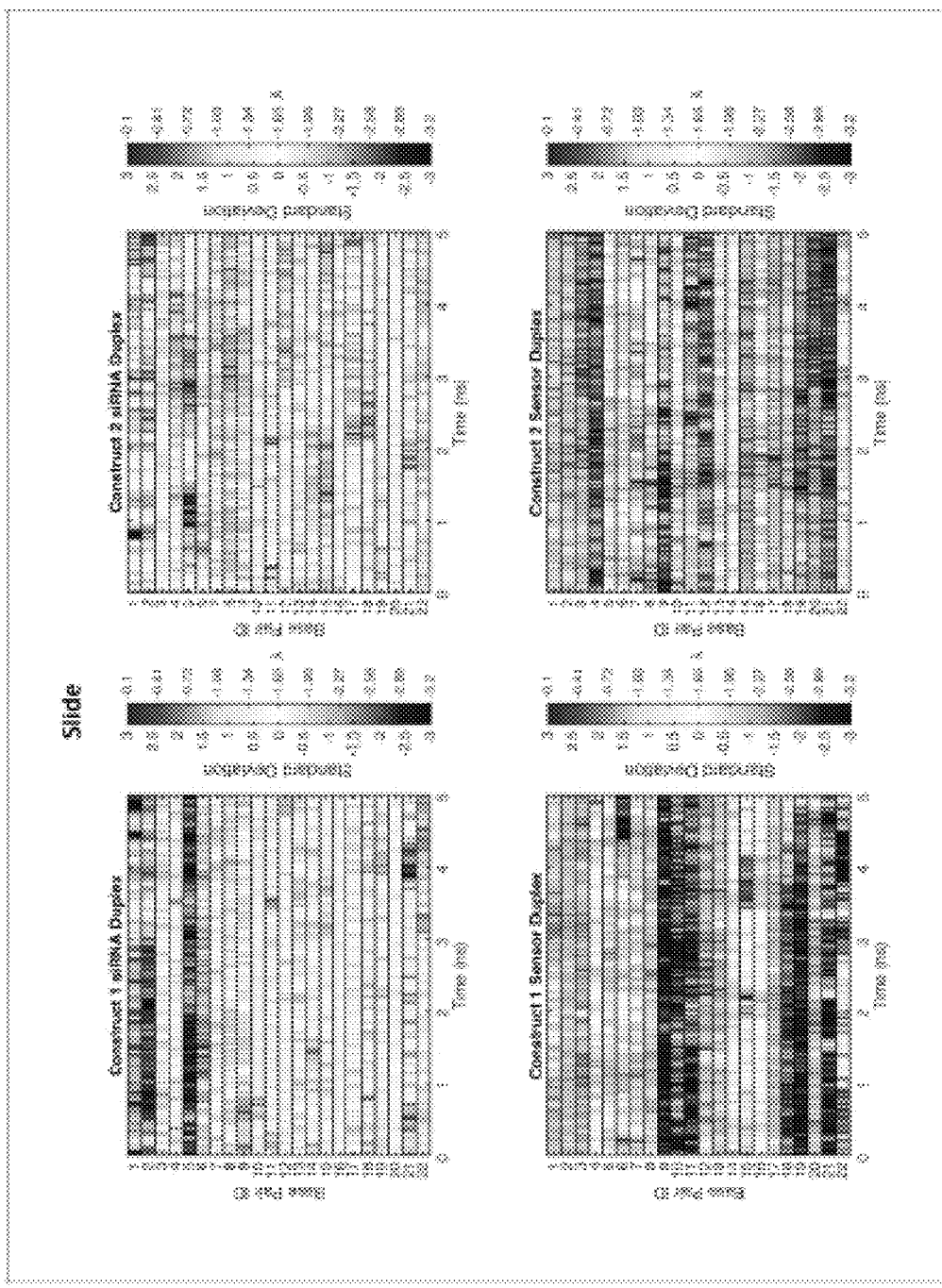
Figure 8E:

A problem with the use of PS linkages in region A is that each PS is a stereocenter with two possible enantiomeric conformations. Unfortunately, the more nuclease resistant Sp conformation is destabilizing to RNA base pairing[34]. To improve thermodynamic stability of the sensor duplex and reduce racemic heterogeneity, PS backbone modifications were replaced with 2'-OMe base modifications (FIGS. 5h, 8c constructs II.5-7). The use of three consecutive (II.5), two alternating (II.6), or one terminal (II.7) 2'-OMe base at each core strand terminus all significantly reduced background RNAi activity. Furthermore, all three motifs increased ON state RNAi potency over PS modified analogues (FIG. 5h, II.5-7 vs II.2, ON state).

To determine whether 2'-OMe modifications allowed RNAi activation by cellular RNA transcripts, RNAi activation for II.1, II.2, II.6, and II.7 was compared (FIG. 5i) using a two-step transfection protocol. Both II.6 and II.7 showed significantly reduced background RNAi activity, rejected activation by mismatched RNA transcripts, and exhibited increased RNAi knockdown of the Renilla luciferase target in cells that expressed sequence matched inputs for the sensor (FIG. 5i, ~50% reduction in target expression at 2 nM Cond-siRNA concentration).

To test the general applicability of region A optimizations, a version of construct III with 2'-OMe protected core strand termini was created (FIG. 8d, III.2) and its activation by cellular RNA transcripts was tested (FIG. 5j). Compared with the original PS protected variant (III.1), III.2 had significantly reduced background RNAi activity in cell expression mismatched inputs and better RNAi activation in cells expressing correct inputs (FIG. 5j, III.1 vs III.2). Notably, the removal of the terminal 2'-OMe modifications from just one of the core strand termini (III.3, the 3' overhang of the core strand) nearly abolished control over RNAi activity (FIG. 5j, III.3).

Figure 5K:
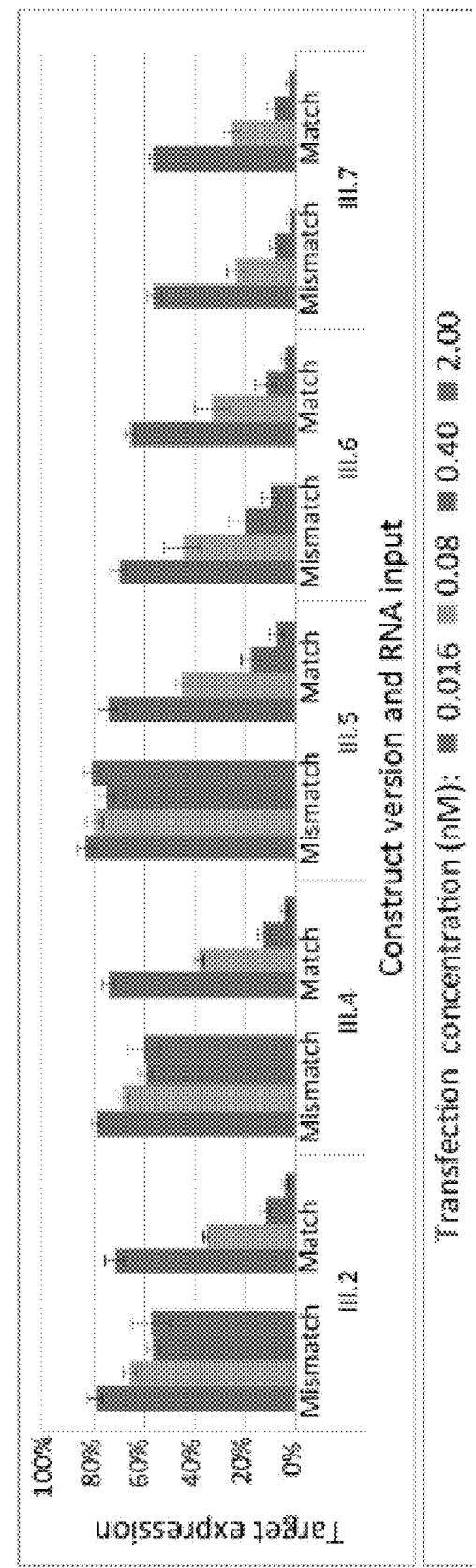

Having optimized the core strand, the sensor strand is also improved. The initial constructs (I.1, II.1, III.1) used fully modified sensor strands with PS, LNA and 2'-OMe modifications in all regions. PS modification in the duplex region of the sensor may increase spurious activation by reducing base pairing stability. Also, other researchers have used 2'-OMe modifications alone without LNA to stabilize strand displacement switches for operation in mammalian cells[8,19]. Disclosed herein a series of construct III variants that combined a 2'-OMe protected core strand (region A) with sensor strands that had either LNA+2'-OMe+PS (FIGS. 5k, 8e, III.2, III.4), LNA+2'-OMe (III.5), 2'-OMe only (III.6), or no modifications (III.7) in the duplex region of the sensor strand were tested. The results showed that the RNA (III.7) and 2'-OMe only (III.6) versions of the sensor strand were unable to suppress unintended RNAi activity (FIG. 5k). The most optimal variant was III.5, which had LNA and 2'-OMe modified bases, but no PS modifications in the duplex region. At 2 nM Cond-siRNA concentration, construct III.5 had only 20% background RNAi activity in cells expressing mismatched RNA inputs and achieved more than 90% knockdown of the *Renilla* target in cells expressing the correct RNA inputs (~10× reduction in target expression between matched and mismatched). Statistically significant RNAi activation could be seen down to only 80 pM of Cond-siRNA.

Figure 8F:
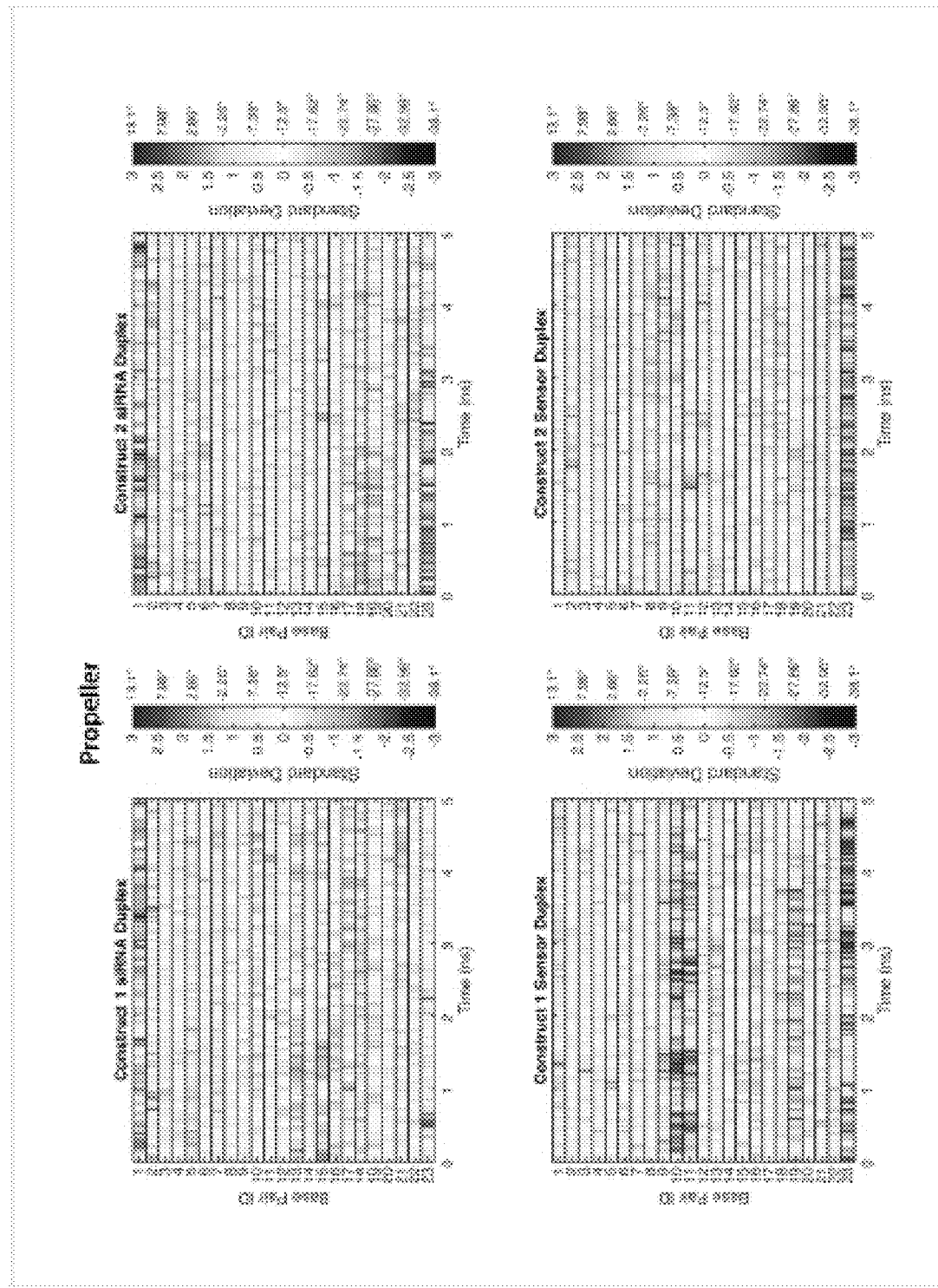
Figure 8G:
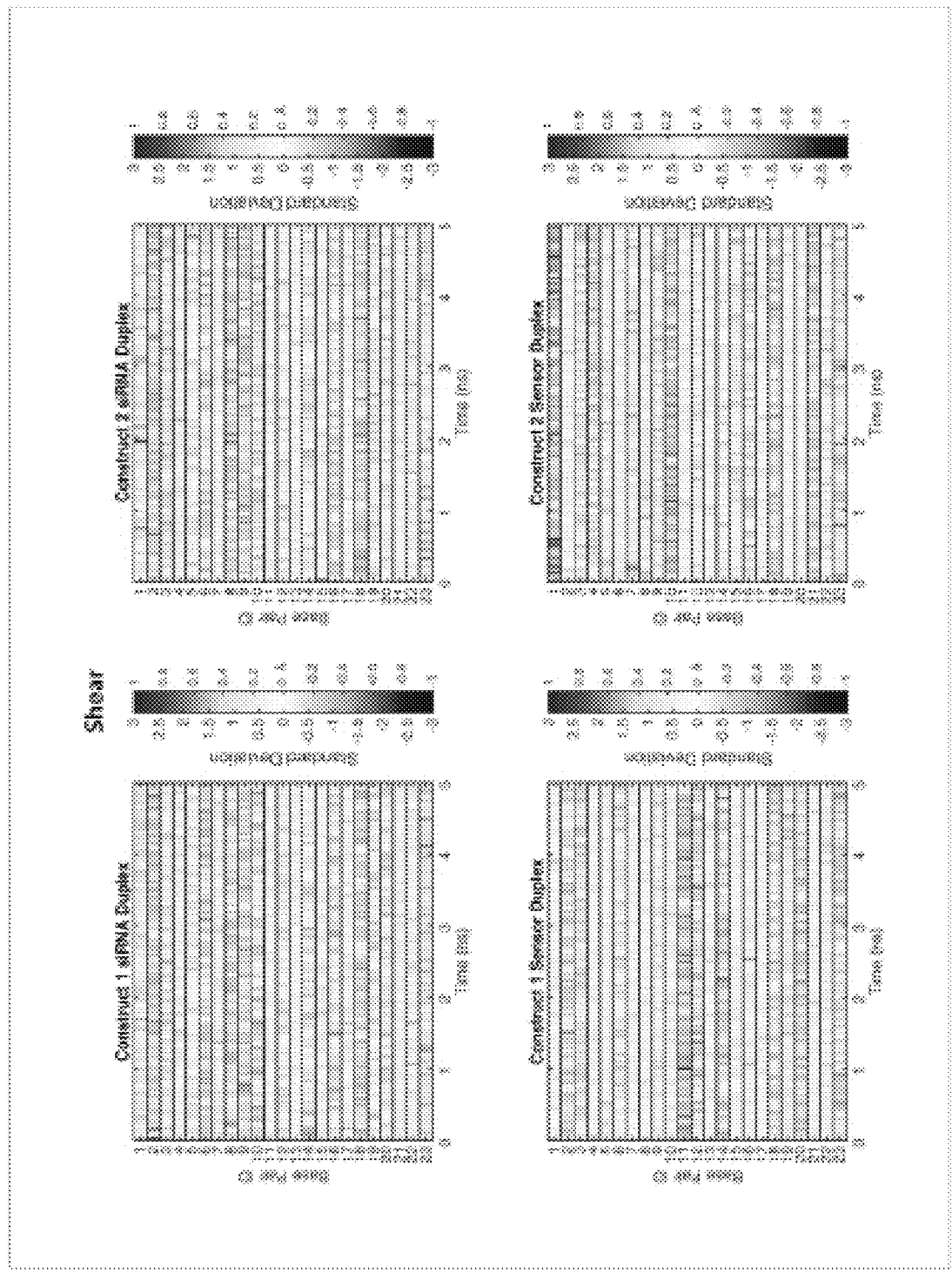
Figure 8H:
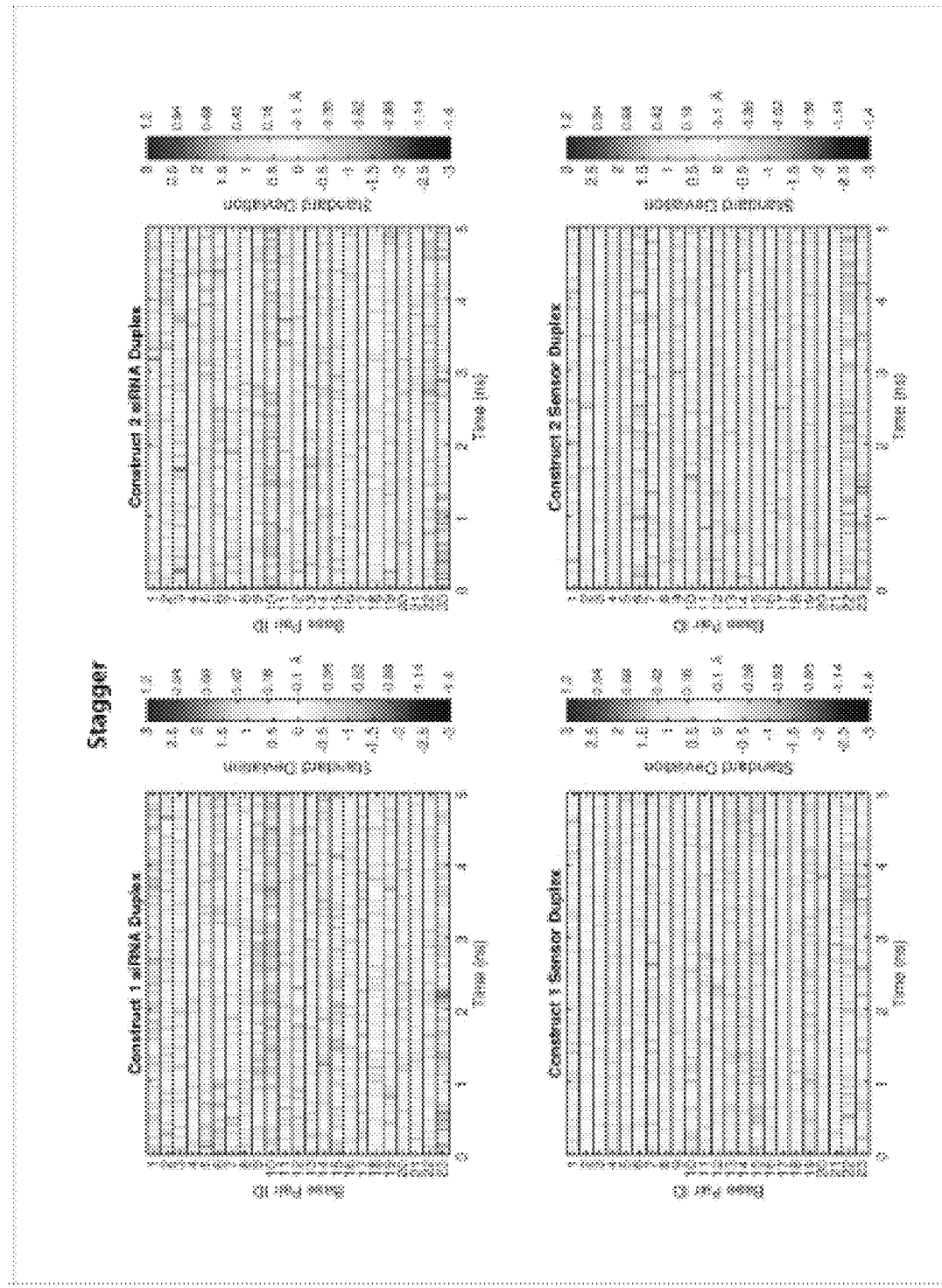
Figure 8I:
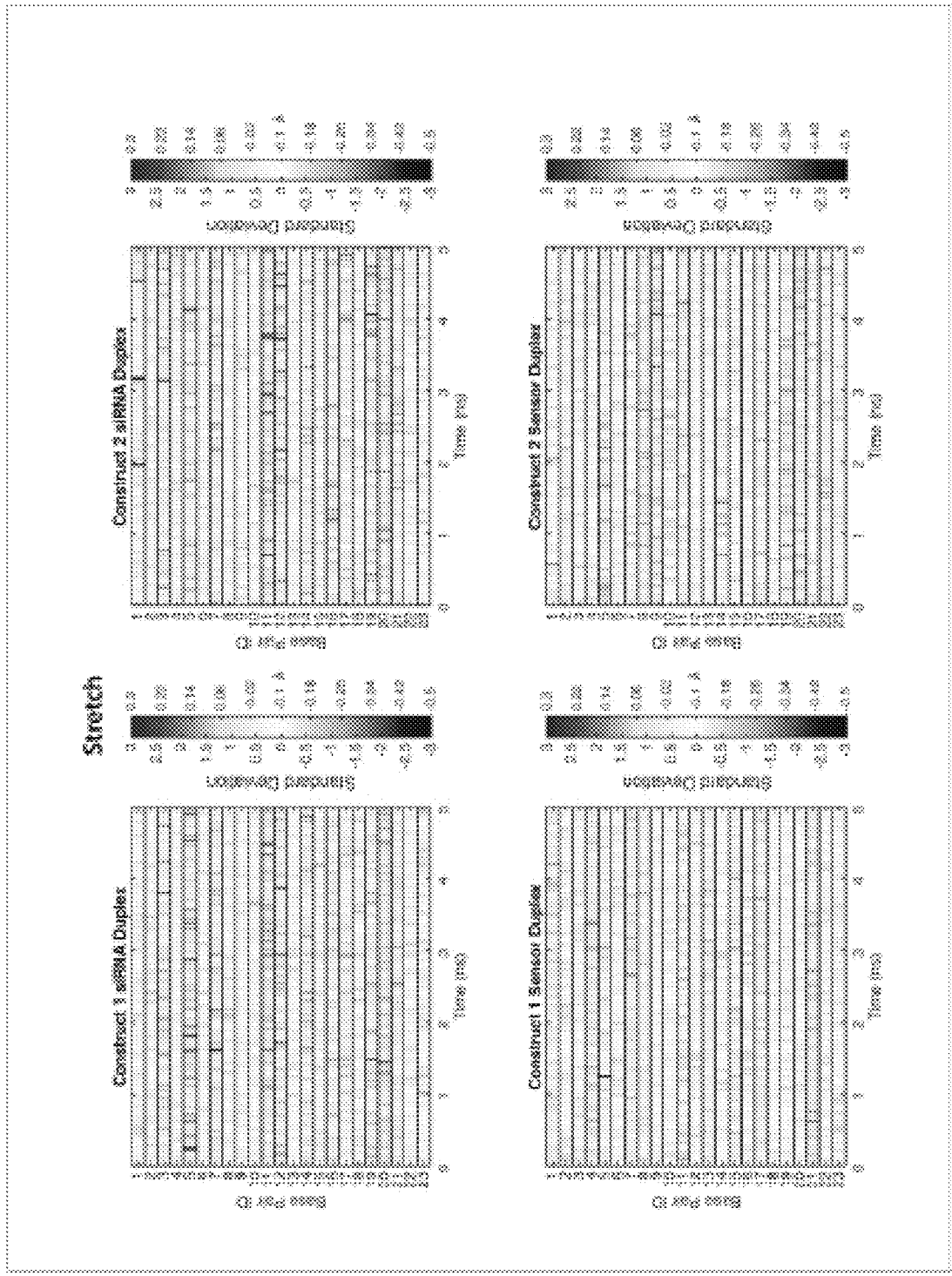
Figure 8J:
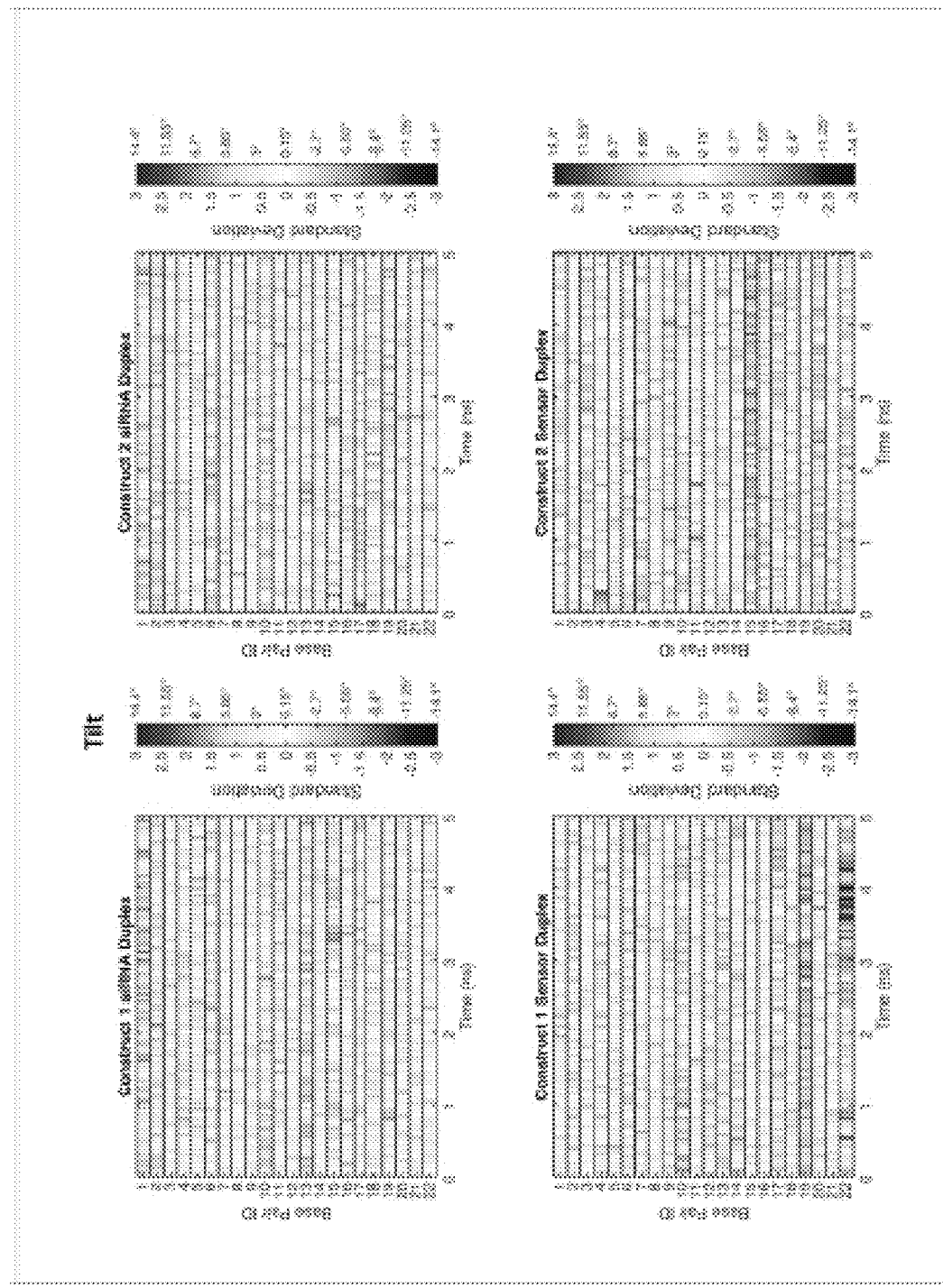
Figure 8K:
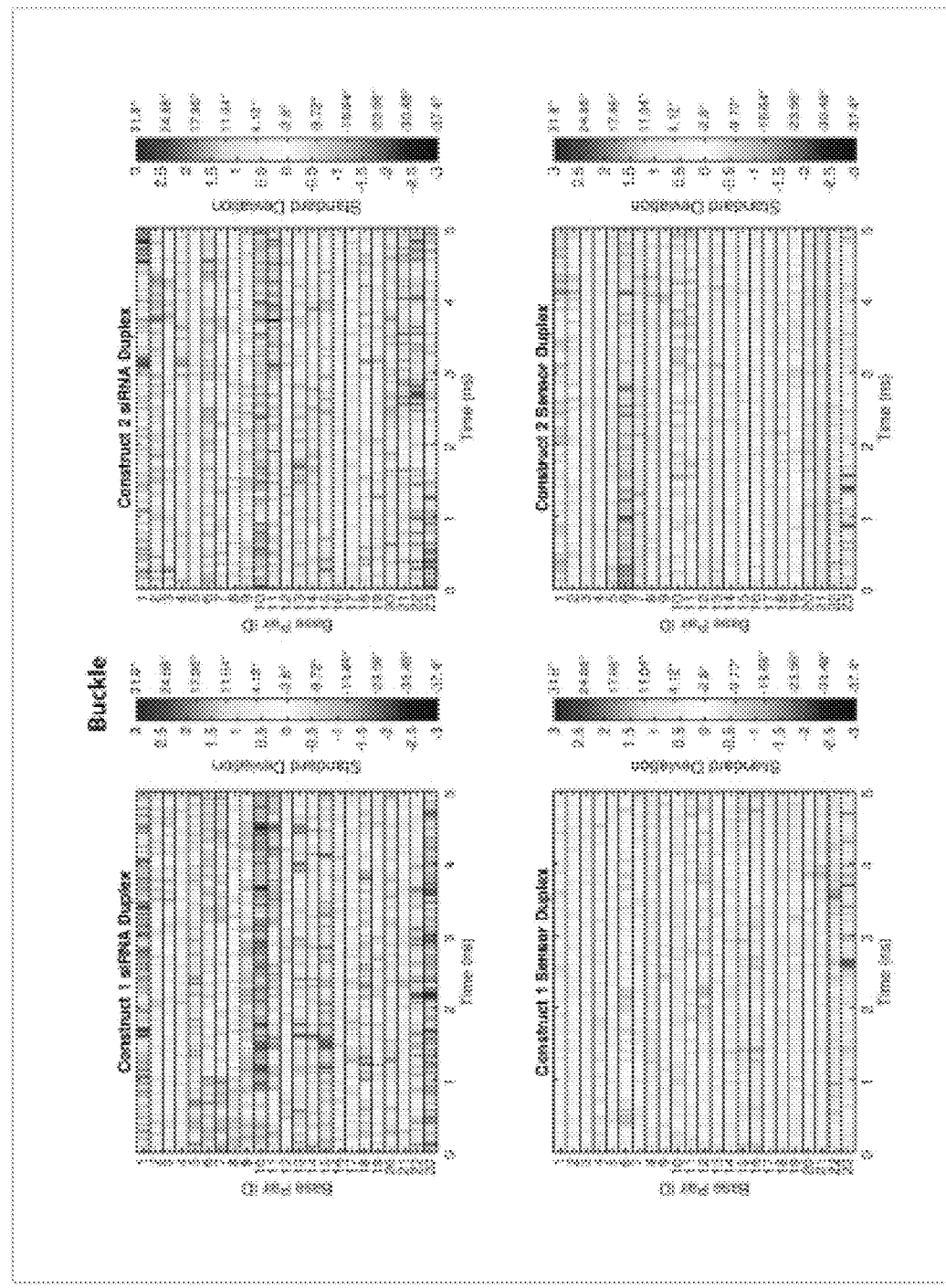
Figure 8L:
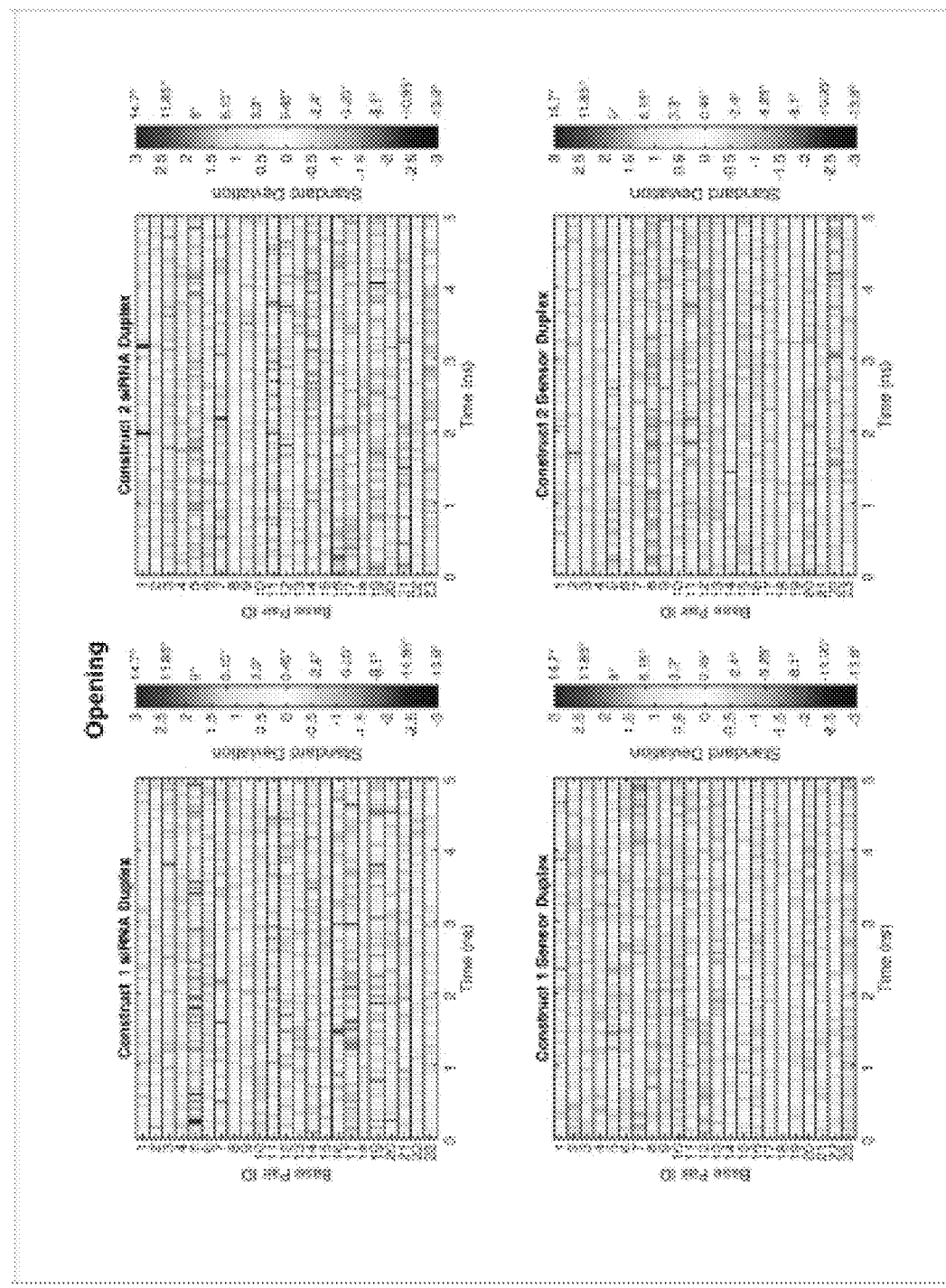
Figure 9A:
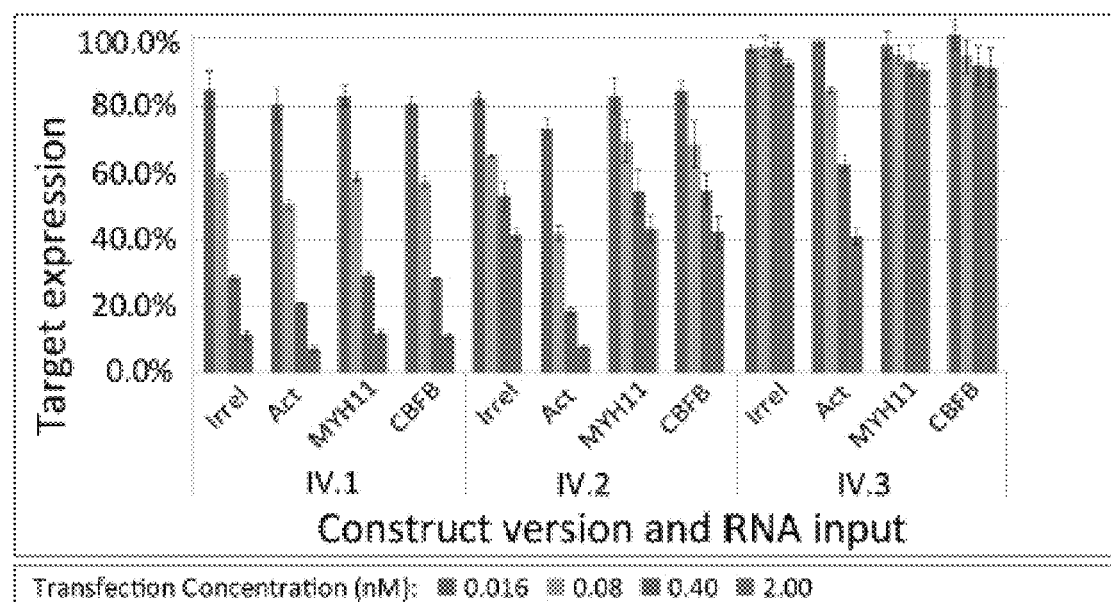
FIGS. 9a-9c (SEQ ID NOS: 70-72) show RNAi activity, sensor design, and sequence of CBFP-MYH11 sensing, MCL-1 targeted Cond-siRNA.
Figure 9B:
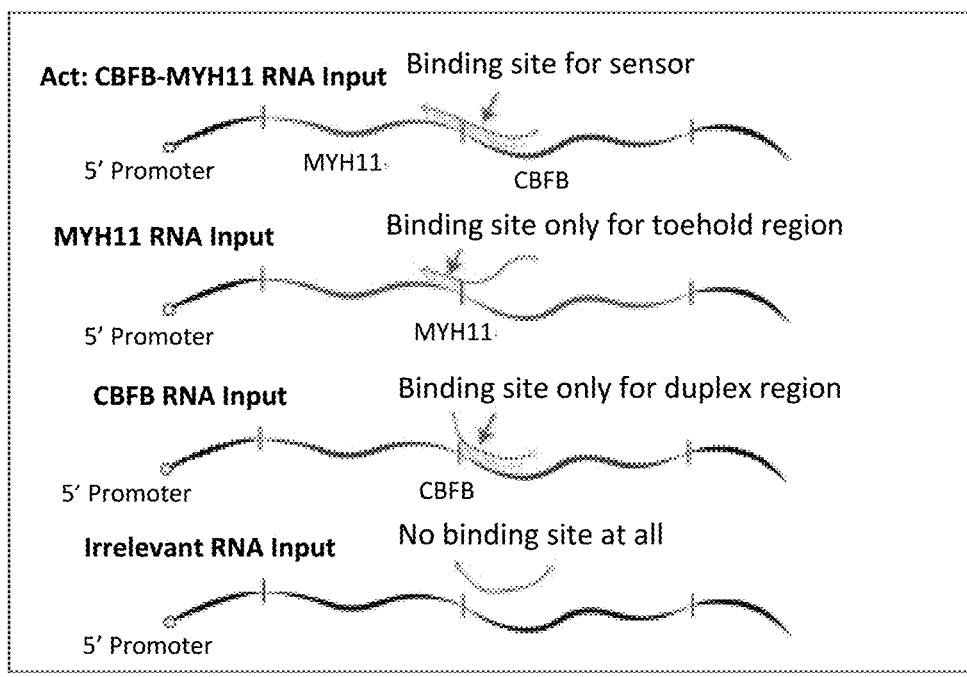
Figure 9C:
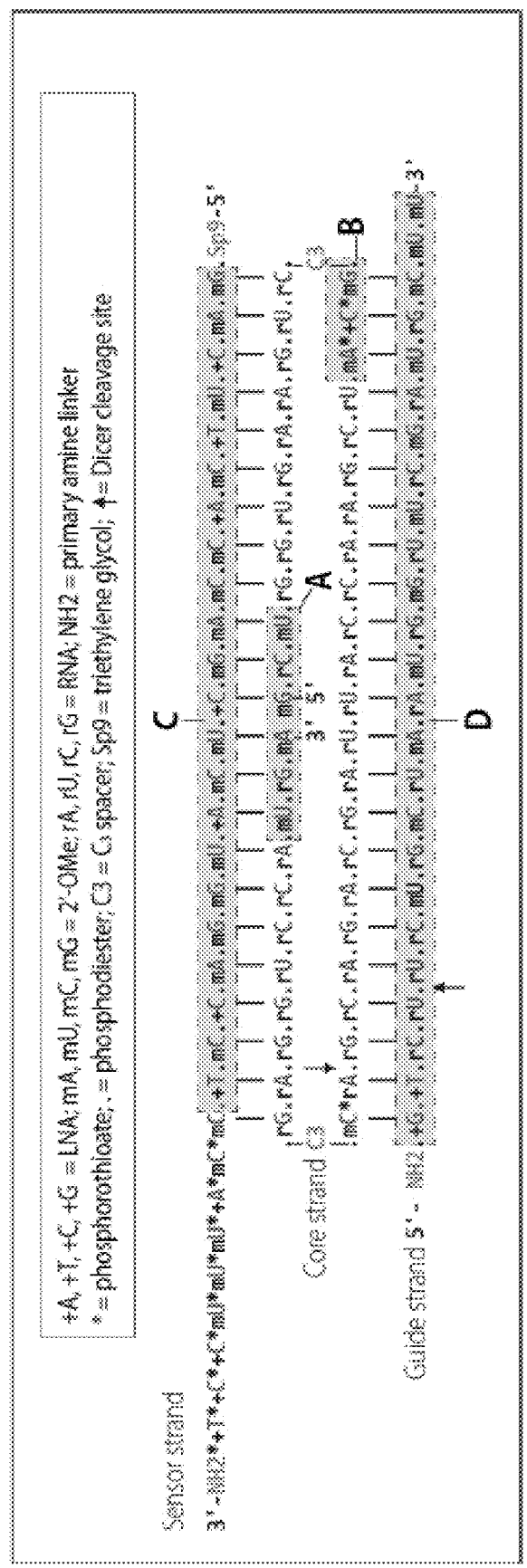

Using insights gained from optimization of the CBFB-MYH11 sensor for construct III, construct IV was developed. Construct IV is a CBFB-MYH11 sensing Cond-siRNA with an RNAi domain targeting MCL-1, an endogenous apoptosis inhibitor that is crucial for the survival of AML cells[35] (but not the HCT116 cells used for dual luciferase experiments). Three versions of construct IV were tested for RNAi activation in response to transcripts with CBFB-MYH11, CBFB, or MYH11 sequences. To ensure that the sensor activates on the fusion sequence, the sensor strand (same as used in construct III) was designed to be complementary to the MYH11 sequence in its toehold forming region and complementary to the CBFB sequence in its duplex region (FIG. 9b). Three versions of construct IV were tested (FIG. 8f). IV.1 had modification patterns analogous to prototype construct III.1; construct IV.2 had optimized region A, B, and sensor strand motifs. IV.3 had additional 2'-O-methyl modifications in the guide strand using patterns previously found to have small impact on RNAi potency[36]. Surprisingly, both IV.2 and IV.3 had significantly improved suppression of background RNAi activity and improved RNAi switching compared to IV.1 (FIG. 9c). IV.2 had background RNAi leading to ~60% reduction in the *Renilla* readout target at 2 nM of Cond-siRNA but showed ~90% reduction in *Renilla* in the fusion sequence expressing cells. IV.3 had almost no detectable background RNAi, but also lower activated RNAi activity (~60% reduction in *Renilla* at 2 nM).

In some embodiments, the chemical modifications of the Cond-siRNA construct disclosed herein include one or more of the following:

A. The use of a sensor strand where the highlighted region C in FIG. 3a, "Regions for screening of chemical modifications" has one or more of the following features:
   a. 50% or less of the backbone positions are phosphorothioate (PS) connections.
   b. 50% or more of the bases are chemically modified to resist nuclease degradation or increase the melting temperature of the duplex (Tm)
   c. 100% of the bases are chemically modified to resist nuclease degradation and increase Tm
   d. About 10%-50% of the bases are locked nucleic acid (LNA) or other chemically modified base with 2'-4' bridging modifications that substantively increase the Tm.

B. The 5' and 3' termini of the core strand have one or more of the following features:
   a. The terminal base on the 5' is a 2'-F, 2'-O-methyl, or other modified base that resists nuclease cleavage
   b. The terminal base on the 3' is a 2'-F, 2'-O-methyl, or other modified base that resists nuclease cleavage
   c. The three terminal bases on the 5' have the pattern MRM, where M is a modified base (2'-O-methyl, 2'-F), and R is an RNA base
   d. The three terminal bases on the 3' have the pattern MRM, where M is a modified base (2'-O-methyl, 2'-F), and R is an RNA base
   e. The three terminal bases on the 3' and 5' do not have consecutive PS backbone modifications
   f. The portions of the core strand that are base-paired with the sensor strand have an alternating chemical modification pattern (MR)n
   g. The above where M is a chemically modified base that does not decrease Tm of the duplex when compared to the equivalent RNA base
   h. Any combination where both the 5' and the 3' ends of the core strand have at least one of the features from a-g
   i. The 3' and 5' regions of the core strand that are base-paired with the sensor strand are:
      (a) Entirely made out of the pattern (M)n, where M is a 2'-O-methyl or 2'-F modified base, or
      (b) at least 50% of the bases in this area are 2'-O-methyl or 2' F and, up to 30%, 50%, 80% or 100% of the backbone connections are not phosphorothioate.

C. A core strand where the three bases base-paired with 3' terminus of the guide strand have one or more of the following features:
   a. A M*+*M pattern, where M is a 2' modified base (e.g. 2'-O-methyl or 2'-F), * is a PS backbone connection, and + is an LNA base or other 2'-4' bridged base
   b. A M*+*+ pattern, as defined above
   c. A +*+*+ pattern
   d. A R*+*M pattern, where R is an RNA base
   e. A R*+*+ pattern
   f. A +*M*M pattern
   g. The patterns in a-f, where * can be either a PS backbone connection or an unmodified (phosphodiester) backbone connection D. A guide strand with one or more of the following features:
   a. 30% to 95% of the bases are chemically modified bases (2'-O-methyl, 2'-F, LNA, 2'-4' bridged bases)
   b. Where the two terminal bases on the 5' are chemically modified c. Where the two terminal bases on the 5' have at least one LNA
d. Where the two terminal bases on the 5' are connected by a PS backbone
e. Where the two terminal bases on the 3' are both chemically modified
f. Where ~5% to 50% of backbone connections are PS
g. Where the bases flanking the indicated site of Dicer cleavage are not chemically modified.

In sum, disclosed herein is a programmable, conditionally activated small interfering RNA (Cond-siRNA). This device outputs an active RNA interference trigger against a target gene only upon detection of RNA transcripts from a different input gene. The improved performance of strand displacement sensors and realization of conditionally activated RNAi are attributable in part to five key design principles.

Figure 11:
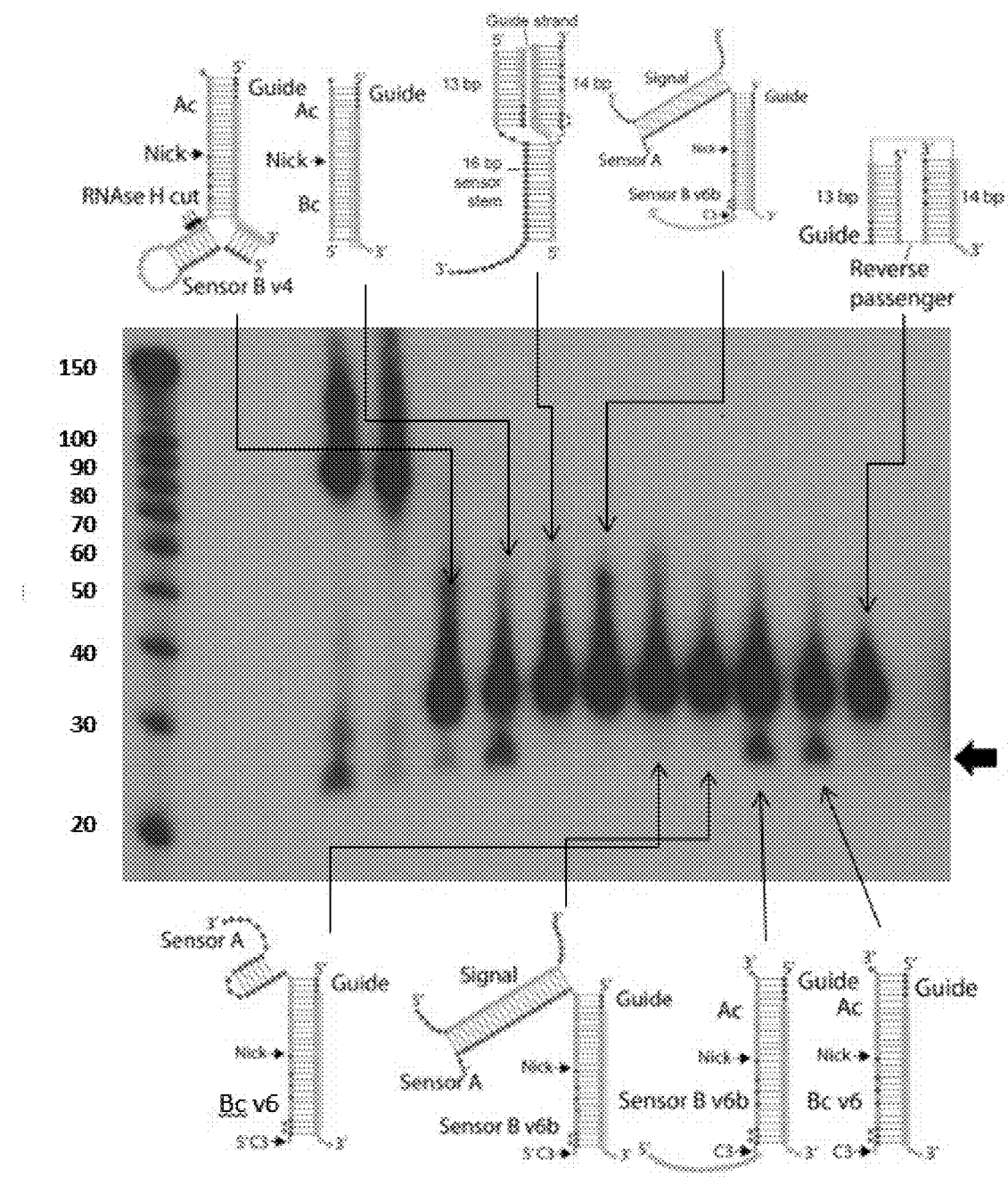
FIG. 11 shows the Northern blot of various prior generation RNAi trigger designs transfected at 1 nM concentration into HCT116 cells for 24 hours. The secondary structure of the triggers is diagramed. Green bubbles indicated 2'-O-methyl RNA bases. Blue bubbles indicate DNA. White bubbles indicate RNA. Black arrow indicates Dicer product. Results show that duplex RNA with adjacent 2'-O-methyl modified duplexes had reduced Dicer products.

First, the RNAi trigger needs to completely dissociate from the waste duplex formed by the input RNA and the sensor strand in order to have potent RNAi activity. Prior schemes for conditional RNAi often featured activated RNAi triggers that remain attached to the input signal (e.g. an mRNA) via Watson-Crick base pairing[15,17,18,37,60]. During development of a prior generation conditional RNAi trigger, it was found that the connection of Dicer substrates to adjacent 2'-O-methyl modified duplex RNA domains significantly reduced RNAi activity (FIG. 11). A possible cause for this could be binding of a Dicer inhibiting protein such as PACT[38] to the extended duplex. However, dissociation of the RNAi duplex from the input-sensor duplex was necessary for achieving simultaneous optimization of OFF state RNAi suppression and ON state RNAi potency.

The sequences used for the constructs in FIG. 11 are as follows:

Second, past designs for conditional RNAi triggers and other DNA circuits have featured either single-construct[15,16] or multi-construct[17] schemes for translating an input sequence into an independent output sequence. Single-construct translators should theoretically be intrinsically more efficient in signal detecting and transduction. However, the disadvantage is that the RNAi trigger must be concealed within the construct, creating an opportunity for spurious RNAi activation due to construct degradation. The success of the disclosed Cond-siRNA design indicates that the advantages of single-construct translators can be utilized while the risk of spurious activation effectively controlled.

Third, extensive chemical modifications are key to proper functioning of strand displacement sensors, and by extension, the Cond-siRNA. The working examples of the optimization experiments show that: 1) the duplex domain of the sensor strand needs to have both LNA and 2'-O-methyl modifications but not PS modifications; 2) the termini of the protecting strand need to be modified with either PS or 2'-O-methyl; 3) thermodynamically stabilizing modifications generally improve suppression of background activation, while thermodynamically destabilizing modifications such as PS backbones can actually increase spurious activity when used extensively in duplex regions; 4) while the chemical modifications were not tested in the toehold domain, the combination of LNA, 2'-O-methyl and PS modifications are beneficial, as they improve the base-pairing affinity and nuclease resistance of the single stranded overhang.

Fourth, the endogenous RNA degradation machinery can be an effective tool for construct switching. As shown in the working examples, the chemically modified 3' and 5' terminal regions of the core strand were highly stable when base-paired with the sensor strand but vulnerable to degradation when unpaired. This differential susceptibility to nuclease activity can be accomplished with PS modified termini but appeared more effective with 2'-OMe modifications. As demonstrated herein, the degradation of single stranded overhangs can be stopped at the ends of duplexes

TABLE 4

Sequences for Testing Constructs

| | | SEQ ID NO |
|---|---|---|
| Guide | mCmUmUmGCGUCUGAGGGAUCUCUAGUUACCUU | 93 |
| DNA probe for guide strand | dAdAdGdGdTdAdAdCdTdAdGdAdGdAdTdCdCdCdTdCdAdGdA | 94 |
| Sensor A | CCUCAGACGCAAGmCmUmGmAmUmGmAmGmCmUmCmUmUmCmGmUmCmG*mC*mU*mG*mU*mC*mU*mC(18s)(idT) | 95 |
| Ac | CCUCAGACGCAAG(idT) | 96 |
| Sensor B v6b | CGACGAAGAGCUCAUC(c3)mG*mG*mUAACmUAmGAmGAUmC | 97 |
| Sensor B v4 | mAmAmGmGmUdCdCdCdTdGdAdTCGACGAAGAGCUCAU CAGGGUAAC mUAmGAmGAUmC | 98 |
| Bc | GGUAACUAGAGAUC | 99 |
| Bc v6 | (c3)mG*mG*mUAACmUAmGAmGAUmC | 100 |
| Signal | mAmAmAmAAGCGGAGACAGCGACGAAGAGCTCATCA GmAmAmAmA mA | 101 |
| Reverse Passenger | CCUCAGACGCAAGGGUAACmUAmGAmGAUmC | 102 | by exonuclease blocking domains. The trimming of the disclosed RNAi duplex using this scheme resulted in a potent RNAi trigger from the DX secondary structure. Similar schemes might be useful in the dynamic reconfiguration of other nucleic acid nanostructures.

Finally, the separation of the sensor and RNAi domains in two distinct duplexes was important for intracellular stability, programmability and ease of engineering development. First, there is no base-pairing overlap between the two domains and no competing secondary structure conformation. This ensured a large margin of thermodynamic stability and simplified programming for new input and output sequences. Second, the dimensions of the duplexes and the linkage chemistry at the crossover points were configured to minimize strain in the tertiary structure (FIG. 1c). This further enhanced the thermodynamic stability. Third, since the duplexes did not overlap, chemical modifications can be applied to the sensor domain without compromising compatibility of the RNAi domain.

The following examples are provided to better illustrate the claimed invention and are not to be interpreted as limiting the scope of the invention. To the extent that specific materials are mentioned, it is merely for purposes of illustration and is not intended to limit the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

Example 1: Construct Design

Cond-siRNAs were designed for specific pairing of inputs and targets using an iterative protocol. A suitable 21-nt guide strand sequence for the RNAi domain was obtained from previously validated siRNAs, literature sources, or siRNA design tools. A 23-bp Dicer substrate was created from the chosen guide strand by adding four G/C rich bases to the 5' of the guide strand. Nupack (RNA strand, parameters disclosed by Mathews[59], some dangle treatment) was used to confirm that the RNAi duplex forms with >95% probability at 1 nM of guide (antisense) and sense strands.

From the sequence of the input biomarker, a list of all possible 31 to 33 nt sensor segments (antisense to the input) was generated. For the CBFP-MYH11 fusion sequence, only sensor segments that approximately met parameters illustrated in FIG. 9b were considered. Sensor sequences were ranked for uniqueness in the transcriptome of the target animal using NCBI BLAST. For human cancer cell lines, sequences were checked against human transcript+genomic collection using the BLASTn algorithm. Where possible, sensor segments that have more than 17 bases of sequence complementarity and complete overhang complementarity to known or predicted RNA transcripts were eliminated.

Starting with the most unique sensor segments, construct core strand sequences in accordance with desired structural parameters for the Cond-siRNA were selected. For example, core strands had sequences of the form 5'-B-C3-P-C3-A-3' where A and B are complementary to the 5' and 3' ends of the sensor strand's putative duplex domain, P is complementary to the putative guide strand, and C3 are C3 linkers. Nupack was used to rank the thermodynamic stability of the duplexes formed between sensor strand segments and their corresponding 5' and 3' core strand overhangs. RNA strand having parameters disclosed by Mathews et al.[59] was used with some dangle treatment. Ideally, >95% of strands should be base-paired at 1 nM strand concentration. The core strand was also checked to confirm that it did not have heavy internal secondary structure.

The best constructs having the guide strand, core strand and sensor strand sequences designed above were chosen and subjected to chemical modifications. Exiqon's oligonucleotide design tools (www.exiqon.com/oligo-tools) were used to optimize the placement of LNA modifications. LNA modifications were added to the sensor strand approximately 1 per every 3 to 4 bases. The LNA Oligo Optimizer tool was used to check that the LNA pattern did not lead to secondary structure or self-pairing interactions with scores higher than 60. Self-complementarity and self-pairing scores were optimized to the extent possible.

Example 2: Synthesis of Strands

Strands with LNA bases were synthesized by Exiqon Inc (now a division of Qiagen). Strands without LNA were synthesized by GE Life Sciences Dharmacon (now a division of Horizon Discovery Group). All strands were ordered with PAGE or HPLC purification, according to recommendations by the manufacturer.

Example 3: Assembly of Cond-siRNAs

Cond-siRNAs were assembled by thermal annealing in 1× phosphate buffered saline (PBS). Constructs can be assembled with or without purification. Assembly quality can be assessed using non-denaturing gel electrophoresis on 10% to 15% PAGE in 1×TBE at 4° C.

For assembly without purification, sensor, core and guide strands were mixed at a 1.1 to 1.00 to 1.1 molar ratio at 50 nM or 100 nM concentration in 1×PBS pH ~7.0. Using a slight excess of sensor and guide strands helped to prevent production of constitutively RNAi active guide+core duplexes. A PCR thermocycler with the following program was used:

Heat lid to 105° C.
Hold at 85° C. for 30 seconds to denature strand
Cool to 50° C. at a rate of 0.1° C./second
Hold for 45 min at 50° C.
Cool to 37° C. at a rate of 0.02° C./second
Cool to 4° C. at maximum rate and hold.

For assembly with purification, the sensor, core, and guide strands were mixed and assembled at 1 uM nominal concentration in 1×PBS using the above annealing protocol. Assembled constructs were then loaded on Bio-Rad mini protean 10% native PAGE gels in TBE buffer, and run at 125V at 4° C. for ~45 min. The bands corresponding to the Cond-siRNA were visualized and excised under UV lamp illumination.

The excised bands were extracted by electro-elution using a Harvard Apparatus Electroprep system according to the manufacturer's instructions. Gel pieces were placed in a 0.5 mL chamber sealed by a 100K MWCO filter membrane and a 2K MWCO filter membrane. Constructs were eluted through the 100K MWCO membrane and trapped in an adjacent 0.5 mL chamber formed by the 100K MWCO membrane and a second 2K MWCO membrane. Elution occurred in 0.1 M $Na_2HOP_4$ buffer (~pH 7.0) at 4° C. for ~45 min. The power supply was set to maintain a constant current of 15 mA with a voltage cutoff of 65 V.

Concentrations of purified constructs were calculated by comparison with Cond-siRNA standards at a known concentration using SYBR Gold staining on non-denaturing PAGE with quantitation using a Bio-Rad ChemiDoc XRS+ Imager.

Assembled constructs are best used immediately after assembly or purification. Constructs can also be stored in aliquots at −80° C. indefinitely. However, the freeze thaw cycles compromised construct quality and resulted in construct disassembly. Disassembled constructs can be re-assembled by repeating the thermal annealing immediately prior to assay.

The unpurified constructs were used in various tests because assembly yield was already high and purification did not consistently improve construct performance.

Example 4: Strand Displacement Assay

Pre-assembled constructs were prepared at 50 nM nominal concentration and combined 1:1 with 50 nM oligonucleotide activators (or PBS for control) at 37° C. in PBS buffer to obtain mixtures with 25 nM input signals and constructs. Construct-input combinations were then incubated in a PCR thermocycler at a constant 37° C. over 4 hours. Samples were collected at the indicated time points and immediately frozen at −80° C. in 1× native PAGE loading dye. At the end of the experiment, all samples were rapidly thawed, and analyzed using non-denaturing PAGE.

Example 5: Generation of Dual Luciferase Reporter and Activator Plasmids

All clones were generated using standard molecular biology protocols by annealing DNA oligos for the specific insert followed by ligation into the indicated sites of the parental vector. The accuracy of all constructs was verified by DNA sequencing.

Example 6: PsiCHECK Dual Luciferase Reporters

The indicated DNA oligos below were annealed and ligated into the XhoI and NotI sites of a psiCHECK 2 (Promega) dual Luciferase reporter. Nucleotides in bold font constitute the sense target sequence. Lower case nucleotides indicate restriction site 5' overhangs.
HIV U5 Region Target

```
                                        (SEQ ID NO: 103)
5'- tcgaGTCTGGTAACTAGAGATCCCTCAGACCC (SEQ ID NO: 104)
5'- ggccGGGTCTGAGGGATCTCTAGTTACCAGAC
```
MCL-1 Target

```
                                        (SEQ ID NO: 105)
5'- tcgaGCTGCATCGAACCATTAGCAGAAA (SEQ ID NO: 106)
5'- ggccTTTCTGCTAATGGTTCGATGCAGC
```

Example 7: RNA Input Transcripts for Signal Activation Experiments

The activator sequences were expressed as part of a chimeric tRNA transcript. The first part consists of a modified[5] tRNA$^{Lys3}$ with 3' terminal CCA, mature sequence shown in its entirety below. The CCA prevents endonucleolytic cleavage by the pre-tRNA processing enzyme, tRNAse Z. tRNA Pol III promoters were internal and contained within the coding sequence of the tRNA DNA.

For cloning a parental plasmid containing the first 69 nucleotides of tRNA$^{Lys3}$, terminating in an NruI restriction site[48] was used. Digestion of the parental plasmid with NruI generates a blunt end immediately following nucleotide tRNA 69. Annealed overlapping oligos encode the remaining modified tRNA nucleotides followed by the specified activation sequence. Each activation sequence terminates in a 12-base tetraloop (GGCGCAAGCC) (SEQ ID NO: 107) followed by a T6 run encoding the Pol III terminating sequence U4+RNA transcript sequences are listed below.

For constructs I and II, tRNA$^{Lys3}$ leader sequence, 5'->3': GCCCGGAUAGCUCGGUCGGUGGAGCAUCAGAC-UUUUAAUCUGAGGGUCCAGG GUUCGAGUCCCU-GUUCGUGCACCA (SEQ ID NO: 108)-Activator sequence. The sequence in bold is the binding site for the Northern blot probe. The activator sequences are listed in Table 1 and Table 2. Table 5 below lists the Northern blot probes.

TABLE 5

| Northern Blot Probes | |
|---|---|
| tRNA probe | CTGGACCCTCAGATTAAAAGTC (SEQ ID NO: 109) |
| CBFβ probe | CTCCATTTCCTCCCGATGAGACCTGTC (SEQ ID NO: 110) |
| MYH11 probe | CGCTTGGACTTCTCCAGCTCATGGAC (SEQ ID NO: 111) |
| U5 guide strand probe | AAAGGTAACTAGAGATCCCTCAGA (SEQ ID NO: 112) |

Example 8: Tissue Culture

All analyses utilized HCT 116 colorectal carcinoma cells. Cells were maintained using McCoy's 5A basal medium (Irvine Scientific, USA) supplemented with 10% fetal bovine serum (FBS), 1.5 m M L-glutamine (Irvine Scientific, USA) and 10 mM pyruvate (Irvine Scientific, USA) without antibiotics and kept in a humidified 5% CO$_2$ incubator at 37° C.

Example 9: Northern Blot Analysis

Analysis of activator expression was performed in 6-well plates using: 2 μg of plasmid DNA in 250 μL OptiMEM and 250 μL 1:50 diluted Lipofectamine 2000. Liposomes were allowed to form according to the manufacturer's instructions and added to cells with 2 mL fresh full medium. Medium was replaced at 18 hours, and depending on the length of transfection, at least once each subsequent day and 6 hours prior to RNA harvest. Analysis of OFF and pre-activated (ON) c-siRNAs were performed similarly; however, the indicated amount of RNAi complex was added to 2 μg of pBluescript plasmid as carrier in 250 μL OptiMEM.

Total RNA was harvested using 1000 μL RNA Stat-60 (Tel-Test, Inc) and processed according to the manufacturer's instructions with the addition of a second organic extraction using 1:1 phenol:chloroform extraction prior to precipitation; RNA pellets were washed twice with 70% ethanol prior to evaporation of excess ethanol and re-suspension in RNAse-free TE, pH 6.8.

For Northern analysis, 15 μg of total RNA were run on 8% (for activators) or 12% (for c-siRNAs) urea-PAGE gels (15 cm) with 32P-labeled Ambion Decade markers. Gels were electro-blotted to Hybond XL (GE Healthcare Life Sciences), pre-hybridized and hybridized at 37° C. using Sigma Perfect Hyb Plus and hybridized with 5-10 picomoles of P32-5' end-labeled oligo probe. Blots were washed at 37° C. with 4-5 changes of 2×SSC/1% SDS. With serial hybridizations, old oligo probe was removed from the membrane according to manufacturer's instructions and checked by re-exposure prior to re-hybridization unless otherwise indicated. Hybridization of U6 snRNA was used a loading control. Cloning procedures, oligos and all probe sequences are listed in the tables.

Example 10: Dual Luciferase Assays

Dual luciferase assays were performed using Promega Dual-Luciferase Reporter Assay System according to the manufacturer's instructions. The RNAi target sequence was cloned into the 3' UTR of the *Renilla* luciferase gene on a psiCHECK-2 (Promega) vector, and Firefly luciferase was used as a reference control.

Cells were incubated and transfected in 48-well cluster plates. Cells were seeded one day prior to transfections and transfected at 50% confluency. Each experiment was repeated in its entirety at least three times to obtain biological replicates. A single-step transfection protocol for FIGS. 5b-5h, and a two-step transfection protocol for FIGS. 5i-5k and FIG. 9a.

Single Step Co-Transfection Protocol:

For each experiment, a master mix of the psiCHECK (Promega Corporation) reporter plasmid in Opti-MEM (Thermo Fisher Scientific) was created. This master mix was separated into aliquots and either the pBluescript (Agilent) control or one of the activator plasmids added. The new mixtures were then divided yet again for addition of Cond-siRNA complexes at varying concentrations. Finally, a 1:50 dilution of Lipofectamine 2000 (L2K) was added at 1:1 volume ratio to the plasmid+Cond-siRNA mixtures to achieve the manufacturer recommended dilution of 1:100 L2K and incubated at room temperature according to the manufacturer's recommendation.

For each experimental condition (combination of activator and c-siRNA at a specific concentration), enough mixture (3.3× amount needed) was prepared to transfect 3 separate wells as technical replicates.

Thus, each well in the 48 well plate received a 40 μL transfection mixture consisting of: 16 μL (psiCHECK and activator plasmids in OptiMEM), 4 μL (50× Cond-siRNA in 1×PBS buffer), and 20 μL (1:50 dilution L2K). PBS was Phosphate Buffered Saline without calcium or magnesium treated with DEPC (diethyl pyrocarbonate) to remove any RNAse activity.

Immediately prior to transfection, the medium in each well was replaced with 160 μL of fresh medium, then added the 40 μL transfection mixture for a final volume of 200 μL/well with: 40 nanograms (ng) psiCHECK-2 dual luciferase reporter plasmid, 120 ng pBluescript or activator-expressing plasmid, and Cond-siRNA complexes at the indicated concentrations.

Two-Step Transfection Protocol:

This protocol was used to generate data for FIGS. 5i-5k and FIG. 9a.

Transfection 1 with Target and Activator Plasmids, Time-8 Hours

For the two-step transfections, a master mix of the psiCHECK (Promega Corporation) reporter plasmid in Opti-MEM (Thermo Fisher Scientific) was created. This master mix was separated into aliquots and either the pBluescript (Agilent) control or one of the activator plasmids were then added. A 1:50 dilution of Lipofectamine 2000 (L2K) was added at 1:1 volume ratio with the plasmid mixtures to achieve the manufacturer recommended dilution of 1:100 L2K and incubated at room temperature to form lipoplexes according to the manufacturer's recommendation.

For each experimental condition, enough mixture was prepared to transfect 3 separate wells as technical replicates. Thus, each well in the 48 well plate received a 40 μL transfection mixture consisting of: 20 μL (psiCHECK and activator plasmids in Opti-MEM), and 20 μL (1:50 dilution L2K).

Immediately prior to transfection, the medium in each well was replaced with 160 μL of fresh medium, then the 40 μL transfection mixture was added for a final volume of 200 μL/well containing: 40 nanograms (ng) psiCHECK-2 dual luciferase reporter plasmid, and 120 ng pBluescript or activator-expressing plasmid.

The transfection mixture was removed and gently washed with media after six hours for about 2 hours. 160 ul fresh medium was added to each well and cell incubation continued until the second transfection.

Transfection 2 with Cond-siRNA Complexes, Time-0

At 8 hours after transfection 1, Cond-siRNAs were transfected in varying concentrations as specified in the experiment using RNAiMAX reagent (ThermoFisher). For each experimental condition enough of each concentration of Cond-siRNA was prepared for technical triplicates of each target/activator combination in PBS. Each Cond-siRNA dilution was mixed with an equal volume of 1:50 RNAiMAX in OptiMEM and incubated at room temperature to form lipoplexes according to the manufacturer's instructions. Specifically, each well in the 48 well plate received a 40 μL transfection mixture consisting of: 20 μL Cond-siRNA at 10× final concentration (8 μL of PBS+12 μL of Opti-MEM), and 20 μL 1:50 dilution RNAiMAX.

Maintenance

Time 0 is marked by the addition of the co-transfection mixture to cells for the single-step protocol, and as the time of addition of the Cond-siRNA complexes (transfection #2) for the two-step protocol. Medium was replaced at 18 hours post-transfection, at least once each following day, and 6 hours before lysate preparation.

Lysate Preparation

At the designated time point for each experiment, 48 well plates were removed. Medium was carefully aspirated from each well. The wells were then washed once with 1×PBS and aspirated dry. 100 μL of 1× Promega Passive Lysis Buffer was added to each well. The plates were then covered in aluminum foil and either frozen at −80° C. or placed on a shaker for gentle agitation (~70 rpm) at room temperature for ~30 min. If frozen, cells were thawed on a shaker with gentle agitation for at least 30 min prior to dual luciferase assay. Before the assay, a visual inspection of the wells was used to ensure cells were well lysed.

Assay

Cell lysates were assayed using the Dual-Luciferase Reporter Assay Kit (Promega) according to the manufacturer's instructions. *Renilla* luciferase values were normalized to Firefly luciferase in each technical replicate (each well). Technical triplicates within the experiment were averaged to obtain a single biological replicate value. All graphs represent the results of at least three independent biological replicate experiments.

Example 11: Molecular Dynamics Simulations

Atomistic models of Cond-siRNAs were built using Nucleic Acid Builder[49] and custom scripts, and edited with the Accelrys (now BIOVIA, a division of Dassault Systems) Cerius[45] package to create appropriate chemical modifications.

A hybrid force field (FF) was created by combining previous Amber force field parameters reported for RNA[50], 2'-O-methyl[51], LNA[52], and phosphorothioate[53] modifications. Prior reports did not give a parameter set for LNA thymidine. FF parameters for the LNA sugar ring were derived from the LNA force field, and parameters for the base were derived from the Amber03 force field. Charges were calculated using the RESP ESP charge Derive (RED) server (q4md-forcefieldtools.org/REDServer/). FF parameters for non-DNA components such as the C3 linker, terminal amine modifications, and terminal PEG linkers were taken from the GAFF FF[54]. All structures were placed in a periodic box with 15 Å of spacing on each side and then solvated with TIP3 waters[55]. $Mg^{2+}$ ions were first added to neutralize half of the charge, and then $Na^+$ was added to neutralize the second half. Finally, additional $Na^+$ and $Cl^-$ ions were added to a concentration of 150 mM.

Molecular Dynamics simulations were run using LAMMPS13 GPU compatible release (Dec. 21, 2016) on nvidia K80 GPUs. Structures were minimized first with the steepest descent, then with conjugate gradient algorithms for 500 steps, and then equilibrated by MD simulations 310 K using the NVT ensemble over the course of 10 ps using a 1 fs timestep. The resulting structures then underwent 10 ps of NPT MD at 310 K, 350 atm to relax the periodic box and ensure positive net pressure. For NVT simulations, a Nose-Hoover thermostat was used with 100 fs time constant. For NPT simulations, a Nose-Hoover barostat was used with 1 ps time constant. Equilibrated structures then underwent 20 ns of MD at 310° K (NVT ensemble, 1 fs time step).

To obtain the structures presented in FIG. 9, the structure with the lowest potential energy from the MD trajectory was extracted and conjugate gradient energy minimization was applied for 500 steps. Constructs were visualized using the UCSF Chimera package[57]. Helical parameters were calculated from simulation trajectories using the X3DNA[58].

REFERENCES

1. Seeman, N. C. DNA in a material world. Nature 421, 427-431 (2003).
2. Guo, P. The emerging field of RNA nanotechnology. Nat Nano 5, 833-842 (2010).
3. Chen, Y.-J., Groves, B., Muscat, R. A. & Seelig, G. DNA nanotechnology from the test tube to the cell. Nat Nano 10, 748-760, doi:10.1038/nnano.2015.195 (2015).
4. Benenson, Y. Biomolecular computing systems: principles, progress and potential. Nat Rev Genet 13, 455-468, doi: http://www.nature.com/nrg/journal/v13/n7/suppinfo/nrg3197_S1.html (2012).
5. Yurke, B., Turberfield, A. J., Mills, A. P., Simmel, F. C. & Neumann, J. L. A DNA-fuelled molecular machine made of DNA. Nature 406, 605-608, doi:nature.com/nature/journal/v406/n6796/suppinfo/406605a0_S1.html (2000).
6. Srinivas, N. et al. On the biophysics and kinetics of toehold-mediated DNA strand displacement. Nucleic Acids Research, doi:10.1093/nar/gkt801 (2013).
7. Green, A. A. et al. Complex cellular logic computation using ribocomputing devices. Nature 548, 117-121, doi: 10.1038/nature23271 nature.com/nature/journal/v548/n7665/abs/nature23271.html#supplementaryinformation (2017).
8. Groves, B. et al. Computing in mammalian cells with nucleic acid strand exchange. Nat Nano 11, 287-294, doi:10.1038/nnano.2015.278 nature.com/nnano/journal/v11/n3/abs/nnano.2015.278.html#supplementaryinformation (2016).
9. Setten, R. L., Rossi, J. J. & Han, S. P. The current state and future directions of RNAi based therapeutics Nature Reviews Drug Discovery, In press (2019).
10. Bobbin, M. L. & Rossi, J. J. RNA Interference (RNAi)-Based Therapeutics: Delivering on the Promise? Annual Review of Pharmacology and Toxicology 56, 103-122, doi:10.1146/annurev-pharmtox-010715-103633 (2016).
11. Adams, D. et al. Patisiran, an RNAi Therapeutic, for Hereditary Transthyretin Amyloidosis. New England Journal of Medicine 379, 11-21, doi:10.1056/NEJMoa1716153 (2018).
12. Benenson, Y., Gil, B., Ben-Dor, U., Adar, R. & Shapiro, E. An autonomous molecular computer for logical control of gene expression. Nature 429, 423-429, doi:nature.com/nature/journal/v429/n6990/suppinfo/nature02551_S1.html (2004).
13. Kumar, D., Kim, S. H. & Yokobayashi, Y. Combinatorially Inducible RNA Interference Triggered by Chemically Modified Oligonucleotides. Journal of the American Chemical Society 133, 2783-2788, doi:10.1021/ja1107436 (2011).
14. Han, S. P., Barish, R. D. & Goddard, W. A. (Google Patents, 2015).
15. Han, S.-P., Goddard III, W. A., Scherer, L. & Rossi, J. J. Signal activatable constructs and related components compositions methods and systems. USA patent U.S. Pat. No. 9,725,715B2 (2015).
16. Hochrein, L. M., Ge, T. J., Schwarzkopf, M. & Pierce, N. A. Signal Transduction in Human Cell Lysate via Dynamic RNA Nanotechnology. ACS Synthetic Biology, doi:10.1021/acssynbio.8b00424 (2018).
17. Hochrein, L. M., Schwarzkopf, M., Shahgholi, M., Yin, P. & Pierce, N. A. Conditional Dicer Substrate Formation via Shape and Sequence Transduction with Small Conditional RNAs. Journal of the American Chemical Society 135, 17322-17330, doi:10.1021/ja404676x (2013).
18. Bindewald, E. et al. Multistrand Structure Prediction of Nucleic Acid Assemblies and Design of RNA Switches. Nano Letters 16, 1726-1735, doi:10.1021/acs.nanolett.5b04651 (2016).
19. Chatterjee, G., Chen, Y.-J. & Seelig, G. Nucleic Acid Strand Displacement with Synthetic mRNA Inputs in Living Mammalian Cells. ACS Synthetic Biology, doi: 10.1021/acssynbio.8b00288 (2018).
20. Li, X., Yang, X., Qi, J. & Seeman, N. C. Antiparallel DNA Double Crossover Molecules As Components for Nanoconstruction. Journal of the American Chemical Society 118, 6131-6140, doi:10.1021/ja960162o (1996).
21. Ha, M. & Kim, V. N. Regulation of microRNA biogenesis. Nature Reviews Molecular Cell Biology 15, 509, doi:10.1038/nrm3838 (2014).
22. MacRae, I. J. et al. Structural Basis for Double-Stranded RNA Processing by Dicer. Science (New York, N.Y.) 311, 195-198, doi:10.1126/science.1121638 (2006).

23. Kim, D.-H. et al. Synthetic dsRNA Dicer substrates enhance RNAi potency and efficacy. Nat Biotech 23, 222-226, doi:nature.com/nbt/journal/v23/n2/suppinfo/nbt1051_S1.html (2005).
24. Khvorova, A. & Watts, J. K. The chemical evolution of oligonucleotide therapies of clinical utility. Nat Biotech 35, 238-248, doi:10.1038/nbt.3765 (2017).
25. Srinivas, N. et al. On the biophysics and kinetics of toehold-mediated DNA strand displacement. Nucleic Acids Research 41, 10641-10658, doi:10.1093/nar/gkt801 (2013).
26. ORBAN, T. I. & IZAURRALDE, E. Decay of mRNAs targeted by RISC requires XRN1, the Ski complex, and the exosome. RNA (New York, N.Y.) 11, 459-469, doi: 10.1261/rna.7231505 (2005).
27. Hope, T. J. & Trono, D. Structure, Expression, and Regulation of the HIV Genome, <http://hivinsite.ucsf.edu/InSite?page=kb-00&doc=kb-02-01-02> (2000).
28. Kundu, M. & Liu, P. P. Function of the inv (16) fusion gene CBFB-MYH11. Current Opinion in Hematology 8, 201-205 (2001).
29. Look, A. T. Oncogenic Transcription Factors in the Human Acute Leukemias. Science (New York, N.Y.) 278, 1059-1064, doi:10.1126/science.278.5340.1059 (1997).
30. Plimpton, S. Fast Parallel Algorithms for Short-Range Molecular Dynamics. Journal of Computational Physics 117, 1-19, doi:dx.doi.org/10.1006/jcph.1995.1039 (1995).
31. Condon, D. E. et al. Optimization of an AMBER Force Field for the Artificial Nucleic Acid, LNA, and Benchmarking with NMR of L (CAAU). The Journal of Physical Chemistry B 118, 1216-1228, doi:10.1021/jp408909t (2014).
32. Lind, K. E., Sherlin, L. D., Mohan, V., Griffey, R. H. & Ferguson, D. M. in Molecular Modeling of Nucleic Acids Vol. 682 ACS Symposium Series Ch. 3, 41-54 (American Chemical Society, 1997).
33. Aduri, R. et al. AMBER Force Field Parameters for the Naturally Occurring Modified Nucleosides in RNA. Journal of Chemical Theory and Computation 3, 1464-1475, doi:10.1021/ct600329w (2007).
34. Iwamoto, N. et al. Control of phosphorothioate stereochemistry substantially increases the efficacy of antisense oligonucleotides. Nat Biotech advance online publication, doi:10.1038/nbt.3948 nature.com/nbt/journal/vaop/ncurrent/abs/nbt.3948.html #supplementaryinformation (2017).
35. Glaser, S. P. et al. Anti-apoptotic Mcl-1 is essential for the development and sustained growth of acute myeloid leukemia. Genes & Development 26, 120-125, doi: 10.1101/gad.182980.111 (2012).
36. Collingwood, M. A. et al. Chemical Modification Patterns Compatible with High Potency Dicer-Substrate Small Interfering RNAs. Oligonucleotides 18, 187-200, doi:10.1089/oli.2008.0123 (2008).
37. Yin, P. & Pierce, N. A. Triggered RNAi. USA patent U.S. Pat. No. 8,318,921B2 (2008).
38. Lee, H. Y., Zhou, K., Smith, A. M., Noland, C. L. & Doudna, J. A. Differential roles of human Dicer-binding proteins TRBP and PACT in small RNA processing. Nucleic Acids Research, doi:10.1093/nar/gkt361 (2013).
39. Han, S. P., Goddard, W. A., SCHERER, L. & Rossi, J. J. (Google Patents, 2015).
40. Silverman, S. K. Control of macromolecular structure and function using covalently attached double-stranded DNA constraints. Molecular BioSystems 3, 24-29, doi: 10.1039/B614116A (2007).
41. Engelen, W., Janssen, B. M. G. & Merkx, M. DNA-based control of protein activity. Chemical Communications 52, 3598-3610, doi:10.1039/C5CC09853J (2016).
42. Mukherjee, P., Leman, L. J., Griffin, J. H. & Ghadiri, M. R. Design of a DNA-Programmed Plasminogen Activator. Journal of the American Chemical Society 140, 15516-15524, doi:10.1021/jacs.8b10166 (2018).
43. Colasanti, A. V., Lu, X.-J. & Olson, W. K. Analyzing and Building Nucleic Acid Structures with 3DNA. e4401, doi:doi:10.3791/4401 (2013).
44. Zadeh, J. N. et al. NUPACK: Analysis and design of nucleic acid systems. Journal of Computational Chemistry 32, 170-173, doi:10.1002/jcc.21596 (2011).
45. Mathews, D. H., *Sabina*, J., Zuker, M. & Turner, D. H. Expanded sequence dependence of thermodynamic parameters improves prediction of RNA secondary structure11 Edited by I. Tinoco. Journal of Molecular Biology 288, 911-940, doi:doi.org/10.1006/jmbi.1999.2700 (1999).
46. Camacho, C. et al. BLAST+: architecture and applications. BMC Bioinformatics 10, 421-421, doi:10.1186/1471-2105-10-421 (2009).
47. Tolstrup, N. et al. OligoDesign: optimal design of LNA (locked nucleic acid) oligonucleotide capture probes for gene expression profiling. Nucleic Acids Research 31, 3758-3762 (2003).
48. Scherer, L. J., Frank, R. & Rossi, J. J. Optimization and characterization of tRNA shRNA expression constructs. Nucleic acids research 35, 2620-2628, doi:10.1093/nar/gkm103 (2007).
49. Macke, T. J. & Case, D. A. in Molecular Modeling of Nucleic Acids Vol. 682 ACS Symposium Series Ch. 24, 379-393 (American Chemical Society, 1997).
50. Duan, Y. et al. A point-charge force field for molecular mechanics simulations of proteins based on condensed-phase quantum mechanical calculations. Journal of Computational Chemistry 24, 1999-2012, doi:10.1002/jcc.10349 (2003).
51. Aduri, R. et al. AMBER Force Field Parameters for the Naturally Occurring Modified Nucleosides in RNA. Journal of Chemical Theory and Computation 3, 1464-1475, doi:10.1021/ct600329w (2007).
52. Condon, D. E. et al. Optimization of an AMBER Force Field for the Artificial Nucleic Acid, LNA, and Benchmarking with NMR of L (CAAU). The Journal of Physical Chemistry B 118, 1216-1228, doi:10.1021/jp408909t (2014).
53. Lind, K. E., Sherlin, L. D., Mohan, V., Griffey, R. H. & Ferguson, D. M. in Molecular Modeling of Nucleic Acids Vol. 682 ACS Symposium Series Ch. 3, 41-54 (American Chemical Society, 1997).
54. Wang, J., Wolf, R. M., Caldwell, J. W., Kollman, P. A. & Case, D. A. Development and testing of a general amber force field. Journal of Computational Chemistry 25, 1157-1174, doi:10.1002/jcc.20035 (2004).
55. Mark, P. & Nilsson, L. Structure and Dynamics of the TIP3P, SPC, and SPC/E Water Models at 298K. The Journal of Physical Chemistry A 105, 9954-9960, doi: 10.1021/jp003020w (2001).
56. Plimpton, S. Fast Parallel Algorithms for Short-Range Molecular Dynamics. Journal of Computational Physics 117, 1-19, doi:dx.doi.org/10.1006/jcph.1995.1039 (1995).
57. Pettersen, E. F. et al. UCSF Chimera-A visualization system for exploratory research and analysis. Journal of Computational Chemistry 25, 1605-1612, doi:10.1002/jcc.20084 (2004).
58. Colasanti, A. V., Lu, X.-J. & Olson, W. K. Analyzing and Building Nucleic Acid Structures with 3DNA. e4401, doi: doi:10.3791/4401 (2013).
59. Mathews et al., Expanded Sequence Dependence of Thermodynamic Parameters Improves Prediction of RNA Secondary Structure, J. Mol. Biol. (1999) 288: 911-940.
60. U.S. Pat. No. 9,029,524.
61. Meggers, et al., Acc. Chem. Res. (2010) 43(8): 1092-1102.
62. Schlegel et al., J. Am. Chem. Soc. (2017) 139(25): 8537-8546.

What is claimed is:

1. A programmable, conditionally activatable small interfering RNA (Cond-siRNA) construct comprising a sensor strand, a core strand, and a guide strand, wherein:
   (i) the sensor strand and the core strand form a sensor duplex,
   (ii) the guide strand and the core strand form a RNAi duplex, and
   (iii) the sensor duplex is attached to the RNAi duplex to form a single structure, wherein the terminal base on the 5' terminus of the core strand is a 2'-F or 2'-O-methyl and the terminal base on the 3' terminus of the core strand is a 2'-F or 2'-O-methyl, and wherein
      (a) 50% or less of the backbone positions in the sensor duplex domain of the sensor strand are phosphorothioate (PS) connections, or
      (b) the three bases of the core strand base-paired with the 3' terminus of the guide strand have a M*+*M pattern, wherein M is a 2'-F or 2'-O-methyl, * is a PS backbone connection, and + is an LNA base or other 2'-4' bridged base.

2. The Cond-siRNA construct of claim 1, wherein the sensor strand has an overhang that is not complementary to the core strand, and wherein the overhang on the sensor strand is capable of complementary binding to an input strand to form a toehold, thereby causing the displacement of the sensor strand from the core strand.

3. The Cond-siRNA construct of claim 1, comprising one or more of the following chemical modifications:
   A. the duplex domain of the sensor strand has one or more of the following features:
      a. 50% or more of the bases are chemically modified to resist nuclease degradation or increase the melting temperature of the duplex (Tm);
      b. 100% of the bases are chemically modified to resist nuclease degradation and increase Tm; and
      c. about 10%-50% of the bases are locked nucleic acid (LNA) or other chemically modified base with 2'-4' bridging modifications that substantially increase the Tm;
   B. the 5' and 3' termini of the core strand have one or more of the following features:
      a. the three terminal bases on the 5' have the pattern MRM, where M is a modified base (2'-O-methyl, 2'-F), and R is an RNA base;
      b. the three terminal bases on the 3' have the pattern MRM, where M is a modified base (2'-O-methyl, 2'-F), and R is an RNA base;
      c. the three terminal bases on the 3' and 5' do not have consecutive PS backbone modifications;
      d. the portions of the core strand that are base-paired with the sensor strand have an alternating chemical modification pattern (MR)n;
      e. the above where M is a chemically modified base that does not decrease Tm of the duplex when compared to the equivalent RNA base;
      f. any combination where both the 5' and the 3' ends of the core strand have at least one of the features from a-e; and
      g. the 3' and 5' regions of the core strand that are base-paired with the sensor strand are:
         (a) entirely made out of the pattern (M)n, where M is a 2'-O-methyl or 2'-F modified base, or
         (b) at least 50% of the bases in this area are 2'-O-methyl or 2' F, and, up to 30%, 50%, 80% or 100% of the backbone connections are not phosphorothioate;
   C. a core strand where the three bases base-paired with 3' terminus of the guide strand have one or more of the following features:
      a. A M*+*+ pattern;
      b. A +*+*+ pattern;
      c. A R*+*M pattern, where R is an RNA base;
      d. A R*+*+ pattern;

e. A +*M*M pattern; and
f. the patterns in a-e, where * can be either a PS backbone connection or an unmodified (phosphodiester) backbone connection; and
D. a guide strand with one or more of the following features:
a. 30% to 95% of the bases are chemically modified bases (2'-O-methyl, 2'-F, LNA, 2'-4' bridged bases);
b. where the two terminal bases on the 5' are chemically modified;
c. where the two terminal bases on the 5' have at least one LNA;
d. where the two terminal bases on the 5' are connected by a PS backbone;
e. where the two terminal bases on the 3' are both chemically modified;
f. where ~5% to 50% of backbone connections are PS; and
g. where the bases flanking the indicated site of Dicer cleavage are not chemically modified.

4. The Cond-siRNA construct of claim 1, wherein the duplex domain of the sensor strand has LNA modification, 2'-O-methyl modification, or both.

5. The Cond-siRNA construct of claim 1, wherein the duplex domain of the sensor strand does not have phosphorothioate (PS) modifications.

6. The Cond-siRNA construct of claim 2, wherein the toehold domain comprises one or more chemical modifications selected from LNA modification, 2'-O-methyl modification, PS modification, and a combination thereof.

7. The Cond-siRNA construct of claim 1, wherein the sensor duplex is 23 bp, and the RNAi duplex is 23 bp.

8. A method of activating a synthetic RNAi comprising administering the Cond-siRNA construct of claim 1 to a subject, wherein an input strand binds to the sensor strand causing displacement of the sensor strand from the Cond-siRNA, thereby to activate the RNAi in the Cond-siRNA construct.

9. The method of claim 8, wherein the input strand is a cellular RNA transcript.

10. A method of treating a disease or condition, comprising administering the Cond-siRNA construct of claim 1 to a subject in need thereof, wherein an input strand binds to the sensor strand causing displacement of the sensor strand from the Cond-siRNA, thereby to activate the RNAi in the Cond-siRNA construct, and wherein the RNAi targets the disease or the condition.

11. The method of claim 10, wherein the input strand is a cellular RNA transcript.

* * * * *

UNITED STATES PATENT AND TRADEMARK OFFICE
CERTIFICATE OF CORRECTION

PATENT NO. : 11,999,954 B2  
APPLICATION NO. : 17/172461  
DATED : June 4, 2024  
INVENTOR(S) : Si-ping Han et al.

Page 1 of 1

It is certified that error appears in the above-identified patent and that said Letters Patent is hereby corrected as shown below:

On the Title Page

In (73) Assignees section, change "Clty of Hope" to --City of Hope--.

Signed and Sealed this
Thirty-first Day of December, 2024

Derrick Brent
*Acting Director of the United States Patent and Trademark Office*